US011497792B2

(12) United States Patent
Kumar et al.

(10) Patent No.: US 11,497,792 B2
(45) Date of Patent: *Nov. 15, 2022

(54) METHODS FOR TREATMENT OF DUCHENNE MUSCULAR DYSTROPHY WITH FOLLISTATIN POLYPEPTIDES

(71) Applicant: Acceleron Pharma Inc., Cambridge, MA (US)

(72) Inventors: Ravindra Kumar, Acton, MA (US); Asya Grinberg, Lexington, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/943,289

(22) Filed: Jul. 30, 2020

(65) Prior Publication Data
US 2021/0177741 A1 Jun. 17, 2021

Related U.S. Application Data

(63) Continuation of application No. 15/983,191, filed on May 18, 2018, now Pat. No. 10,765,626, which is a continuation of application No. 15/075,051, filed on Mar. 18, 2016, now Pat. No. 10,010,498, which is a continuation-in-part of application No. 14/731,009, filed on Jun. 4, 2015, now Pat. No. 10,023,621.

(60) Provisional application No. 62/007,908, filed on Jun. 4, 2014.

(51) Int. Cl.
A61K 38/17 (2006.01)
A61K 47/68 (2017.01)
A61K 9/00 (2006.01)
A61P 21/06 (2006.01)
C07K 14/47 (2006.01)
C07K 19/00 (2006.01)
A61K 38/00 (2006.01)

(52) U.S. Cl.
CPC .......... *A61K 38/1709* (2013.01); *A61K 47/68* (2017.08); *A61P 21/06* (2018.01); *C07K 14/4703* (2013.01); *A61K 9/0019* (2013.01); *A61K 38/00* (2013.01); *C07K 19/00* (2013.01); *C07K 2319/30* (2013.01)

(58) Field of Classification Search
CPC .......................... C07K 14/4703; C07K 19/00; A61K 38/1709; A61K 38/00; A61P 21/06
See application file for complete search history.

(56) References Cited

U.S. PATENT DOCUMENTS

| 5,041,538 | A  | 8/1991  | Ling et al.  |
| 5,182,375 | A  | 1/1993  | Ling et al.  |
| 5,545,616 | A  | 8/1996  | Woodruff     |
| 5,654,404 | A  | 8/1997  | Roos et al.  |
| 6,004,937 | A  | 12/1999 | Wood et al.  |
| 6,599,876 | B2 | 7/2003  | Kojima       |
| 6,686,198 | B1 | 2/2004  | Melton et al. |
| 7,264,968 | B2 | 9/2007  | Melton et al. |
| 7,988,973 | B2 | 8/2011  | Sherman      |
| 8,895,016 | B2 | 11/2014 | Sherman et al. |
| 8,895,309 | B2 | 11/2014 | Kaspar et al. |
| 8,956,608 | B2 | 2/2015  | Walsh et al. |
| 9,957,309 | B2* | 5/2018 | Mineau ............ A61P 19/08 |
| 10,023,621 | B2* | 7/2018 | Kumar ............ C07K 14/4703 |
| 10,723,772 | B2* | 7/2020 | Mineau ........... C07K 14/4703 |
| 10,954,279 | B2* | 3/2021 | Kumar ............ C07K 14/4707 |
| 2003/0162714 | A1 | 8/2003 | Hill et al. |
| 2004/0209805 | A1 | 10/2004 | Phillips et al. |
| 2007/0135336 | A1 | 6/2007 | De Kretser et al. |
| 2007/0149458 | A1 | 6/2007 | Han et al. |
| 2007/0248609 | A1 | 10/2007 | De Kretser et al. |
| 2010/0028331 | A1 | 2/2010 | Sherman et al. |
| 2010/0028332 | A1 | 2/2010 | Sherman et al. |
| 2010/0061997 | A1 | 3/2010 | Lee et al. |
| 2010/0286374 | A1 | 11/2010 | Kannan et al. |
| 2012/0003218 | A1 | 1/2012 | Sherman et al. |
| 2012/0149876 | A1 | 6/2012 | Von Kreudenstein et al. |
| 2015/0023981 | A1 | 1/2015 | De Kretser et al. |
| 2015/0158923 | A1 | 6/2015 | Sherman et al. |
| 2015/0183845 | A1 | 7/2015 | Sherman et al. |
| 2016/0083440 | A1* | 3/2016 | Mineau ............ A61P 21/00 424/134.1 |
| 2016/0185836 | A1 | 6/2016 | Kumar et al. |
| 2016/0256526 | A1 | 9/2016 | Kumar et al. |
| 2016/0311874 | A1 | 10/2016 | Kumar et al. |
| 2018/0305421 | A1* | 10/2018 | Mineau ............ C07K 19/00 |

FOREIGN PATENT DOCUMENTS

| CN | 1993048 | 7/2007 |
| EP | 1 174 149 A1 | 1/2002 |
| WO | WO-92/13947 A1 | 8/1992 |
| WO | WO-1994/006456 A1 | 3/1994 |
| WO | WO-1995/10611 A1 | 4/1995 |
| WO | WO-97/15321 A1 | 5/1997 |
| WO | WO-1999/06559 A1 | 2/1999 |

(Continued)

OTHER PUBLICATIONS

Alignment of human follistatin with EMBOSS Needle performed Oct. 14, 2016 at http://www.ebi.ac.uk!Tools/psa/emboss_needle/).
Bowie, J.U., et al., "Deciphering the Message in Protein Sequences: Tolerance to Amino Acid Substitutions," Science, 257:1306-1310 (1990).
Borgnon et al, "Follistatin Allows Efficient Retroviral-Mediated Gene Transfer into Rat Liver," Biochemical and Biophysical Research Communications 328; pp. 937-943 (2005).
Bork, "Powers and Pitfalls in Sequence Analysis: The 70% Hurdle," Genome Research, 10:398-400 (2000).
Brenner, "Errors in genome annotation," Trends in Genetics, vol. 15(4): 132-133 (1999).

(Continued)

*Primary Examiner* — Zachary C Howard
(74) *Attorney, Agent, or Firm* — White & Case LLP

(57) ABSTRACT

The disclosure provides, in part, follistatin polypeptides that are suitable for use in local administration and methods for use.

20 Claims, 9 Drawing Sheets

Specification includes a Sequence Listing.

(56) References Cited

FOREIGN PATENT DOCUMENTS

| WO | WO-99/45949 A2 | 9/1999 |
|---|---|---|
| WO | WO-2001/009368 A1 | 2/2001 |
| WO | WO-2002/10214 A2 | 2/2002 |
| WO | WO-2002/085306 A2 | 10/2002 |
| WO | WO-2003/006057 A1 | 1/2003 |
| WO | WO-03/072714 A2 | 9/2003 |
| WO | WO-2004082710 A1 | 9/2004 |
| WO | WO-2004/108157 A2 | 12/2004 |
| WO | WO-2005025601 A1 | 3/2005 |
| WO | WO-2005/033134 A2 | 4/2005 |
| WO | WO-2005032578 A1 | 4/2005 |
| WO | WO-2005100563 A1 | 10/2005 |
| WO | WO-2006/012627 A2 | 2/2006 |
| WO | WO-2006/020884 A2 | 2/2006 |
| WO | WO-2006083182 A1 | 8/2006 |
| WO | WO-2007/067616 A2 | 6/2007 |
| WO | WO-2008030367 A2 | 3/2008 |
| WO | WO-2009/158025 A2 | 12/2009 |
| WO | WO-2009158035 A2 | 12/2009 |
| WO | WO-2012/025536 A1 | 3/2012 |
| WO | WO-2013/151665 A2 | 10/2013 |
| WO | WO-2013170315 A1 | 11/2013 |
| WO | WO-2014/003553 A1 | 1/2014 |
| WO | WO-2014/116981 A1 | 7/2014 |
| WO | WO-2014/187807 A1 | 11/2014 |
| WO | WO-2015/187977 A1 | 12/2015 |
| WO | WO-2016/154601 A1 | 9/2016 |
| WO | WO-2018/209242 A1 | 11/2018 |

OTHER PUBLICATIONS

Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-2138 (1990).

Cash et al., "Characterization of Follistatin-Type Domains and Their Contribution to Myostatin and Activin A Antagonism," Mol. Endocrinol. vol. 26(7): 1167-1178 (2012).

Datta-Mannan A. et al. "An Engineered Human Follistatin Variant: Insights into the Pharmacokinetic and Pharmocodynamic Relationships of a Novel Molecule with Broad Therapeutic Potential" The Journal of Pharmacology and Experimental Therapeutics (2013) 344(3): 616-623.

Datta-Mannan et al, "Insights into the Impact of Heterogeneous Glycosylation on the Pharmacokinetic Behavior of Follistatin-Fc-Based Biotherapeutics", Drug Metabolism & Disposition, 43(12), pp. 1882-1890 (Dec. 2015).

Doerks et al., "Protein annotation: detective work for function prediction," Trends in Genetics, vol. 14(6): 248-250 (1998).

Foley et al, "Evaluation of Systemic Follistatin as an Adjuvant to Stimulate Muscle Repair and Improve Motor Function in Pompe Mice," Molecular Therapy, vol. 18, No. 9 pp. 1584-1591 (Sep. 2010).

Gonzalez et al., "A coreceptor interaction between the CD28 and TNF receptor family members B and T lymphocyte attenuator and herpesvirus entry mediator," Pro Natl Acad Sci USA, 102:1116-1121 (2005).

Guo et al, "Overexpression of Mouse Follistatin Causes Reproductive Defects in Transgenic Mice," Molecular Endocrinology, vol. 12 No. 1, 11 pages (1998).

Haidet et al, "Long-term Enhancement of Skeletal Muscle Mass and Strength by Single Gene Administration of Myostatin Inhibitors," PNAS, vol. 105, No. 11, pp. 4318-4322, (Mar. 18, 2008).

Inouye et al, "Recombinant Expression of Human Follistatin with 315 and 288 Amino Acids: Chemical and Biological Comparison with Native Porcine Follistatin," Endocrinology, vol. 129, No. 2, pp. 815-822, (1991).

International Search Report PCT/US2015/034245 dated Aug. 21, 2015.

Klein et al., "Progress in overcoming the chain association issue in bispecific heterodimeric IgG antibodies," mAbs., vol. 4(6): 653-663 (2012).

Kota et al, "Follistatin Gene Delivery Enhances Muscle Growth and Strength in Nonhuman Primates," Sci Transl Med. 17 pages (Nov. 2009).

Lazar, E., et al., "Transforming Growth Factor α: Mutation of Aspartic Acid 47 and Leucine 48 Results in Different Biological Activities," Molecular and Cellular Biology, 8(3):1247-1252 (1988).

Lin et al., "Regulation of ovarian functions by the TGF-beta superfamily and follistatin," Reproduction, vol. 126: 133-148 (2003).

Miller et al, "Gene Transfer Demonstrates that Muscle is not a Primary Target for Non-cell-autonomous Toxicity in Familial Amyotrophic Lateral Sclerosis," PNAS, vol. 103, No. 51, pp. 19546-19551 (Dec. 19, 2006).

Nakatani et al, "Transgenic Expression of a Myostatin Inhibitor Derived from Follistatin Increases Skeletal Muscle Mass and Ameliorates Dystrophic Pathology in mdx Mice," the FASEB Journal, vol. 22, pp. 477-487 (Feb. 2008).

Ngo, J.T., et al., "Computational Complexity, Protein Structure Prediction, and the Levinthal Paradox," The Protein Folding Problem and Tertiary Structure Prediction, Merz et al., eds., Birkhauser, Boston, 433-440 and 492-495 (1994).

Pearsall et al., "Follistatin-based ligand trap ACE-083 induces localized hypertrophy of skeletal muscle with functional improvement in models of neuromuscular disease," Nature (Scientific Reports); vol. 9:11392 (14 pages (2019).

Rodino-Klapac et al, "Inhibition of Myostatin with Emphasis on Follistatin as a Therapy for Muscle Disease," Muscle Nerve, Mar.;39(3) 22 pages (Mar. 2009).

Rose et al, "Delivery of Recombinant Follistatin Lessens Disease Severity in a Mouse Model of Spinal Muscular Atrophy," Human Molecular Genetics, vol. 18, No. 6, pp. 997-1005 (Dec. 12, 2008).

Sahin et al (Encyclopedia of Cancer Jun. 1, 2015; pp. 1-4).

Sidis et al, "Heparin and Activin-Binding Determinants in Follistatin and FSTL3," Endocrinology, 146(1): pp. 130-136 (Jan. 2005).

Shimasaki et al., "Primary structure of the human follistatin precursor and its genomic organization," Proc Natl Acad Sci USA, 85:4218-4222 (1988).

Skolnick and Fetrow, "From Genes to protein structure and function: novel applications of computational approaches in the genomic era," Trends in Biotech. vol. 18(1): 34-39 (2000).

Stamler et al., "The Structure of FSTL3.Actinvin A Complex: Differential Binding of N-Terminal Domains Influences Follistatin-Type Antagonist Specificity," Journal of Biological Chemistry, vol. 283(47): 32831-32838 (2008).

Sugino et al., "Molecular Heterogeneity of Follistatin, an Activin-binding Protein," The Journal of Biological Chemistry, vol. 268(21): 15579-15587 (1993).

Takabe et al, "AdenovirMediated Overexpression of Follistatin Enlarges Intact Liver of Adult Rats," Hepatology, vol. 38, No. 5 pp. 1107-1115 (2003).

Tilbrook et al, "Human Recombinant Follistatin-288 Suppresses Plasma Concentrations of Follicle-Stimulating Hormone But is Not a Significant Regulator of Luteinizing Hormone in Castrated Rams," Biology of Reproduction, pp. 1353-1358 (1995).

Wang et al., "Analysis of Human Follistatin Structure: Identification of Two Discontinuous N-Terminal Sequences Coding for Activin A Binding and Structural Conseuqences of Activin Binding to Native Proteins," Endocrinology, vol. 141(9): 3183-3193 (2000).

Wells, J.A., "Additivity of Mutational Effects in Proteins," Biochemistry, 29(37):8509-8517 (1990).

Yaden B. C. et al. "Follistatin: A Novel Therapeutic for the Improvement of Muscle Regeneration" The Journal of Pharmacology and Experimental Therapeutics (2014) 349 (2): 355-371.

Ying, "Inhibins, Activins, and Follistatins: Gonadal Proteins Modulating the Secretion of Follicle-Stimulating Hormone," Endocrine Reviews, vol. 9(2): 267-293 (1998).

(56) References Cited

OTHER PUBLICATIONS

Zhu et al, "Follistatin Improves Skeletal Muscle Healing after Injury Disease through an Interaction with Muscle Regeneration, Angiogenesis, and Fibrosis," The American Journal of Pathology, vol. 179, No. 2, pp. 915-930 (Aug. 2011).

* cited by examiner

• Gastrocnemius muscle injected directly with FST(288)-IgG1

*p<0.05 vs PBS

*=p<0.05 vs PBS

METHODS FOR TREATMENT OF DUCHENNE MUSCULAR DYSTROPHY WITH FOLLISTATIN POLYPEPTIDES

CROSS-REFERENCE TO RELATED APPLICATIONS

This application is a continuation of U.S. application Ser. No. 15/983,191, filed May 18, 2018 (now allowed), which is a continuation Ser. No. 15/075,051, filed Mar. 18, 2016 (now U.S. Pat. No. 10,010,498), which is a continuation in part of U.S. application Ser. No. 14/731,009, filed Jun. 4, 2015 (now U.S. Pat. No. 10,023,621), which claims the benefit of priority to U.S. Provisional Application Ser. No. 62/007,908 (now expired), filed Jun. 4, 2014. The specifications of the foregoing applications are hereby incorporated in their entirety.

SEQUENCE LISTING

The instant application contains a Sequence Listing which has been submitted in ASCII format via EFS-Web and is hereby incorporated by reference in its entirety. Said ASCII copy, created on Jul. 29, 2020, is named 1848179-065-105_Seq.txt and is 129,066 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin/BMP10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat. Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Changes in muscle, bone, cartilage and other tissues may be achieved by agonizing or antagonizing signaling that is mediated by an appropriate TGF-beta family member. However, because members of the family may affect more than one tissue, it is desirable in some patient care situations to achieve therapeutic inhibition of members of this family in a localized, rather than systemic, manner. Thus, there is a need for agents that function as potent regulators of TGF-beta signaling and are appropriate for localized administration.

SUMMARY OF THE INVENTION

In part, the disclosure provides follistatin polypeptides that are designed to inhibit follistatin ligands (e.g. activin A, activin B, GDF8 and GDF11) in proximity to the tissue in which such follistatin polypeptides are administered, while having little or no systemic effects on the patient.

Follistatin polypeptides described herein include polypeptides comprising an amino acid sequence that is at least 80%, 85%, 90%, 91%, 92%, 93%, 94%, 95%, 96%, 97%, 98%, 99% or 100% to any of SEQ ID NOS: 1-4, 7-16 and 26-43. Optionally, the follistatin polypeptide is designed to dimerize or form higher order multimers. This may be achieved by fusing the follistatin sequence of a follistatin polypeptide to a domain that confers dimerization or multimerization. An example of such a domain is a constant domain of an immunoglobulin, including, for example, the Fc portion of an immunoglobulin. Optionally, the follistatin portion is connected directly to the heterologous portion, or an intervening sequence such as a linker may be employed. An example of a linker is the sequence TGGG. Optionally the follistatin polypeptide may exhibit heparin binding activity, in the manner that human follistatin-288 has heparin binding activity. Alternatively, the follistatin may have a masked heparin binding domain, in the manner of human follistatin-315. In part the disclosure provides therapeutically optimized follistatin polypeptides that comprise a portion of an immunoglobulin constant domain from a human IgG that has reduced ADCC or CDC activity relative to native human IgG1. Examples include IgG2, IgG3, IgG4, hybrid IgG2/4 and variants of IgG1, IgG2, IgG3 and IgG4. In part the disclosure provides an optimal active form of follistatin, comprising, consisting essentially of or consisting of the amino acid sequence of SEQ ID NO:15 or 16 that provides superior protein qualities and activity relative to the native FST(288) and FST(315) forms, particularly in the context of dimeric fusion proteins such as follistatin-Fc proteins.

In certain aspects, the disclosure provides a polypeptide comprising a first amino acid sequence and a second amino acid sequence, wherein the first amino acid sequence consists of an amino acid sequence selected from the group consisting of SEQ ID NO: 15 and 16, and wherein the second amino acid sequence comprises a constant domain of an immunoglobulin. Optionally, there is a linker polypeptide positioned between the first amino acid sequence and second amino acid sequence. Optionally the linker polypeptide comprises, consists essentially of, or consists of the sequence TGGG. Optionally, the second amino acid sequence comprises, consists essentially of or consists of, a constant domain of an IgG immunoglobulin. Optionally, the second amino acid sequence comprises, consists essentially of or consists of a constant domain of an IgG immunoglobulin that has reduced ADCC activity relative to human IgG1. Optionally, the second amino acid sequence comprises, consists essentially of or consists of a constant domain of an IgG immunoglobulin that has reduced CDC activity relative to human IgG1. Optionally, the second amino acid sequence comprises, consists essentially of or consists of a constant domain of an IgG immunoglobulin selected from the group: IgG1, IgG2 and IgG4. Optionally, the second amino acid sequence comprises or consists of an Fc portion of an immunoglobulin, such as an IgG immunoglobulin, which may be an immunoglobulin that has reduced ADCC, CDC or both relative to human IgG1, examples of which include IgG2, IgG4 and an IgG2/4 hybrid or various mutations of any of IgG1, IgG2, IgG3 or IgG4. In certain aspects the disclosure provides follistatin polypeptides that comprise, consist essentially of or consist of an amino acid sequence that is at least 90%, 91%, 92%, 93%, 94%, 95%, 96%, 97%, 98%, 99% or 100% identical to the sequence selected from the group of SEQ ID NO: 38-43. In certain aspects the disclosure provides follistatin polypeptides that comprise, consist essentially of or consist of an amino acid sequence that is at least 90%, 91%, 92%, 93%, 94%, 95%, 96%, 97%, 98%, 99% or 100% identical to the sequence selected from the group of SEQ ID NO: 26-28 and 32-34. In certain aspects the disclosure provides follistatin polypeptides that comprise, consist essentially of or consist of an amino acid sequence that is at least 90%, 91%, 92%, 93%, 94%, 95%, 96%, 97%, 98%, 99% or 100% identical to the sequence selected from the group of SEQ ID NO: 29-31 and 35-37. Desirable follistatin polypeptides may bind to one or more ligands selected from the group consisting of: myostatin, GDF-11, activin A and activin B with a KD less than 1 nM, 100 pM, 50 pM or 10 pM. In certain aspects any of the above mentioned polypeptides may be dimers, including heterodimers or homodimers, or higher order multimers. Any of the above mentioned polypeptides may be incorporated into a pharmaceutical preparation.

In certain aspects the disclosure provides nucleic acids encoding any of the follistatin polypeptides disclosed herein and cells comprising such nucleic acids, which cells may be used to produce the follistatin polypeptides.

In certain aspects, the disclosure provides methods for treating tissues or organs by administering a follistatin polypeptide directly to such tissue. For example, the disclosure provides a method of increasing muscle size or strength in a patient, the method comprising administering an effective amount of a follistatin polypeptide by an intramuscular route of administration to a targeted muscle of a patient in need thereof, wherein the increased muscle size or strength occurs in the targeted muscle, and wherein the follistatin polypeptide does not have a substantial systemic effect on muscle size or strength. The targeted muscle may be damaged, weakened or deficient, as may be the case in a variety of muscle disorders including muscular dystrophies (such as Duchenne muscular dystrophy, Becker's muscular dystrophy and fascioscapulohumeral muscular dystrophy), inflammatory muscle disorders (such as inclusion body myositis), muscle injury or trauma, muscle disuse (as may occur after prolonged bed rest or limb immobilization) and muscle atrophy or weakening as a consequence of aging, cancer or chronic diseases of various types. The methods may also be applied to muscle that is healthy but for which an increase in muscle size or strength of the targeted muscle is desired. Additionally, administration of a follistatin polypeptide to muscle may cause a general decrease in body fat and thereby be useful for treating obesity or other disorders associated with excess body fat, and optionally, follistatin may be administered directly to adipose tissue. The follistatin polypeptide may be administered to only one targeted muscle or to more than one targeted muscle. The methods and follistatin polypeptides may be used to achieve effects on the targeted tissue, e.g. muscle, without substantial effects on other tissues, such as a non-targeted muscle or other organs. As a consequence systemic effects of follistatin may not be observed. For example, a muscle that is contralateral to a targeted muscle may not substantially increase in size or strength or there may be no substantial effect in the patient on a measure selected from the group consisting of: serum FSH levels, liver size, hematocrit, hemoglobin and reticulocyte levels.

DETAILED DESCRIPTION

1. Overview

Figure 1:
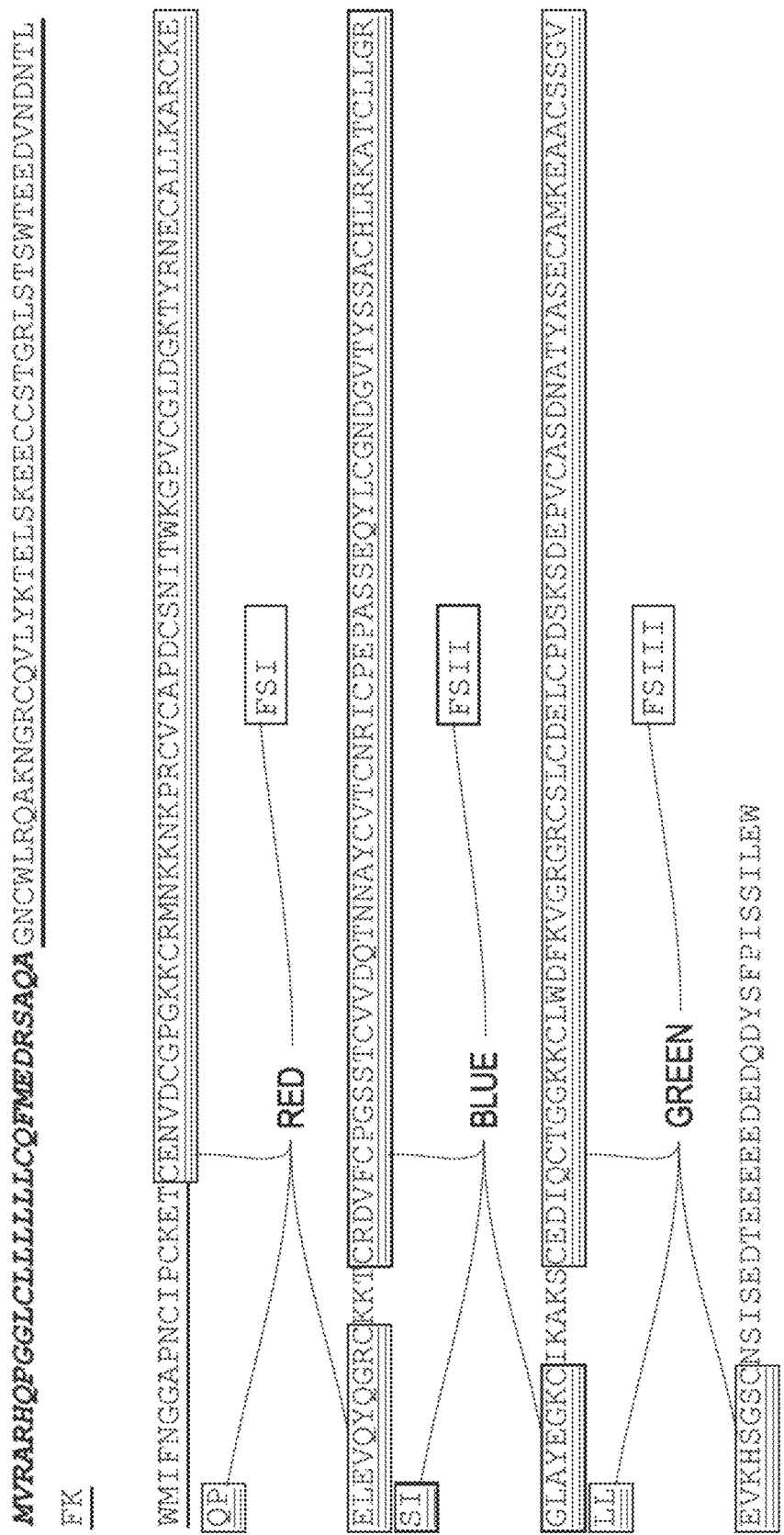
FIG. 1 shows the full, unprocessed amino acid sequence of human follistatin 315 (SEQ ID NO:3). The leader sequence is italicized in bold font, the follistatin N-terminal region (FSN) is indicated by single underlining, and the three follistatin domains (FSDs) are indicated by double underlining. In particular, follistatin domain I (FSDI) is indicated in red font, follistatin domain II (FSDII) is indicated in blue font, and the follistatin domain III (FSDIII) is indicated in green font.

In certain aspects, the present disclosure relates to follistatin polypeptides. As used herein, the term "follistatin" refers to a family of follistatin (FST) proteins and follistatin-related proteins, derived from any species. Follistatin is an autocrine glycoprotein that is expressed in nearly all tissues of higher animals. It was initially isolated from follicular fluid and was identified as a protein fraction that inhibited follicle-stimulating hormone (FSH) secretion from the anterior pituitary, and therefore was designated as FSH-suppressing protein (FSP). Subsequently, its primary function has been determined to be the binding and neutralization of members of the TGF-β superfamily including, for example, activin, a paracrine hormone that enhances secretion of FSH in the anterior pituitary.

The term "follistatin polypeptide" is used to refer to polypeptides comprising any naturally occurring polypeptide of the follistatin family as well as any variants thereof (including mutants, fragments, fusions, and peptidomimetic forms) that retain a useful activity, including, for example, ligand binding (e.g., myostatin, GDF-11, activin A, activin B) or heparin binding. For example, follistatin polypeptides include polypeptides comprising an amino acid sequence derived from the sequence of any known follistatin having a sequence at least about 80% identical to the sequence of a follistatin polypeptide, and preferably at least 85%, 90%, 95%, 97%, 99% or greater identity. The term "follistatin polypeptide" may refer to fusion proteins that comprise any of the polypeptides mentioned above along with a heterologous (non-follistatin) portion. An amino acid sequence is understood to be heterologous to follistatin if it is not uniquely found in the long (315 amino acid) form of human follistatin, represented by SEQ ID NO:3. Many examples of heterologous portions are provided herein, and such heterologous portions may be immediately adjacent, by amino acid sequence, to the follistatin polypeptide portion of a fusion protein, or separated by intervening amino acid sequence, such as a linker or other sequence.

Follistatin is a single-chain polypeptide with a range of molecular weights from 31 to 49 kDa based on alternative mRNA splicing and variable glycosylation of the protein. The alternatively spliced mRNAs encode two proteins of 315 amino acids (i.e., FST315) and 288 amino acids (i.e., FST288); follistatin 315 can be further proteolytically degraded to follistatin 303 (FST303). Analysis of the amino acid sequence has revealed that the native human follistatin polypeptide comprises five domains (from the N-terminal side): a signal sequence peptide (amino acids 1-29 of SEQ ID NO:1), an N-terminal domain (FSN) (amino acids 30-94 of SEQ ID NO:1), follistatin domain I (FSDI) (amino acids 95-164 of SEQ ID NO:1), follistatin domain II (FSDII) (amino acids (168-239 of SEQ ID NO:1), and follistatin domain III (FSDIII) (amino acids 245-316 of SEQ ID NO:1). See PNAS, U.S.A., 1988, Vol. 85, No 12, pp 4218-4222.

The human follistatin-288 (FST288) precursor has the following amino acid sequence, with the signal peptide indicated in bold, the N-terminal domain (FSN) indicated by single underlining, and the follistatin domains I-III (FSI, FSII, FSIII) indicated by double underlining.

(SEQ ID NO: 1)
MVRARHQPGGLCLLLLLLLCQFMEDRSQAGNCWLRQAKNGRCQVLYKTELS

KEECCSTGRLSTSWTEEDVNDTLFKWMIFNGGAPNCIPCKETCENVDCG

PGKKCRMNKKNKPRCVCAPDCSNITWKGPVCGLDGKTYRNECALLKARCK

EQPELEVQYQGRCKKTCRDVFCPGSSTCVVDQTNNAYCVTCNRICPEPAS

SEQYLCGNDGVTYSSACHLRKATCLLGRSIGLAYEGKCIKAKSCEDIQCT

GGKKCLWDFKVGRGRCSLCDELCPDSKSDEPVCASDNATYASECAMKEAA

CSSGVLLEVKHSGSCN

The processed (mature) human follistatin variant FST (288) has the following amino acid sequence with the N-terminal domain indicated by single underlining, and the follistatin domains I-III indicated by double underlining. Moreover, it will be appreciated that any of the initial amino acids G or N, prior to the first cysteine may be removed by processing or intentionally eliminated without any consequence, and polypeptides comprising such slightly smaller polypeptides are further included.

(SEQ ID NO: 2)
GNCWLRQAKNGRCQVLYKTELSKEECCSTGRLSTSWTEEDVNDTLFKWMI

FNGGAPNCIPCKETCENVDCGPGKKCRMNKKNKPRCVCAPDCSNITWKGP

VCGLDGKTYRNECALLKARCKEQPELEVQYQGRCKKTCRDVFCPGSSTCV

VDQTNNAYCVTCNRICPEPASSEQYLCGNDGVTYSSACHLRKATCLLGRS

IGLAYEGKCIKAKSCEDIQCTGGKKCLWDFKVGRGRCSLCDELCPDSKSD

EPVCASDNATYASECAMKEAACSSGVLLEVKHSGSCN

The human follistatin-315 (FST315) precursor has the following amino acid sequence, with the signal peptide indicated in bold, the N-terminal domain (FSN) indicated by single underlining, and the follistatin domains I-III (FSI, FSII, FSIII) indicated by double underlining (NCBI Accession Number AAH04107.1; 344 amino acids).

(SEQ ID NO: 3)
MVRARHQPGGLCLLLLLLLCQFMEDRSAQAGNCWLRQAKNGRCQVLYKTEL

SKEECCSTGRLSTSWTEEDVNDTLFKWMIFNGGAPNCIPCKETCENVDC

GPGKKCRMNKKNKPRCVCAPDCSNITWKGPVCGLDGKTYRNECALLKARC

-continued

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECAMKEA

ACSSGVLLEVKHSGSCNSISEDTEEEEEDEDQDYSFPISSILEW

The processed (mature) human FST(315) has the following amino acid sequence with the N-terminal domain indicated by single underlining, and the follistatin domains I-III indicated by double underlining. Moreover, it will be appreciated that any of the initial amino acids G or N, prior to the first cysteine may be removed by processing or intentionally eliminated without any consequence, and polypeptides comprising such slightly smaller polypeptides are further included.

(SEQ ID NO: 4)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEW

Follistatin polypeptides of the disclosure may include any naturally occurring domain of a follistatin protein as well as variants thereof (e.g., mutants, fragments, and peptidomimetic forms) that retain a useful activity. For example, it is well-known that FST(315) and FST(288) have high affinity for both activin (activin A and activin B) and myostatin (and the closely related GDF11) and that the follistatin domains (e.g., FSN and FSD I-III) are thought to be involved in the binding of such TGF-β ligands. However, it believed that each of these three domains may have a different affinity for these TGF-β ligands. For example, a recent study has demonstrated that polypeptide constructs comprising only the N-terminal domain (FSN) and two FSDI domains in tandem retained high affinity for myostatin, demonstrated little or no affinity for activin and promoted systemic muscle growth when introduced into a mouse by gene expression (Nakatani et al., The FASEB Journal, Vol. 22477-487 (2008)).

Additionally, the FSDI domain contains the heparin binding domain of human follistatin, which has the amino acid sequence of KKCRIVINKKNKPR (SEQ ID NO: 5). This heparin binding domain can be represented as BBXBXXBBXBXB (SEQ ID NO:6) wherein "B" means a basic amino acid, particularly lysine (K) or arginine (R). Accordingly, the present disclosure encompasses, in part, variant follistatin proteins that demonstrate selective binding and/or inhibition of a given TGF-β ligand relative to the naturally occurring FST protein (e.g., maintaining high-affinity for myostain while having a significantly reduced affinity for activin).

In certain aspects, the disclosure includes polypeptides comprising the FSN domain, as set forth below, and, for example, one or more heterologous polypeptide, and moreover, it will be appreciated that any of the initial amino acids G or N, prior to the first cysteine may be deleted, as in the example shown below (SEQ ID NO:8).

(SEQ ID NO: 7)
GNCWLRQAKNGRCQVLYKTELSKEECCSTGRLSTSWTEEDVNDNTLFKWM

IFNGGAPNCIPCKET (SEQ ID NO: 8)
CWLRQAKNGRCQVLYKTELSKEECCSTGRLSTSWTEEDVNDNTLFKWMIF

NGGAPNCIPCKET

In certain aspects, the disclosure includes polypeptides comprising the FSDI domain which contains the minimal core activities of myostatin (and/or GDF11) binding along with heparin binding as set forth below, and, for example, one or more heterologous polypeptide.

(SEQ ID NO: 9)
CENVDCGPGKKCRMNKKNKPRCVCAPDCSNITWKGPVCGLDGKTYRNECA

LLKARCKEQPELEVQYQGRC

An FSDI sequence may be advantageously maintained in structural context by expression as a polypeptide further comprising the FSN domain. Accordingly, the disclosure includes polypeptides comprising the FSN-FSDI sequence, as set forth below (SEQ ID NO:10), and, for example, one or more heterologous polypeptide, and moreover, it will be appreciated that any of the initial amino acids G or N, prior to the first cysteine may be removed by processing or intentionally eliminated without any consequence, and polypeptides comprising such slightly smaller polypeptides are further included.

(SEQ ID NO: 10)
CWLRQAKNGRCQVLYKTELSKEECCSTGRLSTSWTEEDVNDNTLFKWMIF

NGGAPNCIPCKETCENVDCGPGKKCRMNKKNKPRCVCAPDCSNITWKGPV

CGLDGKTYRNECALLKARCKEQPELEVQYQGRC

As demonstrated by Nakani et al., an FSN-FSDI-FSDI construct is sufficient to confer systemic muscle growth when genetically expressed in a mouse, and accordingly the disclosure includes polypeptides comprising the amino acid sequences below and, for example, one or more heterologous polypeptide.

(SEQ ID NO: 11)
CWLRQAKNGRCQVLYKTELSKEECCSTGRLSTSWTEEDVNDNTLFKWMIF

NGGAPNCIPCKETCENVDCGPGKKCRMNKKNKPRCVCAPDCSNITWKGPV

CGLDGKTYRNECALLKARCKEQPELEVQYQGRCKKTCENVDCGPGKKCRM

NKKNKPRCVCAPDCSNTIWKGPVCGLDGKTYRNECALLKARCKEQPELEV

QYQGRC

While the FSDI sequence confers myostatin and GDF11 binding, it has been demonstrated that activins, particularly Activin A but also Activin B, are also negative regulators of muscle, and therefore a follistatin polypeptide that inhibits both the myostatin/GDF11 group and the activin A/activin B group may provide a more potent muscle effect. Moreover, in view of the findings herein demonstrating the low systemic availability of certain follistatin polypeptides, particularly those comprising a heparin binding domain, and more particularly in a homodimeric form, such as an Fc fusion, safety concerns associated with the known effects of activin inhibition on the reproductive axis and other tissues are alleviated. Given that FSDII confers activin A and B binding, the disclosure provides polypeptides comprising FSDI and FSDII (SEQ ID NO:12), as well as FSN-FSDI-FSDII constructs (SEQ ID NOS: 13) and, for example, one or more heterologous polypeptide.

(SEQ ID NO: 12)

```
CENVDCGPGKKCRMNKKNKPRCVCAPDCSNITWKGPVCGLDGKTYRNECA
LLKARCKEQPELEVQYQGRCKKTCRDVFCPGSSTCVVDQTNNAYCVTCNR
ICPEPASSEQYLCGNDGVTYSSACHLRKATCLLGRSIGLAYEGKC
```

(SEQ ID NO: 13)

```
CWLRQAKNGRCQVLYKTELSKEECCSTGRLSTSWTEEDVNDNTLFKWMIF
NGGAPNCIPCKETCENVDCGPGKKCRMNKKNKPRCVCAPDCSNITWKGPV
CGLDGKTYRNECALLKARCKEQPELEVQYQGRCKKTCRDVFCPGSSTCVV
DQTNNAYCVTCNRICPEPASSEQYLCGNDGVTYSSACHLRKATCLLGRSI
GLAYEGKC
```

As described in the Examples, a follistatin polypeptide of 291 amino acids (representing a truncation of the naturally occurring FST-315) has advantageous properties. Accordingly, unprocessed (SEQ ID NO: 14) and mature FST(291) (SEQ ID NO: 15) polypeptides are included in the disclosure and may be combined with heterologous proteins. Moreover, it will be appreciated that any of the initial amino acids G or N, prior to the first cysteine may be removed by processing or intentionally eliminated without any consequence, and polypeptides comprising such slightly smaller polypeptides are further included, such as the example shown below (SEQ ID NO:16).

(SEQ ID NO: 14)

```
MVRARHQPGGLCLLLLLLCQFMEDRSAQAGNCWLRQAKNGRCQVLYKTEL
SKEECCSTGRLSTSWTEEDVNDNTLFKWMIFNGGAPNCIPCKETCENVDC
GPGKKCRMNKKNKPRCVCAPDCSNITWKGPVCGLDGKTYRNECALLKARC
KEQPELEVQYQGRCKKTCRDVFCPGSSTCVVDQTNNAYCVTCNRICPEPA
SSEQYLCGNDGVTYSSACHLRKATCLLGRSIGLAYEGKCIKAKSCEDIQC
TGGKKCLWDFKVGRGRCSLCDELCPDSKSDEPVCASDNATYASECAMKEA
ACSSGVLLEVKHSGSCNSIS
```

(SEQ ID NO: 15)

```
GNCWLRQAKNGRCQVLYKTELSKEECCSTGRLSTSWTEEDVNDNTLFKWM
IFNGGAPNCIPCKETCENVDCGPGKKCRMNKKNKPRCVCAPDCSNITWKG
PVCGLDGKTYRNECALLKARCKEQPELEVQYQGRCKKTCRDVFCPGSSTC
VVDQTNNAYCVTCNRICPEPASSEQYLCGNDGVTYSSACHLRKATCLLGR
SIGLAYEGKCIKAKSCEDIQCTGGKKCLWDFKVGRGRCSLCDELCPDSKS
DEPVCASDNATYASECAMKEAACSSGVLLEVKHSGSCNSIS
```

(SEQ ID NO: 16)

```
CWLRQAKNGRCQVLYKTELSKEECCSTGRLSTSWTEEDVNDNTLFKWMIF
NGGAPNCIPCKETCENVDCGPGKKCRMNKKNKPRCVCAPDCSNITWKGPV
CGLDGKTYRNECALLKARCKEQPELEVQYQGRCKKTCRDVFCPGSSTCVV
DQTNNAYCVTCNRICPEPASSEQYLCGNDGVTYSSACHLRKATCLLGRSI
```

-continued

```
GLAYEGKCIKAKSCEDIQCTGGKKCLWDFKVGRGRCSLCDELCPDSKSDE
PVCASDNATYASECAMKEAACSSGVLLEVKHSGSCNSIS
```

In certain embodiments, the present invention relates to antagonizing a ligand of follistatin (also referred to as a follistatin ligand) with a subject follistatin polypeptide (e.g., an FST-IgG fusion polypeptide). Thus, compositions and methods of the present disclosure are useful for treating disorders associated with abnormal activity of one or more ligands of follistatin. Exemplary ligands of follistatin include some TGF-β family members, such as activin A, activin B, myostatin (GDF8) and GDF11.

Follistatin proteins herein may be referred to as FST. If followed by a number, such as FST(288), this indicates that the protein is the 288 form of follistatin. If presented as FST(288)-Fc, this indicates a C-terminal Fc fusion to the FST(288), which may or may not include an intervening linker. The Fc in this instance may be any immunoglobulin Fc portion as that term is defined herein. If presented as FST(288)-IgG2, this indicates a C-terminal Fc fusion to the FST(288) of the Fc portion of human IgG2.

Activins are dimeric polypeptide growth factors and belong to the TGF-β superfamily. There are three activins (A, B, and AB) that are homo/heterodimers of two closely related β subunits ($\beta_A\beta_A$, $\beta_B\beta_B$, and $\beta_A\beta_B$). Additional activins C and E have been identified, although the function of these proteins is poorly understood. In the TGF-β superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc SocEp Biol Med. 198:500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It was suggested that activin A acts as a natural regulator of erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Activin has also been implicated as a negative regulator of muscle mass and function, and activin antagonists can promote muscle growth or counteract muscle loss in vivo. Link and Nishi, Exp Cell Res. 1997 Jun. 15; 233(2):350-62; He et al., Anat Embryol (Berl). 2005 June; 209(5):401-7; Souza et al. Mol Endocrinol. 2008 December; 22(12):2689-702; Am J Physiol Endocrinol Metab. 2009 July; 297(1):E157-64; Gilson et al. Zhou et al. Cell. 2010 Aug. 20; 142(4):531-43.

Growth and Differentiation Factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle (McPherron et al., Nature, 1997, 387:83-90). Similar increases in skeletal muscle mass are evident in naturally occurring mutations of GDF8 in cattle (Ashmore et al., 1974, Growth, 38:501-507; Swatland and Kieffer, J. Anim. Sci., 1994, 38:752-757; McPherron and Lee, Proc. Natl. Acad. Sci. USA, 1997, 94:12457-12461; and Kambadur et al., Genome Res., 1997, 7:910-915) and, strikingly, in humans (Schuelke et al., N Engl J Med 2004; 350:2682-8). Studies have also shown that muscle wasting associated with HIV-infection in humans is accompanied by increases in GDF8 protein expression (Gonzalez-Cadavid et al., PNAS, 1998, 95:14938-43). In addition, GDF8 can modulate the production of muscle-specific enzymes (e.g., creatine kinase) and modulate myoblast cell proliferation (WO 00/43781). The GDF8 propeptide can noncovalently bind to the mature GDF8 domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). Other proteins which bind to GDF8 or structurally related proteins and inhibit their biological activity include follistatin, and potentially, follistatin-related proteins (Gamer et al. (1999) Dev. Biol., 208: 222-232).

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Δ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. However, in common usage and in the instant application, the term "homologous," when modified with an adverb such as "highly," may refer to sequence similarity and may or may not relate to a common evolutionary origin.

The term "sequence similarity," in all its grammatical forms, refers to the degree of identity or correspondence between nucleic acid or amino acid sequences that may or may not share a common evolutionary origin.

2. Follistatin Polypeptides

In certain aspects, the disclosure relates to follistatin polypeptides (e.g., FST-Fc polypeptides), and particularly truncated forms exemplified by polypeptides comprising SEQ ID NO:2, 7, 8, 9, 10, 11, 12, 13, 14, 15 or 16, and variants thereof. Optionally, the fragments, functional variants, and modified forms have similar, the same or improved biological activities of their corresponding wild-type follistatin polypeptides. For example, a follistatin variant of the disclosure may bind to and inhibit function of a follistatin ligand (e.g., activin A, activin AB, activin B, and GDF8). Optionally, a follistatin polypeptide modulates growth of tissues, particularly muscle. Examples of follistatin polypeptides include polypeptides comprising, consisting essentially of or consisting of the amino acid sequences by any of SEQ ID Nos. 1-16 and 26-43, as well as polypeptides comprising, consisting essentially of or consisting of amino acid sequences that are at least 80%, 85%, 90%, 91%, 92%, 93%, 94%, 95%, 96%, 97%, 98%, 99% or 100% identical to an amino acid sequence of any of SEQ ID Nos. 1-16 and 26-43. Variations on these polypeptides may be prepared according to the following guidance. The numbering of amino acids in the follistatin polypeptides is based on the sequence of SEQ ID NO:1, regardless of whether the native leader sequence is used.

As described above, follistatin is characterized by three cysteine-rich regions (i.e., FS domains I-III) that are believed to mediate follistatin-ligand binding. Furthermore, researchers have demonstrated that polypeptide constructs comprising only one of the three FS-binding domains (e.g., FSDI) retains strong affinity towards certain follistatin-ligands (e.g., myostatin) and is biologically active in vivo. See Nakatani et al., The FASEB Journal, Vol. 22477-487 (2008). Therefore, variant follistatin polypeptides of the disclosure may comprise one or more active portions of a follistatin protein. For example, constructs of the disclosure may begin at a residue corresponding to amino acids 30-95 of SEQ ID NO:1 and end at a position corresponding to amino acids 316-344 of SEQ ID NO:1. Other examples include constructs that begin at a position from 30-95 of SEQ ID NO:1 and end at a position corresponding to amino acids 164-167 or 238-244. Others may include any of SEQ ID Nos. 7-16.

The follistatin variations described herein may be combined in various ways with each other or with heterologous amino acid sequences. For example, variant follistatin proteins of the disclosure include polypeptides that comprise one or more FS domains selected from FSDI (amino acids 95-164 of SEQ ID NO:1 (i.e., SEQ ID NO:2), FSDII (amino acids 168-239 of SEQ ID NO:1), or FSDIII (amino acids 245-316 of SEQ ID NO:1) as well as proteins that comprise one or more FS domains selected from a sequence at least 80%, 85%, 90%, 92%, 95%, 96%, 97%, 98% or 99% identical to FSDI (amino acids 95-164 of SEQ ID NO:1 (i.e., SEQ ID NO:2), FSDII (amino acids 168-239 of SEQ ID NO:1), or FSDIII (amino acids 245-316 of SEQ ID NO:1). These FS domains may be combined in any order within a variant follistatin polypeptide of the disclosure provided that such recombinant proteins maintain the desired activity including, for example, follistatin ligand-binding activity (e.g., myostatin) and biological activity (e.g., inducing muscle mass and/or strength). Examples of such follistatin variant polypeptides include, for example, polypeptides having domain structures such as FSDI-FSDII-FSDIII, FSDI-FSDIII, FSDI-FSDI-FSDIII, FSDI-FSDII, FSDI-FSDI, FSN-FSDI-FSDII-FSDIII, FSN-FSDI-FSDII, FSN-FSDI- FSDI, FSN-FSDI-FSDIII, FSN-FSDI-FSDI-FSDIII, and polypeptides obtained by fusing other heterologous polypeptides to the N-termini or the C-termini of these polypeptides. These domains may be directly linked or liked via a linker polypeptide. Optionally, polypeptide linkers may be any sequence and may comprise 1-50, preferably 1-10, and more preferably 1-5 amino acids. In certain aspects, preferred linkers contain no cysteine amino acids.

In some embodiments, follistatin variants of the disclosure have reduced or abolished binding affinity for one or more follistatin ligands. In certain aspects, the disclosure provides follistatin variants that have reduced or abolished binding affinity for activin. In certain aspects, the disclosure provides follistatin variants that have reduced or abolished binding affinity for activin but retain high affinity for myostatin.

In certain aspects, the disclosure provides follistatin variants that do not comprise a sequence corresponding to the FSDII domain or functionally active FSDII domain. For example, follistatin polypeptides of the disclosure may include a variant obtained through partial or complete deletion of the FSDII domain. In certain aspects, such follistatin variants include the deletion of one or more cysteine residues within the FSDII region or substitution with non-cysteine amino acids.

The follistatin proteins of the disclosure may comprise a signal sequence. The signal sequence can be a native signal sequence of a follistatin protein (e.g., amino acids 1-29 of SEQ ID NO:1) or a signal sequence from another protein, such as tissue plasminogen activator (TPA) signal sequence or a honey bee melatin (HBM) signal sequence.

Further N-linked glycosylation sites (N-X-S/T) may be added to a follistatin polypeptide, and may increase the serum half-life of an FST-Fc fusion protein. N-X-S/T sequences may be generally introduced at positions outside the ligand-binding pocket. N-X-S/T sequences may be introduced into the linker between the follistatin sequence and the Fc or other fusion component. Such a site may be introduced with minimal effort by introducing an N in the correct position with respect to a pre-existing S or T, or by introducing an S or T at a position corresponding to a pre-existing N. Any S that is predicted to be glycosylated may be altered to a T without creating an immunogenic site, because of the protection afforded by the glycosylation. Likewise, any T that is predicted to be glycosylated may be altered to an S. Accordingly, a follistatin variant may include one or more additional, non-endogenous N-linked glycosylation consensus sequences.

In certain embodiments, the present disclosure contemplates making functional variants by modifying the structure of a follistatin polypeptide for such purposes as enhancing therapeutic efficacy, or stability (e.g., ex vivo shelf life and resistance to proteolytic degradation in vivo). Modified follistatin polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a follistatin polypeptide results in a functional homolog can be readily determined by assessing the ability of the variant follistatin polypeptide to produce a response in cells in a fashion similar to the wild-type follistatin polypeptide, or to bind to one or more ligands, such as activin or myostatin in a fashion similar to wild-type follistatin.

In certain embodiments, the present invention contemplates specific mutations of the follistatin polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type follistatin polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a follistatin polypeptide is by chemical or enzymatic coupling of glycosides to the follistatin polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIB polypeptide may be accomplished chemically and/or enzymatically. Chemical deglycosylation may involve, for example, exposure of the follistatin polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on follistatin polypeptides can be achieved by the use of a variety of endo- and exo-glycosidases as described by Thotakura et al. (1987) Meth. Enzymol. 138:350. The sequence of a follistatin polypeptide may be adjusted, as appropriate, depending on the type of expression system used, as mammalian, yeast, insect and plant cells may all introduce differing glycosylation patterns that can be affected by the amino acid sequence of the peptide. In general, follistatin proteins for use in humans will be expressed in a mammalian cell line that provides proper glycosylation, such as HEK293 or CHO cell lines, although other mammalian expression cell lines are expected to be useful as well.

This disclosure further contemplates a method of generating variants, particularly sets of combinatorial variants of an follistatin polypeptide, including, optionally, truncation variants; pools of combinatorial mutants are especially useful for identifying functional variant sequences. The purpose of screening such combinatorial libraries may be to generate, for example, follistatin polypeptide variants that have altered properties, such as altered pharmacokinetics, or altered ligand binding. A variety of screening assays are provided below, and such assays may be used to evaluate variants. For example, a follistatin polypeptide variant may be screened for ability to bind to a follistatin polypeptide, to prevent binding of a follistatin ligand to a follistatin polypeptide.

The activity of a follistatin polypeptide or its variants may also be tested in a cell-based or in vivo assay. For example, the effect of a follistatin polypeptide variant on the expression of genes involved in muscle production may be assessed. This may, as needed, be performed in the presence of one or more recombinant follistatin ligand proteins (e.g., activin A), and cells may be transfected so as to produce a follistatin polypeptide and/or variants thereof, and optionally, a follistatin ligand. Likewise, a follistatin polypeptide may be administered to a mouse or other animal, and one or more muscle properties, such as muscle mass or strength may be assessed. Such assays are well known and routine in the art. A responsive reporter gene may be used in such cell lines to monitor effects on downstream signaling.

Combinatorially-derived variants can be generated which have a selective potency relative to a naturally occurring follistatin polypeptide. Such variant proteins, when expressed from recombinant DNA constructs, can be used in gene therapy protocols. Likewise, mutagenesis can give rise to variants which have intracellular half-lives dramatically different than the corresponding a wild-type follistatin polypeptide. For example, the altered protein can be rendered either more stable or less stable to proteolytic degradation or other processes which result in destruction of, or otherwise inactivation of a native follistatin polypeptide. Such variants, and the genes which encode them, can be utilized to alter follistatin polypeptide levels by modulating the half-life of the follistatin polypeptides. For instance, a short half-life can give rise to more transient biological effects and, when part of an inducible expression system, can allow tighter control of recombinant follistatin polypeptide levels within the cell.

In certain embodiments, the follistatin polypeptides of the disclosure may further comprise post-translational modifications in addition to any that are naturally present in the follistatin polypeptides. Such modifications include, but are not limited to, acetylation, carboxylation, glycosylation, phosphorylation, lipidation, and acylation. As a result, the modified follistatin polypeptides may contain non-amino acid elements, such as polyethylene glycols, lipids, poly- or mono-saccharide, and phosphates. Effects of such non-amino acid elements on the functionality of a follistatin polypeptide may be tested as described herein for other follistatin polypeptide variants. When a follistatin polypeptide is produced in cells by cleaving a nascent form of the follistatin polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the follistatin polypeptides.

In certain aspects, functional variants or modified forms of the follistatin polypeptides include fusion proteins having at least a portion of a follistatin polypeptide and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$) fusion partners. As another example, a fusion domain may be selected so as to facilitate detection of the follistatin polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a follistatin polypeptide is fused with a domain that stabilizes the follistatin polypeptide in vivo (a "stabilizer" domain). By "stabilizing" is meant anything that increases serum half-life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

As specific examples, the present disclosure provides fusion proteins comprising follistatin polypeptides fused to a polypeptide comprising a constant domain of an immunoglobulin, such as a CH1 CH2 or CH3 domain of an immunoglobulin or an Fc. Fc domains derived from human IgG1 and IgG2 are provided below (SEQ ID NO: 17 and SEQ ID NO:18, respectively). As described herein, an IgG2, IgG4 or IgG2/4 Fc domain is particularly advantageous for fusion with follistatin polypeptides that retain heparin binding activity because these Fc species have reduced CDC and/or ADCC activity which may be harmful to the cells to which these heparin binding polypeptides may adhere. Other mutations are known that decrease either CDC or ADCC activity, and collectively, any of these variants are included in the disclosure and may be used as advantageous components of a follistatin fusion protein. Optionally, the Fc domain of SEQ ID NO:17 has one or more mutations at residues such as Asp-265, Lys-322, and Asn-434 (numbered in accordance with the corresponding full-length IgG1). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

Examples of human IgG1 and IgG2 amino acid sequences that may be employed are shown below:

IgG1
(SEQ ID NO: 17)
THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNV

FSCSVMHEALHNHYTQKSLSLSPGK

IgG2
(SEQ ID NO: 18)
VECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVS

NKGLPAPIEKTISKTKGQPREPQVYTLPPSREEMTKNQVSLTCLVKGFYP

SDIAVEWESNGQPENNYKTTPPMLDSDGSFFLYSKLTVDKSRWQQGNVFS

CSVMHEALHNHYTQKSLSLSPGK

It is understood that different elements of the fusion proteins may be arranged in any manner that is consistent with the desired functionality. For example, a follistatin polypeptide may be placed C-terminal to a heterologous domain, or, alternatively, a heterologous domain may be placed C-terminal to a follistatin polypeptide. The follistatin polypeptide domain and the heterologous domain need not be adjacent in a fusion protein, and additional domains or amino acid sequences may be included C- or N-terminal to either domain or between the domains.

As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. It is also understood that a follistatin polypeptide may comprise only a domain of an immunoglobulin, such as a CH1 domain, a CH2 domain or a CH3 domain. Many of these domains confer desirable pharmacokinetic properties as well as dimerization or higher order multimerization.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087 and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613). Additionally, in many instances, the C-terminal lysine, or K, will be removed and thus any of the polypeptides described herein may omit the C-terminal K that is found in an Fc domain, such as those shown in SEQ ID NO: 17 or SEQ ID NO: 18.

In certain embodiments, the follistatin polypeptides of the present disclosure contain one or more modifications that are capable of stabilizing the follistatin polypeptides. For example, such modifications enhance the in vitro half-life of the follistatin polypeptides, enhance circulatory half-life of the follistatin polypeptides or reducing proteolytic degradation of the follistatin polypeptides. Such stabilizing modifications include, but are not limited to, fusion proteins (including, for example, fusion proteins comprising a follistatin polypeptide and a stabilizer domain), modifications of a glycosylation site (including, for example, addition of a glycosylation site to a follistatin polypeptide), and modifications of carbohydrate moiety (including, for example, removal of carbohydrate moieties from a follistatin polypeptide). In the case of fusion proteins, a follistatin polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the follistatin polypeptides, which are isolated from, or otherwise substantially free of, other proteins.

In certain embodiments, follistatin polypeptides (unmodified or modified) of the disclosure can be produced by a variety of art-known techniques. For example, such follistatin polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the follistatin polypeptides, fragments or variants thereof may be recombinantly produced using various expression systems (e.g., *E. coli*, Chinese Hamster Ovary cells, COS cells, baculovirus) as is well known in the art (also see below). In a further embodiment, the modified or unmodified follistatin polypeptides may be produced by digestion of naturally occurring or recombinantly produced full-length follistatin polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such follistatin polypeptides may be produced from naturally occurring or recombinantly produced full-length follistatin polypeptides such as standard techniques known in the art, such as by chemical cleavage (e.g., cyanogen bromide, hydroxylamine).

3. Nucleic Acids Encoding Follistatin Polypeptides

In certain aspects, the invention provides isolated and/or recombinant nucleic acids encoding any of the follistatin polypeptides disclosed herein. The subject nucleic acids may be single-stranded or double stranded. Such nucleic acids may be DNA or RNA molecules. These nucleic acids are may be used, for example, in methods for making follistatin polypeptides.

For example, the following sequence encodes a naturally occurring human follistatin precursor polypeptide (SEQ ID NO: 19) (NCBI Accession Number BC004107.2, 1032 bp):

atggtccgcgcgaggcaccagccgggtgggctttgcctcctgctgctgct gctctgccagttcatggaggaccgcagtgcccaggctgggaactgctggc tccgtcaagcgaagaacggccgctgccaggtcctgtacaagaccgaactg agcaaggaggagtgctgcagcaccggccggctgagcacctcgtggaccga ggaggacgtgaatgacaacacactcttcaagtggatgattttcaacgggg gcgcccccaactgcatccctgtaaagaaacgtgtgagaacgtggactgt ggacctgggaaaaaatgccgaatgaacaagaagaacaaaccccgctgcgt ctgcgccccggattgttccaacatcacctggaagggtccagtctgcgggc tggatgggaaaacctaccgcaatgaatgtgcactcctaaaggcaagatgt aaagagcagccagaactggaagtccagtaccaaggcagatgtaaaaagac ttgtcgggatgttttctgtccaggcagctccacatgtgtggtggaccaga ccaataatgcctactgtgtgacctgtaatcggatttgcccagagcctgct tcctctgagcaatatctctgtgggaatgatggagtcacctactccagtgc ctgccacctgagaaaggctacctgcctgctgggcagatctattggattag cctatgagggaaagtgtatcaaagcaaagtcctgtgaagatatccagtgc actggtgggaaaaaatgtttatgggatttcaaggttgggagaggccggtg ttccctctgtgatgagctgtgccctgacagtaagtcggatgagcctgtct gtgccagtgacaatgccacttatgccagcgagtgtgccatgaaggaagct gcctgctcctcaggtgtgctactggaagtaaagcactccggatcttgcaa ctccatttcggaagacaccgaggaagaggaggaagatgaagaccaggact acagctttcctatatcttctattctagagtgg The following sequence encodes the mature FST(315) polypeptide (SEQ ID NO: 20).

gggaactgctggctccgtcaagcgaagaacggccgctgccaggtcctgta caagaccgaactgagcaaggaggagtgctgcagcaccggccggctgagca cctcgtggaccgaggaggacgtgaatgacaacacactcttcaagtggatg attttcaacggggcgcccccaactgcatccctgtaaagaaacgtgtga gaacgtggactgtggacctgggaaaaaatgccgaatgaacaagaagaaca aaccccgctgcgtctgcgccccggattgttccaacatcacctggaagggt ccagtctgcgggctggatgggaaaacctaccgcaatgaatgtgcactcct aaaggcaagatgtaaagagcagccagaactggaagtccagtaccaaggca gatgtaaaaagacttgtcgggatgttttctgtccaggcagctccacatgt gtggtggaccagaccaataatgcctactgtgtgacctgtaatcggatttg cccagagcctgcttcctctgagcaatatctctgtgggaatgatggagtca cctactccagtgcctgccacctgagaaaggctacctgcctgctgggcaga tctattggattagcctatgagggaaagtgtatcaaagcaaagtcctgtga agatatccagtgcactggtgggaaaaaatgtttatgggatttcaaggttg ggagaggccggtgttccctctgtgatgagctgtgccctgacagtaagtcg gatgagcctgtctgtgccagtgacaatgccacttatgccagcgagtgtgc catgaaggaagctgcctgctcctcaggtgtgctactggaagtaaagcact ccggatcttgcaactccatttcggaagacaccgaggaagaggaggaagat gaagaccaggactacagctttcctatatcttctattctagagtgg The following sequence encodes the FST(288) polypeptide (SEQ ID NO: 21).

gggaactgctggctccgtcaagcgaagaacggccgctgccaggtcctgta caagaccgaactgagcaaggaggagtgctgcagcaccggccggctgagca cctcgtggaccgaggaggacgtgaatgacaacacactcttcaagtggatg attttcaacggggcgcccccaactgcatccctgtaaagaaacgtgtga gaacgtggactgtggacctgggaaaaaatgccgaatgaacaagaagaaca aaccccgctgcgtctgcgccccggattgttccaacatcacctggaagggt ccagtctgcgggctggatgggaaaacctaccgcaatgaatgtgcactcct aaaggcaagatgtaaagagcagccagaactggaagtccagtaccaaggca gatgtaaaaagacttgtcgggatgttttctgtccaggcagctccacatgt gtggtggaccagaccaataatgcctactgtgtgacctgtaatcggatttg cccagagcctgcttcctctgagcaatatctctgtgggaatgatggagtca cctactccagtgcctgccacctgagaaaggctacctgcctgctgggcaga tctattggattagcctatgagggaaagtgtatcaaagcaaagtcctgtga agatatccagtgcactggtgggaaaaaatgtttatgggatttcaaggttg ggagaggccggtgttccctctgtgatgagctgtgccctgacagtaagtcg gatgagcctgtctgtgccagtgacaatgccacttatgccagcgagtgtgc catgaaggaagctgcctgctcctcaggtgtgctactggaagtaaagcact ccggatcttgcaac The following sequence encodes the mature FST(291) polypeptide (SEQ ID NO: 22).

gggaactgctggctccgtcaagcgaagaacggccgctgccaggtcctgta caagaccgaactgagcaaggaggagtgctgcagcaccggccggctgagca cctcgtggaccgaggaggacgtgaatgacaacacactcttcaagtggatg attttcaacggggcgcccccaactgcatccctgtaaagaaacgtgtga gaacgtggactgtggacctgggaaaaaatgccgaatgaacaagaagaaca aaccccgctgcgtctgcgccccggattgttccaacatcacctggaagggt -continued

```
ccagtctgcgggctggatgggaaaacctaccgcaatgaatgtgcactcct aaaggcaagatgtaaagagcagccagaactggaagtccagtaccaaggca gatgtaaaaagacttgtcgggatgttttctgtccaggcagctccacatgt gtggtggaccagaccaataatgcctactgtgtgacctgtaatcggatttg cccagagcctgcttcctctgagcaatatctctgtgggaatgatggagtca cctactccagtgcctgccacctgagaaaggctacctgcctgctgggcaga tctattggattagcctatgagggaaagtgtatcaaagcaaagtcctgtga agatatccagtgcactggtgggaaaaaatgtttatgggatttcaaggttg ggagaggccggtgttccctctgtgatgagctgtgccctgacagtaagtcg gatgagcctgtctgtgccagtgacaatgccacttatgccagcgagtgtgc catgaaggaagctgcctgctcctcaggtgtgctactggaagtaaagcact ccggatcttgcaactccatttcgtgg
```

In certain aspects, the subject nucleic acids encoding follistatin polypeptides are further understood to include nucleic acids that are variants of SEQ ID NOs: 19-22. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 19-22.

In certain embodiments, the disclosure provides isolated or recombinant nucleic acid sequences that are at least 80%, 85%, 90%, 95%, 96% 97%, 98%, 99%, or 100% identical to SEQ ID NOs: 19-22, and particularly those portions thereof that are derived from follistatin (nucleotides corresponding to amino acids 95-164 of SEQ ID NO:1). One of ordinary skill in the art will appreciate that nucleic acid sequences complementary to SEQ ID NOs: 19-22, and variants of SEQ ID NO: 19-22 are also within the scope of this disclosure. In further embodiments, the nucleic acid sequences of the disclosure can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NOs: 19-22, complement sequence of SEQ ID NOs: 19-22, or fragments thereof (e.g., nucleotides 19-22).

One of ordinary skill in the art will understand readily that appropriate stringency conditions that promote DNA hybridization can be varied. One of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids that differ from the nucleic acids as set forth in SEQ ID NOs: 19-22 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations that do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the subject nucleic acid is provided in an expression vector comprising a nucleotide sequence encoding a follistatin polypeptide and operably linked to at least one regulatory sequence. Regulatory sequences are art-recognized and are selected to direct expression of the follistatin polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a follistatin polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant follistatin polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the ß-gal containing pBlueBac III).

In certain embodiments, a vector will be designed for production of the subject follistatin polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject follistatin polypeptides in cells propagated in culture, e.g., to produce proteins, including fusion proteins or variant proteins, for purification.

This disclosure also pertains to a host cell transfected with a recombinant gene including a coding sequence (e.g., SEQ ID NOs: 19-22) for one or more of the subject follistatin polypeptides. The host cell may be any prokaryotic or eukaryotic cell. For example, a follistatin polypeptide of the disclosure may be expressed in bacterial cells such as E. coli, insect cells (e.g., using a baculovirus expression system), yeast, or mammalian cells. Other suitable host cells are known to those skilled in the art.

Accordingly, the present disclosure further pertains to methods of producing the subject follistatin polypeptides. For example, a host cell transfected with an expression vector encoding a follistatin polypeptide can be cultured under appropriate conditions to allow expression of the follistatin polypeptide to occur. The follistatin polypeptide may be secreted and isolated from a mixture of cells and medium containing the follistatin polypeptide. Alternatively, the follistatin polypeptide may be retained cytoplasmically or in a membrane fraction and the cells harvested, lysed and the protein isolated. A cell culture includes host cells, media and other byproducts. Suitable media for cell culture are well known in the art. The subject follistatin polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the follistatin polypeptides. In a preferred embodiment, the follistatin polypeptide is a fusion protein containing a domain that facilitates its purification.

In another embodiment, a fusion gene coding for a purification leader sequence, such as a poly-(His)/enterokinase cleavage site sequence at the N-terminus of the desired portion of the recombinant follistatin polypeptide, can allow purification of the expressed fusion protein by affinity chromatography using a $Ni^{2+}$ metal resin. The purification leader sequence can then be subsequently removed by treatment with enterokinase to provide the purified follistatin polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed to generate a chimeric gene sequence (see, for example, *Current Protocols in Molecular Biology,* eds. Ausubel et al., John Wiley & Sons: 1992).

4. Exemplary Therapeutic Uses

In certain embodiments, compositions of the present disclosure, including for example FST(288)-IgG1, FST (288)-IgG2, FST(291)-IgG1, FST(291)-IgG2, FST(315)-IgG1, FST(315)-IgG2, and any of the other follistatin polypeptides disclosed herein, can be used for treating or preventing a disease or condition that is described in this section, including diseases or disorders that are associated with abnormal activity of a follistatin polypeptide and/or a follistatin ligand (e.g., GDF8). These diseases, disorders or conditions are generally referred to herein as "follistatin-associated conditions." In certain embodiments, the present disclosure provides methods of treating or preventing an individual in need thereof through administering to the individual a therapeutically effective amount of a follistatin polypeptide as described above. These methods are particularly aimed at therapeutic and prophylactic treatments of animals, and more particularly, humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes amelioration or elimination of the condition once it has been established.

Follistatin-ligand complexes play essential roles in tissue growth as well as early developmental processes such as the correct formation of various structures or in one or more post-developmental capacities including sexual development, pituitary hormone production, and creation of muscle. Thus, follistatin-associated conditions include abnormal tissue growth and developmental defects.

Exemplary conditions for treatment include neuromuscular disorders (e.g., muscular dystrophy and muscle atrophy), congestive obstructive pulmonary disease (and muscle wasting associated with COPD), muscle wasting syndrome, sarcopenia, and cachexia. Other exemplary conditions include musculodegenerative and neuromuscular disorders, tissue repair (e.g., wound healing), and neurodegenerative diseases (e.g., amyotrophic lateral sclerosis).

In certain embodiments, compositions (e.g., FST-Fc polypeptides) of the invention are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject follistatin polypeptides include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Myotonic Dystrophy (MMD) (also known as Steinert's Disease), Oculopharyngeal Muscular Dystrophy (OPMD), Distal Muscular Dystrophy (DD), Congenital Muscular Dystrophy (CMD).

Duchenne Muscular Dystrophy (DMD) was first described by the French neurologist Guillaume Benjamin Amand Duchenne in the 1860s. Becker Muscular Dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either insufficient in quantity or poor in quality. Having some dystrophin protects the muscles of those with BMD from degenerating as badly or as quickly as those of people with DMD.

For example, recent research demonstrates that blocking or eliminating function of GDF8 (a follistatin ligand) in vivo can effectively treat at least certain symptoms in DMD and BMD patients. Thus, the subject follistatin polypeptides may act as GDF8 inhibitors (antagonists), and constitute an alternative means of blocking the functions of GDF8 in vivo in DMD and BMD patients.

Similarly, the subject follistatin polypeptides provide an effective means to increase muscle mass in other disease conditions that are in need of muscle growth. For example, ALS, also called Lou Gehrig's disease (motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles. Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset.

Charcot-Marie-Tooth Disease (CMT) may be treated by local administration of the follistatin polypeptides described herein. CMT is a group of inherited disorders affecting the peripheral nerves and resulting in progressive, and often local, muscle weakness and degeneration. Aspects of the disease that may be treated include foot deformity (very high arched feet); foot drop (inability to hold foot horizontal); "Slapping" gait (feet slap on the floor when walking because of foot drop); loss of muscle in the lower legs; numbness in the feet; difficulty with balance; or weakness in the arms and hands.

Muscles of patients with a variety of systemic muscle disorders may be treated with the follistatin polypeptides disclosed herein, including: Lambert-Eaton Myasthenic Syndrome (LEMS); Metabolic Dystrophies; Spinal Muscular Atrophy (SMA); Dermatomyositis (DM); Distal Muscular Dystrophy (DD); Emery-Dreifuss Muscular Dystrophy (EDMD); Endocrine Myopathies; Friedreich's Ataxia (FA); Inherited Myopathies; Mitochondrial Myopathy; Myasthenia Gravis (MG); Polymyositis (PM).

Muscles of patients with a post-surgical or disuse atrophy of one or muscles may be treated with the follistatin polypeptides disclosed herein including atrophy after: Hip Fracture; Total Hip Arthroplasty (THA); Total Knee Arthroplasty (TKA) or Rotator Cuff surgery.

Muscles of patients suffering from a variety of other diseases that cause muscle loss or weakening may be treated with the follistatin polypeptides disclosed herein, including muscles of patients with the following diseases: sarcopenia, cachexia, various types of cancer, including lung, colon and ovarian cancer, patients on long term ventilation assistance, diabetes, chronic obstructive pulmonary disorder, renal failure, cardiac failure, trauma and disorders of the peripheral nerves.

Follistatin polypeptide-induced increased muscle mass might also benefit those suffering from muscle wasting diseases. GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

5. Pharmaceutical Compositions

In certain embodiments, compounds (e.g., follistatin polypeptides) of the present invention are formulated with a pharmaceutically acceptable carrier. For example, a follistatin polypeptide can be administered alone or as a component of a pharmaceutical formulation (i.e., a therapeutic composition). The subject compounds may be formulated for administration in any convenient way for use in human or veterinary medicine.

In certain embodiments, the therapeutic method of the invention includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to a target tissue site (e.g., bone, cartilage, muscle, fat or neurons), for example, a site having tissue damage. Topical administration may be suitable for wound healing and tissue repair. Therapeutically useful agents other than the follistatin polypeptides, which may also optionally be included in the composition as described above, may alternatively or additionally, be administered simultaneously or sequentially with the subject compounds (e.g., follistatin polypeptides) in the methods of the invention.

In certain embodiments, compositions of the present invention may include a matrix capable of delivering one or more therapeutic compounds (e.g., follistatin polypeptides) to a target tissue site, providing a structure for the developing tissue and optimally capable of being resorbed into the body. For example, the matrix may provide slow release of the follistatin polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above-mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required. The ointments, pastes, creams and gels may contain, in addition to a subject compound of the invention (e.g., a follistatin polypeptide), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more follistatin polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

It is understood that the dosage regimen will be determined by the attending physician, considering various factors that modify the action of the subject compounds of the invention (e.g., follistatin polypeptides). The various factors will depend upon the disease to be treated.

In certain embodiments, the present invention also provides gene therapy for the in vivo production of follistatin polypeptides or other compounds disclosed herein. Such therapy would achieve its therapeutic effect by introduction of the follistatin polynucleotide sequences into cells or tissues having the disorders as listed above. Delivery of follistatin polynucleotide sequences can be achieved using a recombinant expression vector such as a chimeric virus or a colloidal dispersion system. Preferred for therapeutic delivery of follistatin polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the follistatin polynucleotide. In one preferred embodiment, the vector is targeted to bone, cartilage, muscle or neuron cells/tissues.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for follistatin polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

Exemplification

The invention now being generally described will be more readily understood by reference to the following examples, which are included merely for purposes of illustrating certain embodiments of the present invention. These examples are not intended to limit the invention.

Example 1: Generation of Follistatin-Fc Proteins

Follistatin (FST) is known to have complex pharmacokinetic behavior. The short form FST(288) is reported to be more effective at blocking ligands and binds to cell surfaces in part due to its unmasked heparin binding domain. FST (315) is thought to be less effective but less attracted to cell surfaces due to the acid rich C-terminal amino acid sequence, which neutralizes the heparin binding domain. In the literature, follistatin is generally reported as having systemic effects. Applicants sought to determine whether a follistatin construct could be designed that would tend to have effects in the tissue of administration (such as an injected muscle), and whether dimerization of follistatin would provide enhanced tissue retention. The Fc domains of immunoglobulins are known to form dimers. To explore the effects of follistatin-Fc fusion proteins on muscle and other tissues, and to evaluate the effects of Fc-mediated dimerization on the pharmacokinetic properties of follistatin polypeptides, Applicants generated fusion proteins containing FST(288) or FST(315) fused to an Fc portion of an IgG1. A TGGG linker sequence was selected to join each follistatin polypeptide to the Fc portion.

For each FST-IgG1 construct, the following three leader sequences were considered:

```
(1) Follistatin leader:
                                      (SEQ ID NO: 23)
MVRARHQPGGLCLLLLLLCQFMEDRSAQA (2) Tissue plasminogen activator (TPA):
                                      (SEQ ID NO: 24)
MDAMKRGLCCVLLLCGAVFVSP (3) Honey bee melittin (HBML):
                                      (SEQ ID NO: 25)
MKFLVNVALVFMVVYISYIYA
```

The selected FST-Fc proteins incorporate the follistatin leader. The FST(288)-IgG1 fusion has the unprocessed and mature amino acid sequences shown below.

```
Unprocessed FST(288)-IgG1
                                      (SEQ ID NO: 26)
MVRARHQPGGLCLLLLLLCQFMEDRSAQAGNCWLRQAKNGRCQVLYKTEL

SKEECCSTGRLSTSWTEEDVNDNTLFKWMIFNGGAPNCIPCKETCENVDC

GPGKKCRMNKKNKPRCVCAPDCSNITWKGPVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECAMKEA

ACSSGVLLEVKHSGSCNTGGGTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK
```

```
Mature FST(288)-IgG1
                                      (SEQ ID NO: 27)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNTGGGTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHE

ALHNHYTQKSLSLSPGK
```

The initial "GN" sequence may be removed, yielding the following polypeptide. (SEQ ID NO: 28)

```
CWLRQAKNGRCQVLYKTELSKEECCSTGRLSTSWTEEDVNDNTLFKWMIF

NGGAPNCIPCKETCENVDCGPGKKCRMNKKNKPRCVCAPDCSNITWKGPV

CGLDGKTYRNECALLKARCKEQPELEVQYQGRCKKTCRDVFCPGSSTCVV

DQTNNAYCVTCNRICPEPASSEQYLCGNDGVTYSSACHLRKATCLLGRSI

GLAYEGKCIKAKSCEDIQCTGGKKCLWDFKVGRGRCSLCDELCPDSKSDE

PVCASDNATYASECAMKEAACSSGVLLEVKHSGSCNTGGGTHTCPPCPAP

ELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEAL

HNHYTQKSLSLSPGK
```

The FST(315)-IgG1 fusion has the unprocessed and mature amino acid sequences shown below.

```
Unprocessed FST(315)-IgG1
                                      (SEQ ID NO: 29)
MVRARHQPGGLCLLLLLLCQFMEDRSAQAGNCWLRQAKNGRCQVLYKTEL

SKEECCSTGRLSTSWTEEDVNDNTLFKWMIFNGGAPNCIPCKETCENVDC

GPGKKCRMNKKNKPRCVCAPDCSNITWKGPVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECAMKEA

ACSSGVLLEVKHSGSCNSISEDTEEEEEDEDQDYSFPISSILEWTGGGTH

TCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVS

NKALPAPIEKTISKAKGQPREPQVYTLPPSREEMTKNQVSLTCLVKGFYP

SDIAVEWESNGQPENNYKTTPPVLDSDGSFFLYSKLTVDKSRWQQGNVFS

CSVMHEALHNHYTQKSLSLSPGK
```

```
Mature FST(315)-IgG1
                                      (SEQ ID NO: 30)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS
```

-continued
DEPVCASDNATYASECAMKEAACSSGVLLEVKHSGSCNSISEDTEEEEED

EDQDYSFPISSILEWTGGGTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK

The initial "GN" sequence may be removed, yielding the following polypeptide. (SEQ ID NO: 31)

CWLRQAKNGRCQVLYKTELSKEECCSTGRLSTSWTEEDVNDNTLFKWMIF

NGGAPNCIPCKETCENVDCGPGKKCRMNKKNKPRCVCAPDCSNITWKGPV

CGLDGKTYRNECALLKARCKEQPELEVQYQGRCKKTCRDVFCPGSSTCVV

DQTNNAYCVTCNRICPEPASSEQYLCGNDGVTYSSACHLRKATCLLGRSI

GLAYEGKCIKAKSCEDIQCTGGKKCLWDFKVGRGRCSLCDELCPDSKSDE

PVCASDNATYASECAMKEAACSSGVLLEVKHSGSCNSISEDTEEEEEDED

QDYSFPISSILEWTGGGTHTCPPCPAPELLGGPSVFLFPPKPKDTLMISR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFF

LYSKLTVDKSRWQQGNVFSCSVMHEALHNHYTQKSLSLSPGK

Proteins were expressed in HEK-293 cells or CHO cells and purified from conditioned media by filtration and protein A chromatography. In some instances anion exchange and hydrophobic interaction chromatography and/or gel filtration was also used.

Protein activity was assessed by binding to activin A or GDF11. In each case, the proteins bind with a $K_D$ of less than 10 pM.

Example 2: The Effect of Systemic Administration of Follistatin-Fc Proteins on Muscle Mass and Strength in Mice Applicants determined the ability of follistatin-Fc proteins to increase muscle mass and strength in wild-type mice after systemic administration. An ActRIIB-Fc fusion protein that is well-known to stimulate substantial whole-body increases in lean muscle mass was used as a positive control.

Figure 2:
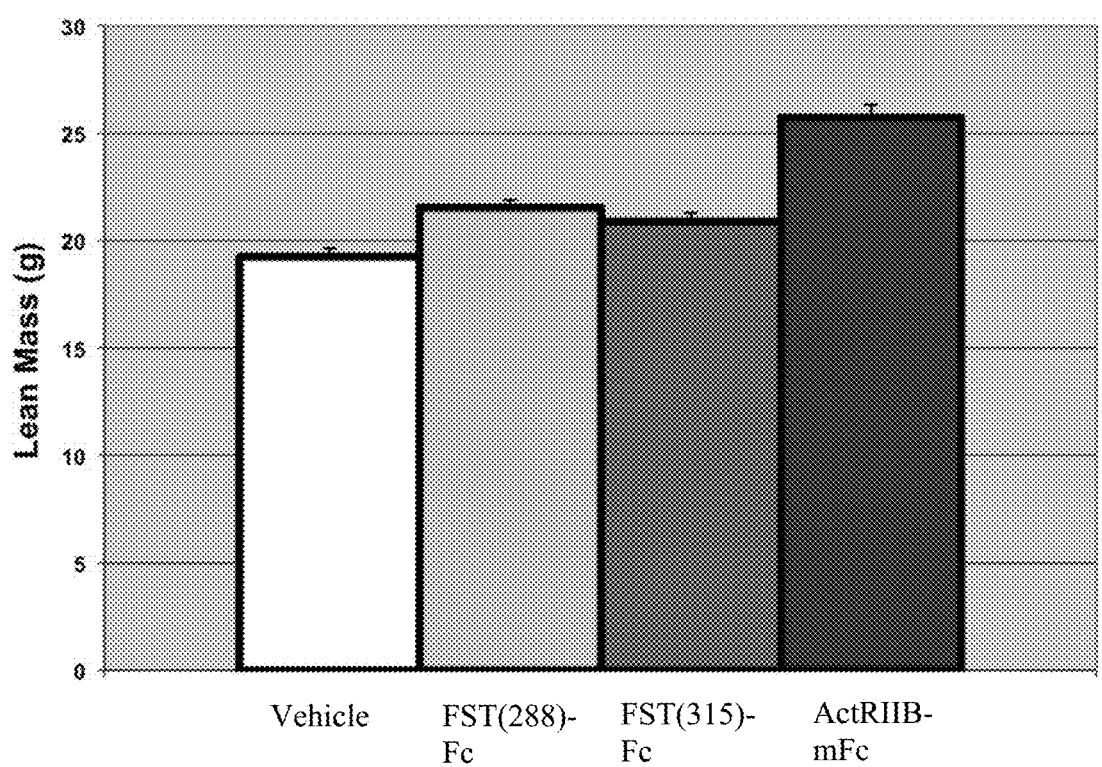
FIG. 2 shows the effect of 4 weeks treatment, by subcutaneous injection, with either FST(288)-Fc, FST(315)-Fc, or ActRIIB-Fc on lean tissue mass in mice. Vehicle was Tris-buffered saline. Data are means±SEM. *, P<0.05 vs. TBS by unpaired t-test. #, P<0.05 vs. FST groups by unpaired t-test. FST(288)-Fc, FST(315)-Fc, and ActRIIB-Fc treatment resulted in significant increases in lean tissue mass compared to vehicle control mice. The increase in lean tissue mass of ActRIIB-Fc treated mice was significantly greater than the increases in lean tissue mass observed in either FST(288)-Fc or FST(315)-Fc treated mice.
Figure 4:
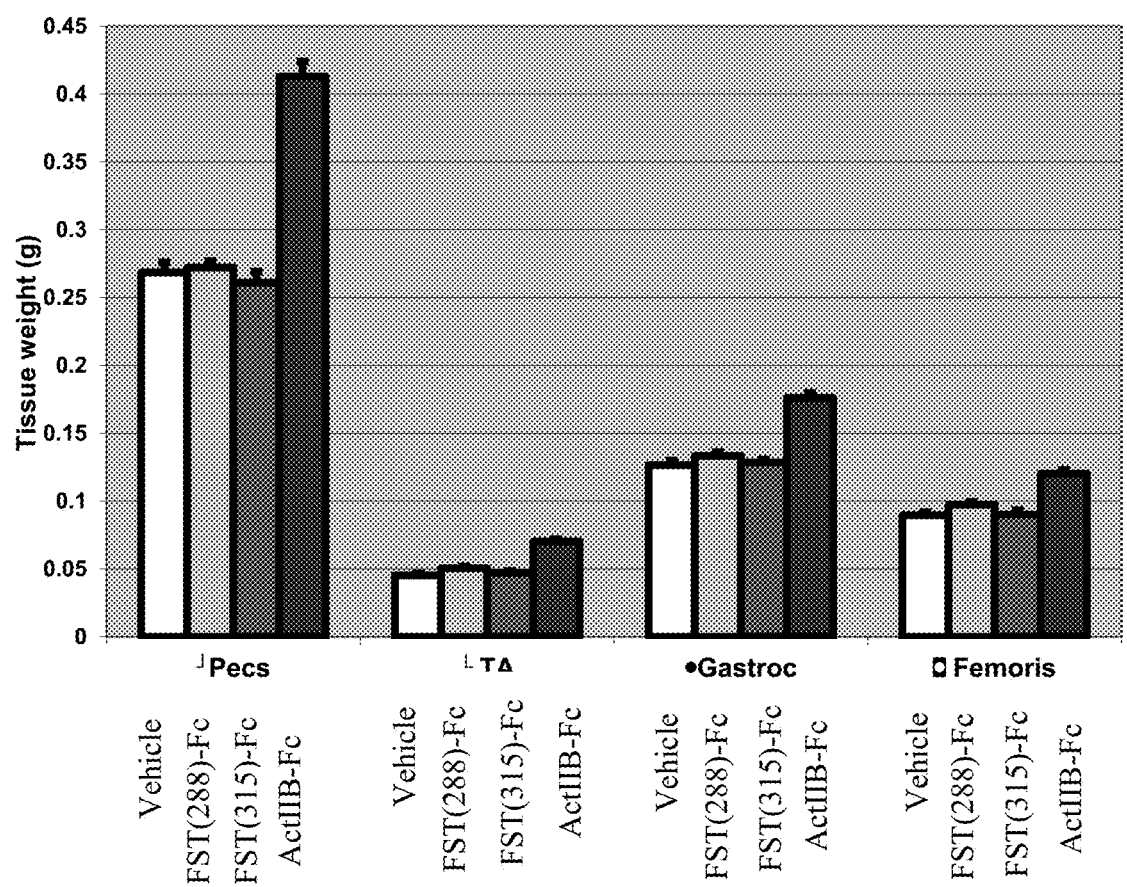
FIG. 4 shows the effect of 4 weeks treatment, by subcutaneous injection twice per week, with either FST(288)-IgG1, FST(315)-IgG1, or ActRIIB-Fc on pectoralis (Pecs), tibialis anterior (TA), gastrocnemius (Gastroc), and femoris muscle mass in mice. Vehicle was Tris-buffered saline. Data are means±SEM. *, P<0.05 vs. TBS by unpaired t-test. #, P<0.05 vs. FST groups by unpaired t-test. ActRIIB-Fc treatment significantly increased pectoralis, tibialis anterior, gastrocnemius, and femoris muscle mass in mice, but little to no increase in muscle mass was observed in FST(288)-IgG1 or FST(315)-IgG1 treated mice.

C57BL/6 mice were dosed (10 mg/kg; subcutaneously (s.c.)) twice/week for four weeks with the FST(288)-IgG1 protein, the human FST(315)-IgG1 protein, or the human ActRIIB-Fc protein. Mice were subjected to whole-body nuclear magnetic resonance (NMR) scanning to determine the percent change of whole body lean tissue mass. ActRIIB-Fc treated mice exhibited a significant (approximately 35%) increase in lean tissue when compared to the vehicle-control group. Mice treated with either the FST(288)-IgG1 or FST(315)-IgG1 protein exhibited little increase in lean tissue mass compared to the control cohort. See FIG. 2. At the end of the study, pectoralis, tibialis anterior (TA), gastrocnemius, and femoris muscles were dissected and weighed. As shown in FIG. 4, ActRIIB-Fc treatment significantly increased muscle mass in each of these muscle groups. In contrast, little to no increase in muscle mass was observed in either the FST(288)-IgG1 or FST(315)-IgG1 treatment groups. See FIG. 2.

Figure 3:
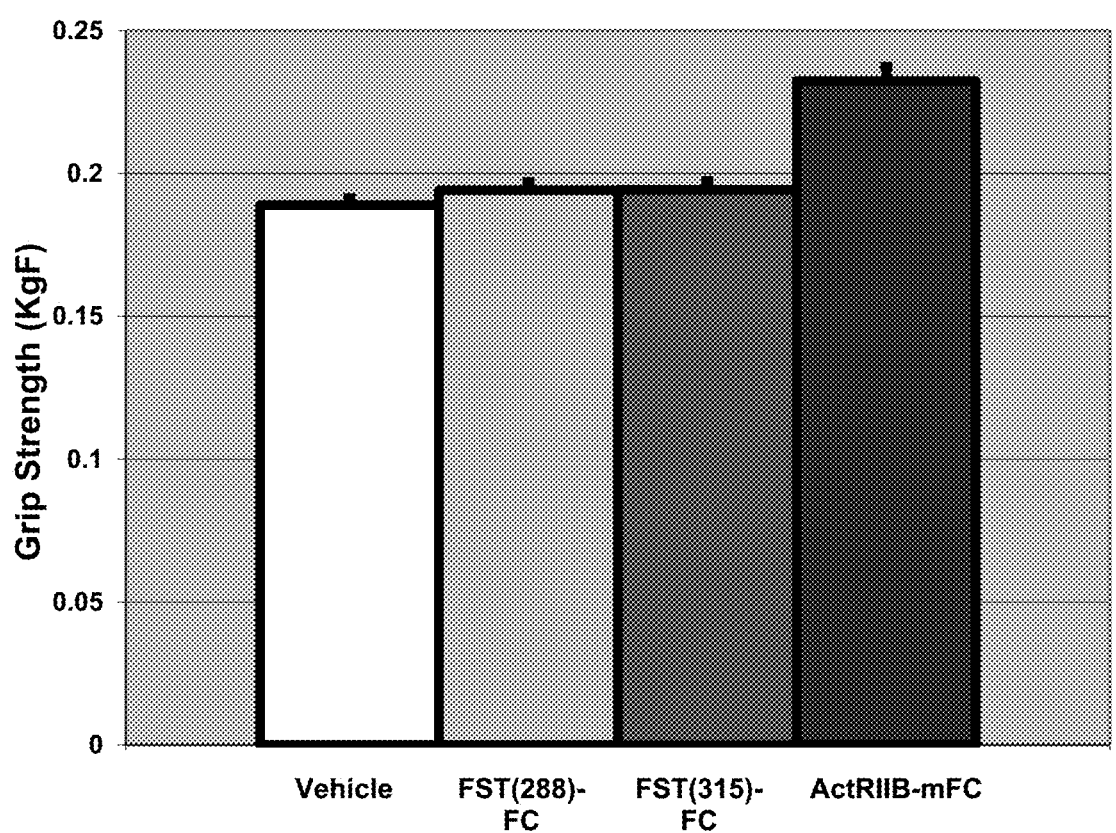
FIG. 3 shows the effect of 4 weeks treatment, by subcutaneous injection twice per week, with either FST(288)-Fc, FST(315)-Fc, or ActRIIB-Fc on grip strength in mice. Vehicle was Tris-buffered saline. Data are means±SEM. *, P<0.05 vs. TBS by unpaired t-test. #, P<0.05 vs. FST groups by unpaired t-test. ActRIIB-Fc treatment increased grip strength in mice. No increased grip strength was observed in FST(288)-Fc or FST(315)-Fc treated mice.

During the course of this study, mice were also examined for changes in muscle strength. The force a mouse exerts when pulling a force transducer is measured to determine forelimb grip strength. Applicants observed that mice treated with the ActRIIB-Fc protein exhibited increased muscle strength. In contrast, there was no increase in grip strength observed in either the FST(288)-IgG1 or FST(315)-IgG1 treatment groups. See FIG. 3.

Together, the results confirm that systemic administration of ActRIIB-Fc profoundly increases both muscle mass and strength in mice when compared to vehicle-control animals. In contrast, there was little to no increase in muscle mass or strength observed in mice treated with either the follistatin-Fc fusion protein FST(288)-IgG1 or FST(315)-IgG1. Therefore, it appears that follistatin-Fc fusions proteins have little or no effect on muscle mass or strength in vivo when administered systemically.

Example 3: The Effect of Systemic Administration of Follistatin-Fc Proteins on FSH Levels Follistatin is primarily characterized for its ability to bind and inhibit members of the TGF-beta superfamily of signaling proteins. In particular, follistatin is known to be a potent inhibitor of activin activity. Activin is a potent inducer of follicle-stimulating hormone (FSH) production. FSH is synthesized and secreted by gonadotrophs of the anterior pituitary gland and regulates growth and development during pubertal maturation and various reproductive processes in the body. To assess systemic effects of follistatin-Fc polypeptides, effects on FSH levels were evaluated.

Figure 5:
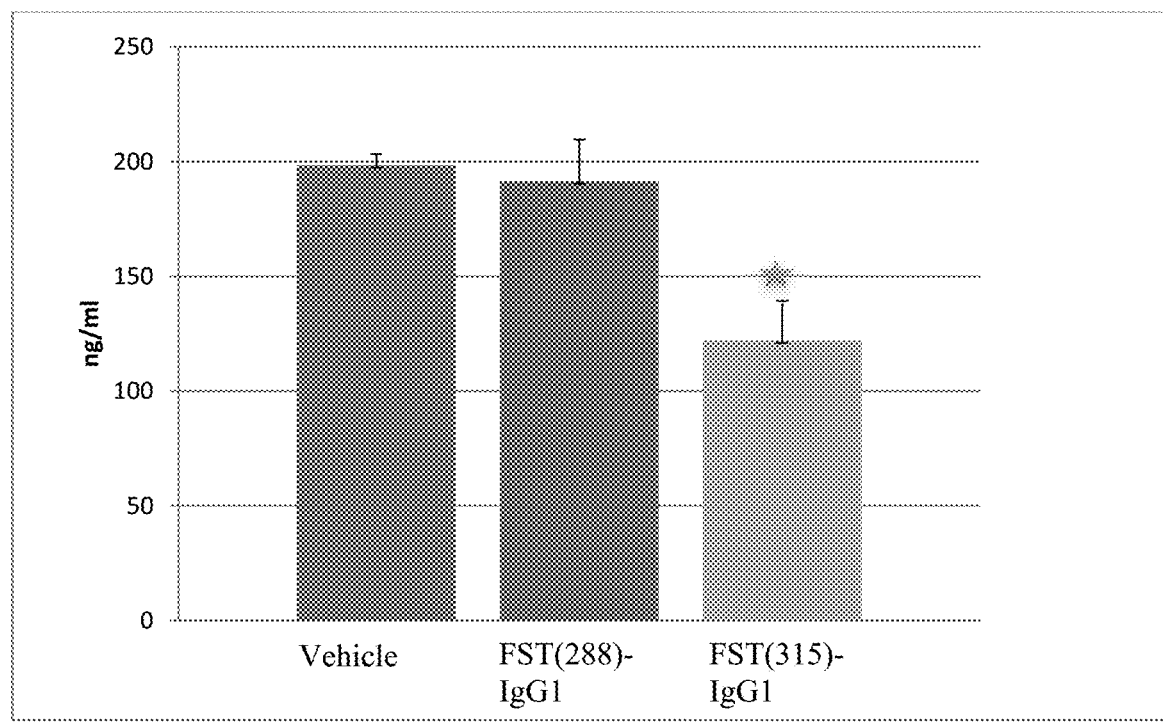
FIG. 5 shows the effect of 4 weeks treatment, by subcutaneous injection, with either FST(288)-IgG1 or FST(315)-IgG1 on serum levels of follicle-stimulating hormone (FSH). Vehicle was Tris-buffered saline. Data are means±SEM. *, P<0.05 vs. TBS by unpaired t-test. FST(315)-IgG1 treatment resulted in a significant decrease in serum FSH levels in comparison to vehicle control mice. In contrast, FST(288)-IgG1 treatment had no effect on serum FSH levels

Treatment (10 mg/kg; subcutaneously (s.c.) twice/week) with FST(288)-IgG1 resulted in circulating levels of the drug at 3.836 (±5.22) µg/mL. Similar treatment with FST (315)-IgG1 resulted in substantially higher serum levels of the drug at 19.31 (±1.85) µg/mL. As indicated in FIG. 5, FST(288)-IgG1 did not have any significant effects on serum levels of FSH, suggesting that this FST(288)-IgG1 treatment regime does not significantly affect systemic activin activity. In contrast, FST(315)-IgG1 treatment resulted in a decrease in circulating levels of FSH, indicating that systemic administration of FST(315)-IgG1 has an effect on systemic activin signaling. Overall, these data indicate that use of a follistatin polypeptide with an unmasked heparin binding domain, fused to an Fc domain that mediates dimerization, such as FST(288)-IgG1 results in a protein that has little or no systemic activity, while an FST(315)-IgG1, with a masked heparin binding domain, may be used to achieve systemic effects.

Example 4: The Effect of Local Administration of Follistatin-Fc Proteins on Muscle Mass and Strength in Mice While there were no significant effects after systemic administration, Applicants used a similar experimental approach to determine if follistatin can be used to locally increase muscle mass and strength in wild-type mice after intramuscular (i.m.) administration.

Figure 6:
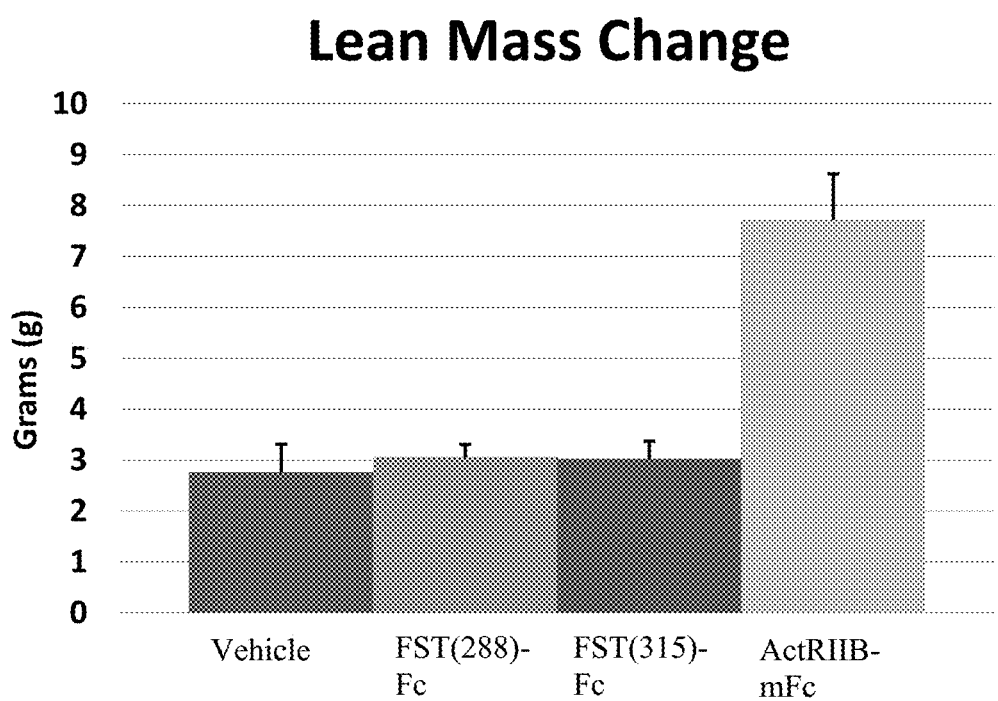
FIG. 6 shows the effect of 4 weeks treatment, by subcutaneous injection twice weekly, with either FST(288)-IgG1, FST(315)-IgG1, or ActRIIB-mFc on lean tissue mass in mice. Vehicle was Tris-buffered saline. Data are means±SEM. *, P<0.05 vs. TBS by unpaired t-test. ActRIIB-mFc treatment resulted in significant increases in lean tissue mass compared to vehicle control mice. No increases in lean tissue mass were observed in either FST (288)-IgG1 or FST(315)-IgG1 treated mice.
Figure 7:
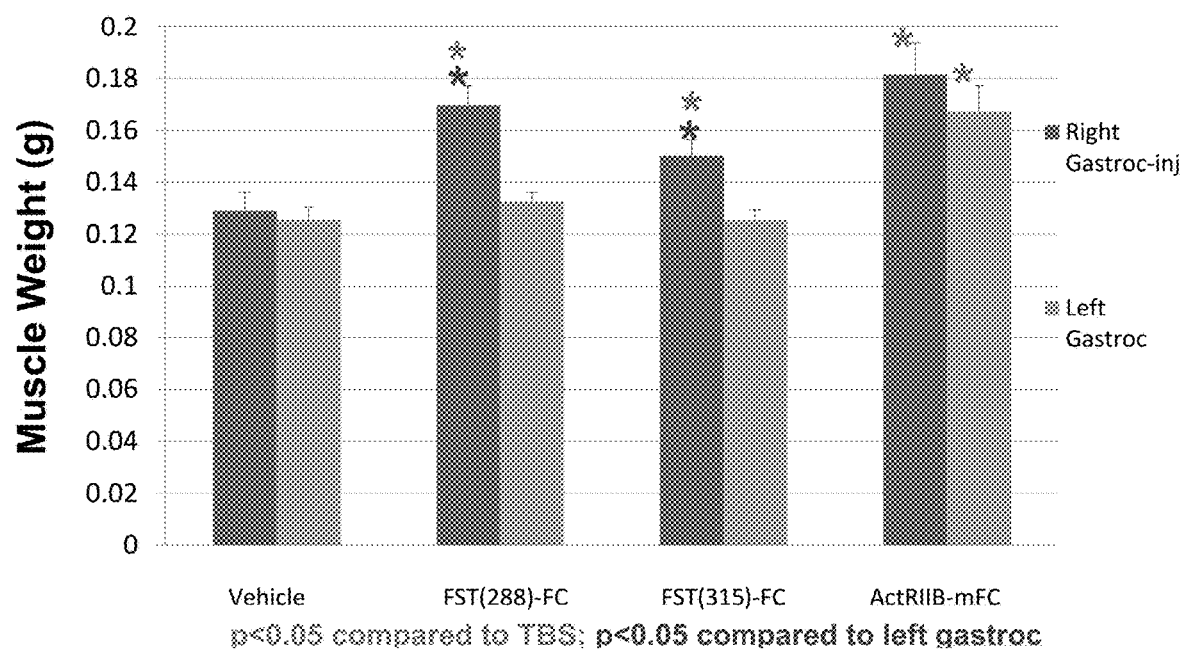
FIG. 7 shows the effect of 4 weeks treatment, by intramuscular injection into the right gastrocnemius twice weekly, with either FST(288)-IgG1, FST(315)-IgG1, or ActRIIB-mFc on gastrocnemius muscle mass in mice. Vehicle was Tris-buffered saline. Data are means±SEM. *, P<0.05 vs. TBS by unpaired t-test. #, P<0.05 right, injected gastocnemius muscle vs. left, non-injected, gastrocnemius muscle by unpaired t-test. FST(288)-IgG1, FST(315)-IgG1, and ActRIIB-mFc treatment significantly increased muscle mass in the right, injected gastrocnemius muscle. ActRIIB-mFc treatment also significantly increased muscle mass in the left, non-injected gastrocnemius muscle. In contrast, there was not observed increase in the left, non-injected gastocnemius muscle in FST(288)-IgG1 or FST(315)-IgG1 treated mice.

C57BL/6 mice were dosed (50 micrograms; i.m. into the right gastrocnemius muscle) twice/week for four weeks with the FST(288)-Fc protein, the FST(315)-Fc protein, or the human ActRIIB-Fc protein. At various time points after initial treatment, mice were subjected to whole-body nuclear magnetic resonance (NMR) scanning to determine the percent change of whole body lean tissue mass. ActRIIB-Fc treated mice exhibited a significant increase in lean tissue when compared to the vehicle-control group. In contrast, neither mice treated with the FST(288)-Fc nor FST(315)-Fc protein exhibited a significant increase in lean tissue mass compared to the control cohort. At the end of the study, both the right, injected gastrocnemius muscle and the left, contralateral gastrocnemius muscle were dissected and weighed. As shown in FIG. 6, ActRIIB-Fc treatment significantly increased muscle mass in both the right and left gastrocnemius muscles in comparison to vehicle-treated mice. Therefore, ActRIIB-Fc has systemic effects on increasing muscle mass even when restricted to local administration in a single muscle. In contrast, both FST(288)-Fc and FST(315)-Fc resulted in significant increases in muscle mass of the right gastrocnemius muscle but had no effect on the mass of the contralateral muscle. Therefore, contrary the effects observed after systemic administration, it appears that follistatin protein is a potent stimulator of muscle mass when directly administered into a muscle. Furthermore, follistatin appears to have a distinct advantage over other agents like ActRIIB-Fc in that its effects on muscle mass are localized to the site of administration, indicating that follistatin can be used for targeted therapy of a selected muscle, or muscle groups, without affecting the normal growth/activity of surrounding, non-targeted muscles.

Applicants also closely monitored the serum levels of follistatin-Fc fusion protein after i.m. administration. Treatment with FST(288)-IgG1 resulted in a circulating levels of the drug at 0.156 (±0.245) µg/mL. Similar treatment with FST(315)-IgG1 resulted in slightly higher serum levels of the drug at 3.58 (±1.73) µg/mL, but these levels were substantially lower than those observed after systemic administration of FST(315)-IgG1. As both FST(288)-IgG1 and FST(315)-IgG1 circulate in patient serum at lower levels after i.m. injection than is observed after systemic administration of FST(288)-IgG1 (i.e., 3.836 (±5.22) µg/mL), neither FST(288)-IgG1 nor FST(315)-IgG1 would be expected to have significant effects on serum levels of FSH as FST(288)-IgG1 had no such effect after s.c. administration. See FIG. 5. Accordingly, these data indicate that both FST(288)-IgG1 and FST(315)-IgG1 would be particularly well-suited for promoting targeted muscle growth in patients that are reproductively active or have a desire to minimize effects on the reproductive system.

Figure 8:
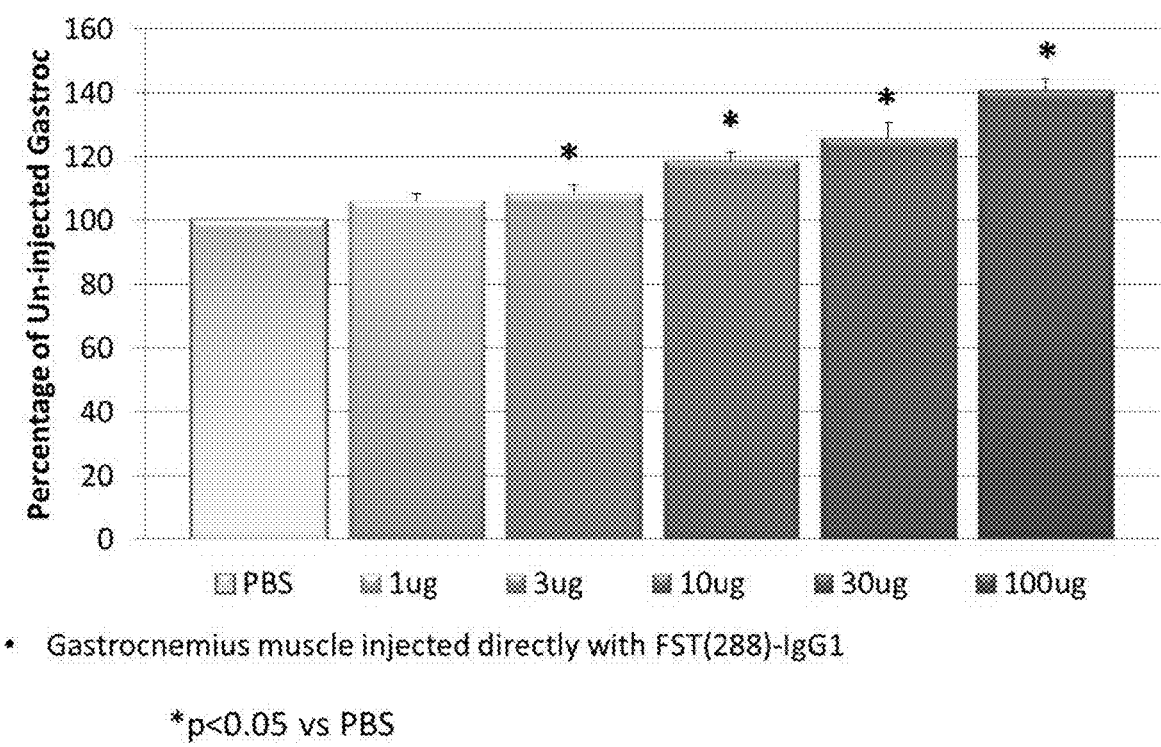
FIG. 8 shows the effect of 3 weeks treatment, by intramuscular injection into the right gastrocnemius twice weekly, with varying doses of FST(288)-IgG1, on gastrocnemius muscle mass in mice, expressed as a ratio over the uninjected, left gastrocnemius. Vehicle was phosphate-buffered saline. Data are means±SEM. *, P<0.05 vs. PBS by unpaired t-test. Increasing doses of FST(288)-IgG1 caused an increasing hypertrophy of the injected gastocnemius muscle relative to the uninjected muscle.

A similar experiment was conducted to establish a dose-response curve of the effects of FST(288)-IgG1 on muscle mass and quality. C57BL/6 mice were dosed with varying amounts (1 to 100 micrograms); i.m. into the right gastrocnemius muscle twice/week for four weeks. As shown in FIG. 8, the selective increase in the muscle mass of the injected muscle versus the contralateral muscle was greater with greater doses of FST(288)-IgG1. Muscle cross sections revealed the enhanced muscle mass to be the result of muscle fiber hypertrophy, rather than hypoplasia.

Example 5: Fc Optimization of Locally-Acting Follistatin-Fc Fusion Proteins

As described in the preceding Examples, follistatin-Fc fusion proteins such as FST(288)-IgG1 and FST(315)-IgG1 have poor systemic effects on muscle and other tissues, and particularly FST(288) forms of the protein are active at the site of injection. Applicants and others established that FST(288) binds to cells by virtue of the heparin binding domain and this binding can be eliminated by exogenous heparin. As a consequence, Applicants determined that immunoglobulin domains known to mediate CDC and ADCC effects on targeted cells may cause damage to cells treated with the heparin-binding follistatin constructs. Such damage could manifest as an immune reaction in the targeted tissue or in decreased growth of the targeted tissue. Therefore Applicants generated versions of follistatin polypeptides employing the Fc portion of human IgG2, which is an example of an IgG constant domain that is known to have diminished capability to stimulate CDC and ADCC activity. This experiment was conducted to ascertain whether follistatin-Fc fusion proteins using alternative Fc domains would retain activity.

Applicants generated fusion proteins containing FST (288) or FST(315) fused to an Fc portion of an IgG2. A TGGG linker sequence was selected to join each follistatin polypeptide to the Fc portion.

For each FST-IgG2 construct, the follistatin leader was employed.

The FST(288)-IgG2 fusion has the unprocessed and mature amino acid sequences shown below.

Unprocessed FST(288)-IgG2
(SEQ ID NO: 32)

MVRARHQPGGLCLLLLLLCQFMEDRSAQAGNCWLRQAKNGRCQVLYKTEL

SKEECCSTGRLSTSWTEEDVNDNTLFKWMIFNGGAPNCIPCKETCENVDC

GPGKKCRMNKKNKPRCVCAPDCSNITWKGPVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECAMKEA

ACSSGVLLEVKHSGSCNTGGGVECPPCPAPPVAGPSVFLFPPKPKDTLMI

SRTPEVTCVVVDVSHEDPEVQFNWYVDGVEVHNAKTKPREEQFNSTFRVV

SVLTVVHQDWLNGKEYKCKVSNKGLPAPIEKTISKTKGQPREPQVYTLPP

SREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

Which is encoded by the following nucleic acid sequence (SEQ ID NO:44)

```
atggtccgcgcgaggcaccagccgggtgggctttgcctcctgctgctgct gctctgccagttcatggaggaccgcagtgcccaggctgggaactgctggc tccgtcaagcgaagaacggccgctgccaggtcctgtacaagaccgaactg agcaaggaggagtgctgcagcaccggccggctgagcacctcgtggaccga ggaggacgtgaatgacaacacactcttcaagtggatgattttcaacgggg gcgcccccaactgcatccctgtaaagaaacgtgtgagaacgtggactgt ggacctgggaaaaaatgccgaatgaacaagaagaacaaacccgctgcgt ctgcgccccggattgttccaacatcacctggaagggtccagtctgcgggc tggatgggaaaacctaccgcaatgaatgtgcactcctaaaggcaagatgt aaagagcagccagaactggaagtccagtaccaaggcagatgtaaaaagac ttgtcgggatgttttctgtccaggcagctccacatgtgtggtggaccaga ccaataatgcctactgtgtgacctgtaatcggatttgcccagagcctgct tcctctgagcaatatctctgtgggaatgatggagtcacctactccagtgc ctgccacctgagaaaggctacctgcctgctgggcagatctattggattag
```

-continued
```
cctatgagggaaagtgtatcaaagcaaagtcctgtgaagatatccagtgc actggtgggaaaaaatgtttatgggatttcaaggttgggagaggccggtg ttccctctgtgatgagctgtgccctgacagtaagtcggatgagcctgtct gtgccagtgacaatgccacttatgccagcgagtgtgccatgaaggaagct gcctgctcctcaggtgtgctactggaagtaaagcactccggatcttgcaa caccggtggtggagtcgagtgcccaccgtgcccagcaccacctgtggcag gaccgtcagtcttcctcttccccccaaaacccaaggacaccctcatgatc tcccggacccctgaggtcacgtgcgtggtggtggacgtgagccacgaaga ccccgaggtccagttcaactggtacgtggacggcgtggaggtgcataatg ccaagacaaagccacgggaggagcagttcaacagcacgttccgtgtggtc agcgtcctcaccgtcgtgcaccaggactggctgaacggcaaggagtacaa gtgcaaggtctccaacaaaggcctcccagcccccatcgagaaaaccatct ccaaaaccaaagggcagccccgagaaccacaggtgtacaccctgccccca tcccgggaggagatgaccaagaaccaggtcagcctgacctgcctggtcaa aggcttctaccccagcgacatcgccgtggagtgggagagcaatgggcagc cggagaacaactacaagaccacacctcccatgctggactccgacggctcc ttcttcctctacagcaagctcaccgtggacaagagcaggtggcagcaggg gaacgtcttctcatgctccgtgatgcatgaggctctgcacaaccactaca cgcagaagagcctctccctgtctccgggtaaatgagaattc
```

Mature FST(288)-IgG2
(SEQ ID NO: 33)
```
GNCWLRQAKNGRCQVLYKTELSKEECCSTGRLSTSWTEEDVNDNTLFKWM
IFNGGAPNCIPCKETCENVDCGPGKKCRMNKKNKPRCVCAPDCSNITWKG
PVCGLDGKTYRNECALLKARCKEQPELEVQYQGRCKKTCRDVFCPGSSTC
VVDQTNNAYCVTCNRICPEPASSEQYLCGNDGVTYSSACHLRKATCLLGR
SIGLAYEGKCIKAKSCEDIQCTGGKKCLWDFKVGRGRCSLCDELCPDSKS
DEPVCASDNATYASECAMKEAACSSGVLLEVKHSGSCNTGGGVECPPCPA
PPVAGPSVFLFPPKPKDTLMISRTPEVTCVVVDVSHEDPEVQFNWYVDGV
EVHNAKTKPREEQFNSTFRVVSVLTVVHQDWLNGKEYKCKVSNKGLPAPI
EKTISKTKGQPREPQVYTLPPSREEMTKNQVSLTCLVKGFYPSDIAVEWE
SNGQPENNYKTTPPMLDSDGSFFLYSKLTVDKSRWQQGNVFSCSVMHEAL
HNHYTQKSLSLSPGK
```

The initial "GN" sequence may be removed, yielding the following polypeptide. (SEQ ID NO: 34)

```
CWLRQAKNGRCQVLYKTELSKEECCSTGRLSTSWTEEDVNDNTLFKWMIF
NGGAPNCIPCKETCENVDCGPGKKCRMNKKNKPRCVCAPDCSNITWKGPV
CGLDGKTYRNECALLKARCKEQPELEVQYQGRCKKTCRDVFCPGSSTCVV
DQTNNAYCVTCNRICPEPASSEQYLCGNDGVTYSSACHLRKATCLLGRSI
GLAYEGKCIKAKSCEDIQCTGGKKCLWDFKVGRGRCSLCDELCPDSKSDE
PVCASDNATYASECAMKEAACSSGVLLEVKHSGSCNTGGGVECPPCPAPP
```

-continued
```
VAGPSVFLFPPKPKDTLMISRTPEVTCVVVDVSHEDPEVQFNWYVDGVEV
HNAKTKPREEQFNSTFRVVSVLTVVHQDWLNGKEYKCKVSNKGLPAPIEK
TISKTKGQPREPQVYTLPPSREEMTKNQVSLTCLVKGFYPSDIAVEWESN
GQPENNYKTTPPMLDSDGSFFLYSKLTVDKSRWQQGNVFSCSVMHEALHN
HYTQKSLSLSPGK
```

The FST(315)-IgG2 fusion has the unprocessed and mature amino acid sequences shown below.

Unprocessed FST(315)-IgG2
(SEQ ID NO: 35)
```
MVRARHQPGGLCLLLLLLCQFMEDRSAQAGNCWLRQAKNGRCQVLYKTEL
SKEECCSTGRLSTSWTEEDVNDNTLFKWMIFNGGAPNCIPCKETCENVDC
GPGKKCRMNKKNKPRCVCAPDCSNITWKGPVCGLDGKTYRNECALLKARC
KEQPELEVQYQGRCKKTCRDVFCPGSSTCVVDQTNNAYCVTCNRICPEPA
SSEQYLCGNDGVTYSSACHLRKATCLLGRSIGLAYEGKCIKAKSCEDIQC
TGGKKCLWDFKVGRGRCSLCDELCPDSKSDEPVCASDNATYASECAMKEA
ACSSGVLLEVKHSGSCNSISEDTEEEEEDEDQDYSFPISSILEWTGGGVE
CPPCPAPPVAGPSVFLFPPKPKDTLMISRTPEVTCVVVDVSHEDPEVQFN
WYVDGVEVHNAKTKPREEQFNSTFRVVSVLTVVHQDWLNGKEYKCKVSNK
GLPAPIEKTISKTKGQPREPQVYTLPPSREEMTKNQVSLTCLVKGFYPSD
IAVEWESNGQPENNYKTTPPMLDSDGSFFLYSKLTVDKSRWQQGNVFSCS
VMHEALHNHYTQKSLSLSPGK
```

Which is encoded by the following nucleic acid sequence (SEQ ID NO:45)

```
atggtccgcgcgaggcaccagccgggtgggctttgcctcctgctgctgct gctctgccagttcatggaggaccgcagtgcccaggctgggaactgctggc tccgtcaagcgaagaacggccgctgccaggtcctgtacaagaccgaactg agcaaggaggagtgctgcagcaccggccggctgagcacctcgtggaccga ggaggacgtgaatgacaacacactcttcaagtggatgattttcaacgggg gtgcccccaactgcatccctgtaaagaaacgtgtgagaacgtggactgt ggacctgggaaaaaatgccgaatgaacaagaagaacaaaccccgctgcgt ctgcgccccggattgttccaacatcacctggaagggtccagtctgcgggc tggatgggaaaacctaccgcaatgaatgtgcactcctaaaggcaagatgt aaagagcagccagaactggaagtccagtaccaaggcagatgtaaaaagac ttgtcgggatgttttctgtccaggcagctccacatgtgtggtggaccaga ccaataatgcctactgtgtgacctgtaatcggatttgcccagagcctgct tcctctgagcaatatctctgtgggaatgatggagtcacctactccagtgc ctgccacctgagaaaggctacctgcctgctgggcagatctattggattag cctatgagggaaagtgtatcaaagcaaagtcctgtgaagatatccagtgc actggtgggaaaaaatgtttatgggatttcaaggttgggagaggccggtg ttccctctgtgatgagctgtgccctgacagtaagtcggatgagcctgtct gtgccagtgacaatgccacttatgccagcgagtgtgccatgaaggaagct
```

```
gcctgctcctcaggtgtgctactggaagtaaagcactccggatcttgcaa ctccatttcggaagacaccgaggaagaggaggaagatgaagaccaggact acagctttcctatatcttctattctagagtggaccggtggtggagtcgag tgccaccgtgcccagcaccacctgtggcaggaccgtcagtcttcctctt cccccaaaacccaaggacaccctcatgatctcccggaccctgaggtca cgtgcgtggtggtggacgtgagccacgaagaccccgaggtccagttcaac tggtacgtggacggcgtggaggtgcataatgccaagacaaagccacggga ggagcagttcaacagcacgttccgtgtggtcagcgtcctcaccgtcgtgc accaggactggctgaacggcaaggagtacaagtgcaaggtctccaacaaa ggcctcccagccccatcgagaaaaccatctccaaaaccaaagggcagcc ccgagaaccacaggtgtacaccctgcccccatcccgggaggagatgacca agaaccaggtcagcctgacctgcctggtcaaaggcttctaccccagcgac atcgccgtggagtgggagagcaatgggcagccggagaacaactacaagac cacacctcccatgctggactccgacggctccttcttcctctacagcaagc tcaccgtggacaagagcaggtggcagcaggggaacgtcttctcatgctcc gtgatgcatgaggctctgcacaaccactacacgcagaagagcctctccct gtctccgggtaaatgagaattc
```

Mature FST(315)-IgG2
(SEQ ID NO: 36)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEWTGGGVECPPCPAPPVAGPSVFLFPPKPKDTLMISR

TPEVTCVVVDVSHEDPEVQFNWYVDGVEVHNAKTKPREEQFNSTFRVVSV

LTVVHQDWLNGKEYKCKVSNKGLPAPIEKTISKTKGQPREPQVYTLPPSR

EEMTKNQVSLTCLVKGFYPSDIAVEWESNGQPENNYKTTPPMLDSDGSFF

LYSKLTVDKSRWQQGNVFSCSVMHEALHNHYTQKSLSLSPGK

The initial "GN" sequence may be removed, yielding the following polypeptide. (SEQ ID NO: 37)

CWLRQAKNGRCQVLYKTELSKEECCSTGRLSTSWTEEDVNDNTLFKWMIF

NGGAPNCIPCKETCENVDCGPGKKCRMNKKNKPRCVCAPDCSNITWKGPV

CGLDGKTYRNECALLKARCKEQPELEVQYQGRCKKTCRDVFCPGSSTCVV

DQTNNAYCVTCNRICPEPASSEQYLCGNDGVTYSSACHLRKATCLLGRSI

GLAYEGKCIKAKSCEDIQCTGGKKCLWDFKVGRGRCSLCDELCPDSKSDE

PVCASDNATYASECAMKEAACSSGVLLEVKHSGSCNSISEDTEEEEEDED

QDYSFPISSILEWTGGGVECPPCPAPPVAGPSVFLFPPKPKDTLMISRIP

EVTCVVVDVSHEDPEVQFNWYVDGVEVHNAKTKPREEQFNSTFRVVSVLT

VVHQDWLNGKEYKCKVSNKGLPAPIEKTISKIKGQPREPQVYTLPPSREE

MTKNQVSLTCLVKGFYPSDIAVEWESNGQPENNYKTTPPMLDSDGSFFLY

SKLTVDKSRWQQGNVFSCSVMHEALHNHYTQKSLSLSPGK

Proteins were expressed in HEK-293 cells or CHO cells and purified from conditioned media by filtration and protein A chromatography. In some instances anion exchange and hydrophobic interaction chromatography and/or gel filtration was also used.

Protein activity was assessed by binding to activin A or GDF11. In each case, the proteins bind with a $K_D$ of less than 10 pM. These data indicate that Follistatin-IgG2 fusion proteins can be generated and expressed and retain picomolar ligand binding activity.

Example 6: Optimized Locally-Acting Follistatin-Fc Fusion Proteins

To assess whether an optimal follistatin-Fc fusion protein could be generated, a variety of truncations between the C-terminus of FST(288) and FST(315) were generated. One of these truncations, ending at amino acid 291 and termed FST(291) showed superior expression properties compared to other forms and retained the desired heparin binding activity, despite containing a small portion of the masking domain of FST(315). This form was fused to the Fc portion of human IgG1 and IgG2 to generate FST(291)-IgG1 and FST(291)-IgG2.

A TGGG linker sequence was selected to join each follistatin polypeptide to the Fc portion.

For each FST-IgG1 construct, the follistatin leader was employed.

The FST(291)-IgG1 fusion has the unprocessed and mature amino acid sequences shown below.

Unprocessed FST(291)-IgG1
(SEQ ID NO: 38)
MVRARHQPGGLCLLLLLLCQFMEDRSAQAGNCWLRQAKNGRCQVLYKTEL

SKEECCSTGRLSTSWTEEDVNDNTLFKWMIFNGGAPNCIPCKETCENVDC

GPGKKCRMNKKNKPRCVCAPDCSNITWKGPVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECAMKEA

ACSSGVLLEVKHSGSCNSISTGGGTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

Mature FST(291)-IgG1
(SEQ ID NO: 39)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

-continued
VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISTGGGTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPGK

The initial "GN" sequence may be removed, yielding the following polypeptide. (SEQ ID NO: 40)

CWLRQAKNGRCQVLYKTELSKEECCSTGRLSTSWTEEDVNDNTLFKWMIF

NGGAPNCIPCKETCENVDCGPGKKCRMNKKNKPRCVCAPDCSNITWKGPV

CGLDGKTYRNECALLKARCKEQPELEVQYQGRCKKTCRDVFCPGSSTCVV

DQTNNAYCVTCNRICPEPASSEQYLCGNDGVTYSSACHLRKATCLLGRSI

GLAYEGKCIKAKSCEDIQCTGGKKCLWDFKVGRGRCSLCDELCPDSKSDE

PVCASDNATYASECAMKEAACSSGVLLEVKHSGSCNSISTGGGTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

The FST(291)-IgG2 fusion has the unprocessed and mature amino acid sequences shown below.

Unprocessed FST(291)-IgG2
(SEQ ID NO: 41)
MVRARHQPGGLCLLLLLLCQFMEDRSAQAGNCWLRQAKNGRCQVLYKTEL

SKEECCSTGRLSTSWTEEDVNDNTLFKWMIFNGGAPNCIPCKETCENVDC

GPGKKCRMNKKNKPRCVCAPDCSNITWKGPVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECAMKEA

ACSSGVLLEVKHSGSCNSISTGGGVECPPCPAPPVAGPSVFLFPPKPKDT

LMISRTPEVTCVVVDVSHEDPEVQFNWYVDGVEVHNAKTKPREEQFNSTF

RVVSVLTVVHQDWLNGKEYKCKVSNKGLPAPIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK

Mature FST(291)-IgG2
(SEQ ID NO: 42)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISTGGGVECPP

CPAPPVAGPSVFLFPPKPKDTLMISRTPEVTCVVVDVSHEDPEVQFNWYV

DGVEVHNAKTKPREEQFNSTFRVVSVLTVVHQDWLNGKEYKCKVSNKGLP

APIEKTISKTKGQPREPQVYTLPPSREEMTKNQVSLTCLVKGFYPSDIAV

EWESNGQPENNYKTTPPMLDSDGSFFLYSKLTVDKSRWQQGNVFSCSVMH

EALHNHYTQKSLSLSPGK

The initial "GN" sequence may be removed, yielding the following polypeptide. (SEQ ID NO: 43)

CWLRQAKNGRCQVLYKTELSKEECCSTGRLSTSWTEEDVNDNTLFKWMIF

NGGAPNCIPCKETCENVDCGPGKKCRMNKKNKPRCVCAPDCSNITWKGPV

CGLDGKTYRNECALLKARCKEQPELEVQYQGRCKKTCRDVFCPGSSTCVV

DQTNNAYCVTCNRICPEPASSEQYLCGNDGVTYSSACHLRKATCLLGRSI

GLAYEGKCIKAKSCEDIQCTGGKKCLWDFKVGRGRCSLCDELCPDSKSDE

PVCASDNATYASECAMKEAACSSGVLLEVKHSGSCNSISTGGGVECPPCP

APPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKGLPAP

IEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEA

LHNHYTQKSLSLSPGK

Proteins were expressed in HEK-293 cells or CHO cells and purified from conditioned media by filtration and protein A chromatography. In some instances anion exchange and hydrophobic interaction chromatography and/or gel filtration was also used.

Protein activity was assessed by binding to activin A or GDF11. In each case, the proteins bind with a $K_D$ of less than 10 pM.

Additional truncation experiments were conducted to identify Follistatin-IgG2 constructs, in the context of the TGGG linker, exhibiting an optimal ligand and heparin binding activity, so as to generate a polypeptide with high potency, a strong tendency towards retention in the treated tissue and low tendency to produce inflammatory or immune reaction in the treated tissue. For this purpose a series of constructs were generated, termed FST(278)-IgG2, FST(284)-IgG2, FST(291)-IgG2 and FST(303)-IgG2 and compared to each other and to FST(288)-IgG2 and FST-(315)-IgG2. Heparin binding was assessed by measuring protein recovery from cells in the presence or absence of heparin, quantitated by ELISA and expressed as a ratio of protein recovered in the presence of heparin to the protein recovered in the absence of heparin. As shown in the table below, FST(278)-IgG2, FST(284)-IgG2, FST(288)-IgG2 and FST(291)-IgG2 all show similar ratios of 3.00-4.00, while FST(303)-IgG2 and FST(315)-IgG2 show ratios of 1.50 and 0.97, respectively. This indicates that as more amino acids are included between position 291 and 303, the heparin binding activity is sharply reduced.

Heparin Binding of FST-IgG2 Truncations

| FST-IgG2 Construct | Ratio (protein recovered with heparin/protein recovered without heparin) |
|---|---|
| FST(278)-IgG2 | 4.18 |
| FST(284)-IgG2 | 3.54 |
| FST(288)-IgG2 | 3.34 |
| FST(291)-IgG2 | 3.00 |
| FST(303)-IgG2 | 1.50 |
| FST(315)-IgG2 | 0.97 |

Cell-based reporter gene assays (A-204 Reporter Gene Assay, described in WO/2006/012627) to assess inhibition of activin and GDF11 were conducted. As shown in the table below, constructs extending beyond position 288 provided enhanced ligand inhibition.

Ligand Inhibition of FST-IgG2 Truncations

| FST-IgG2 Construct | IC50 (ng/ml) Activin A | IC50 (ng/ml) GDF-11 |
|---|---|---|
| FST(278)-IgG2 | 521 | 91 |
| FST(284)-IgG2 | 369 | 123 |
| FST(288)-IgG2 | 30 | 41 |
| FST(291)-IgG2 | 20 | 26 |
| FST(303)-IgG2 | 2 | 18 |
| FST(315)-IgG2 | 10 | 15 |

Taking together the heparin binding and ligand inhibition data, it is apparent that FST-IgG2 constructs, in the context of the TGGG linker used here, or similar sized linkers (e.g., linkers sized 1-10 amino acids, optionally 3-8 amino acids), that end at position 291-302 will have enhanced ligand inhibition relative to FST(288)-IgG2 and enhanced heparin binding relative to FST(315)-IgG2, and that FST(291)-IgG2 represents an optimal protein for local administration and effect.

Example 7: The Effect of Local Administration of FST(291)-IgG2 Protein on Muscle Mass and Strength in Mice Applicants assessed the activity of the optimized FST (291)-IgG2 protein as used to locally increase muscle mass and strength in wild-type mice after intramuscular (i.m.) administration.

Figure 9:
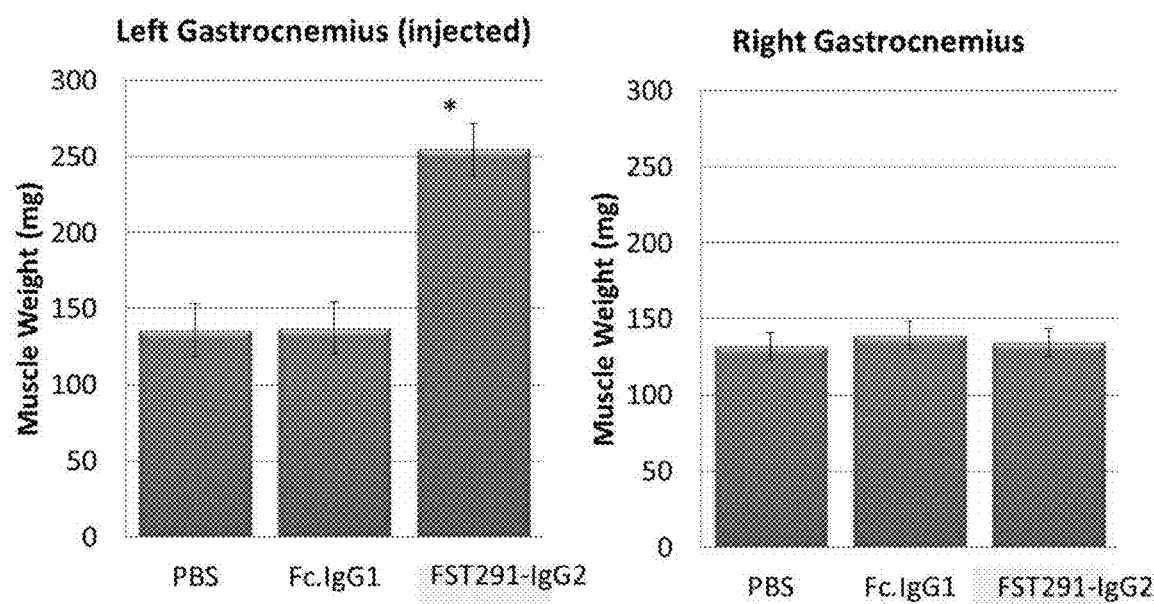
FIG. 9 shows the effect of 4 weeks treatment, by intramuscular injection into the left gastrocnemius twice weekly, with FST(291)-IgG1. Vehicle was phosphate-buffered saline. Data are means±SEM. *, P<0.05 vs. PBS by unpaired t-test. Intramuscular administration of FST(291)-IgG2 caused marked increase in muscle mass in the injected gastocnemius muscle relative to the uninjected muscle and relative to controls.

C57BL/6 mice were dosed (100 micrograms in 50 microliters; i.m. into the left gastrocnemius muscle) twice/week for four weeks with vehicle (PBS), FST(291)-IgG2 or a control Fc from IgG1. At the end of the study, both the left, injected gastrocnemius muscle and the right, contralateral gastrocnemius muscle were dissected and weighed. As shown in FIG. 9, FST(291)-IgG2 treatment significantly increased muscle mass in the injected left gastrocnemius muscles, to a remarkable degree, in comparison to vehicle-treated mice, with no effect observed on the contralateral muscle. Additionally, pectoral and femoris muscles were weighed and showed no change as a consequence of vehicle or FST(291)-IgG2 administration. Therefore, FST(291)-IgG2 has restricted effect on the injected muscle group with little or no systemic effect. Similar experiments have been conducted but injecting different muscle groups, including the triceps and the tibialis anterior. In each case, selective hypertrophy of the injected muscle was observed.

Additional experiments were conducted to directly compare the effects of FST(288)-IgG1 and FST(291)-IgG2 on muscle growth. While both constructs promoted significant increased muscle mass in the injected muscle (gastrocnemius), the FST(291)-IgG2 caused approximately a 42% increase in the injected muscle versus the contralateral muscle, while FST(288)-IgG1 caused approximately a 22% increase in injected muscle versus the contralateral muscle.

Accordingly, these data indicate that FST(291)-IgG2 is an optimal compound for promoting targeted muscle growth in patients in need thereof.

Example 8: The Effect of Local Administration of FST(291)-IgG2 Protein on Muscle in a Mouse Model of Duchenne Muscular Dystrophy The effect of FST(291)-IgG2 on muscle mass was assessed in a mouse model of Duchenne muscular dystrophy. The C57BL/10ScCN-Dmd$^{mdx}$/J (mdx) strain of mice is a well-established model of human Duchenne muscular dystrophy (Bulfield, Siller et al. 1984; Partridge 2013).

Two separate studies were performed with mdx mice and the wild-type background strain, C57BL/10SnJ (WT). In the first study, treatment (either FST(291)-IgG2 or vehicle control) was initiated when mice reached 6 weeks of age. In the second study, treatment was initiated when mice reached 4 weeks of age. In both studies, mice received 100 μg FST (291)-IgG2 intramuscularly into the left gastrocnemius muscle, twice per week, in a fixed volume of 50 μL per injection. Four-week old mice were treated for 4 weeks, and 6-week old mice were treated for 6 weeks.

At necropsy the gastrocnemius muscles from the injected (left) and contralateral, non-injected (right) leg were excised and weighed. In both studies the injected gastrocnemius muscles from WT animals treated with FST(291)-IgG2 were significantly greater in size compared to the contralateral legs as well as the vehicle controls (P<0.001). In both studies, the gastrocnemius muscle treated with FST(291)-IgG2 was significantly greater in size, normalized to body weight, compared to the contralateral muscle and to vehicle-treated animals, in both WT and mdx mice. The increase in muscle mass was somewhat more pronounced in younger animals than in older animals. In terms of percent increase relative to the contralateral muscle, FST(291)-IgG2 increased muscle mass by 34.2% and 16.4% in 6-week old WT and mdx mice, respectively. Muscle mass increases of 62.8% and 41.8% were observed in 4-week old WT and mdx mice, respectively.

These data demonstrate that blocking activin/myostatin signaling using twice per week intramuscular FST(291)-IgG2 administration increases muscle mass in a mouse model of a muscular dystrophy. The increase in muscle mass occurs locally in the injected muscle only.

Example 9: The Effect of Local Administration of FST(291)-IgG2 Protein on Muscle in a Mouse Model of ALS The effect of FST(291)-IgG2 on muscle mass and strength was assessed in a mouse model of ALS. The B6.Cg-Tg (SOD1*G93A)1Gur/J (SOD1) strain of mice is a well-established model of human ALS (Wooley C M. et al. (2005) Muscle Nerve 32(1):43-50).

Twelve week old SOD1 mice and wild-type background strain B6 (WT) mice received treatment with 100 μg of FST(291)-IgG2 or vehicle control intramuscularly into the right tibialis anterior (TA) muscle, twice per week. After 4 weeks, mice were anesthetized and the TA muscle was prepared for physiological analysis, after which the injected and uninjected muscles were weighed and then processed for histological analysis. Physiological strength analysis was performed by fixing the distal TA tendon to a lever arm of a dual mode muscle lever system and inserting platinum needle electrodes behind the knee to stimulate the peroneal nerve.

In WT animals, FST(291)-IgG2 treatment increased TA muscle mass by 75% compared to the non-injected contralateral TA. The adjacent extensor digitorum longus (EDL) was also increased in mass by 118% compared to the non-injected contralateral EDL. SOD1 mice displayed approximately 50% less mass than WT mice. FST(291)-IgG2 treatment increased TA muscle mass by 35% and EDL muscle mass 32% compared to the non-injected contralateral muscles.

In physiological strength tests of TA muscle, SOD1 mice displayed a deficit in strength compared to WT mice. TA muscle from vehicle control treated SOD1 mice had a peak tetanic force of only 18% of the WT vehicle control treated TA muscle. In WT mice, FST(291)-IgG2 treatment increased the peak tetanic force of the TA by 36% compared to vehicle control treated WT mice. Moreover, there was a 72% increase in peak tetanic force of the TA from FST(291)-IgG2 treated SOD1 mice compared to vehicle control treated SOD1 mice.

These results demonstrate that FST(291)-IgG2 treatment can effectively increase muscle mass and strength locally following direct injection into target muscles in both normal and neurogenic muscles. SOD1 mice lose 50% of the muscle mass and 82% of the peak tetanic force in their TA compared to wild type B6 mice. FST(291)-IgG2 increased both muscle mass (35%) and peak tetanic force (72%) in SOD1 mice. These data demonstrate that FST(291)-IgG2 is a promising treatment for focal myopathies and can improve muscle function in neurogenic diseases such as ALS.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method of treating Duchenne Muscular Dystrophy (DMD) in a patient, the method comprising:
   administering an effective amount of a follistatin polypeptide by an intramuscular route of administration to a targeted muscle of a patient in need thereof;
   wherein the follistatin fusion protein comprises a first amino acid sequence and a second amino acid sequence, wherein the first amino acid sequence comprises an amino acid sequence that is at least 90% identical to SEQ ID NO: 15 or 16, wherein the first amino acid sequence ends at the amino acid corresponding to any one of amino acids 291-302 of SEQ ID NO: 4, and wherein the second amino acid sequence comprises a constant domain of an immunoglobulin G (IgG).

2. The method of claim 1, wherein administration of the effective amount increases muscle mass in a targeted muscle of the patient.

3. The method of claim 2, wherein the targeted muscle is damaged, weakened or deficient.

4. The method of claim 2, wherein the targeted muscle is healthy but an increase in muscle size or strength of the targeted muscle is desired.

5. The method of claim 1, wherein the follistatin polypeptide does not have a substantial systemic effect on muscle mass of the patient.

6. The method of claim 1, wherein the follistatin polypeptide binds to one or more ligands selected from the group consisting of: myostatin, growth differentiation factor 11 (GDF-11), activin A and activin B with a dissociation constant ($K_D$) less than 1 nM, 100 pM, 50 pM or 10 pM.

7. The method of claim 6, wherein the follistatin polypeptide comprises an unmasked heparin binding domain.

8. The method of claim 7, wherein the follistatin polypeptide forms a dimer.

9. The method of claim 8, wherein the follistatin polypeptide comprises an Fc portion of an IgG.

10. The method of claim 9, wherein the IgG is selected from the group consisting of: IgG1, IgG2, IgG4 and an IgG2/4 hybrid.

11. The method of claim 10, wherein the follistatin polypeptide comprises an amino acid sequence that is at least 90%, 91%, 92%, 93%, 94%, 95%, 96%, 97%, 98%, 99% or 100% identical to the amino acid sequence of SEQ ID NO: 43.

12. The method of claim 11, wherein the follistatin polypeptide comprises the amino acid sequence of SEQ ID NO: 43.

13. The method of claim 11, wherein the follistatin polypeptide comprises the amino acid sequence of SEQ ID NO: 43 with the final (carboxy-terminal) lysine (K) of SEQ ID NO: 43 being absent.

14. The method of claim 10, wherein the follistatin polypeptide comprises an amino acid sequence that is at least 90%, 91%, 92%, 93%, 94%, 95%, 96%, 97%, 98%, 99% or 100% identical to the amino acid sequence of SEQ ID NO: 42.

15. The method of claim 14, wherein the follistatin polypeptide comprises the amino acid sequence of SEQ ID NO: 42.

16. The method of claim 14, wherein the follistatin polypeptide comprises the amino acid sequence of SEQ ID NO: 42 with the final (carboxy-terminal) lysine (K) of SEQ ID NO: 42 being absent.

17. The method of claim 10, wherein the follistatin polypeptide comprises a first amino acid sequence derived from follistatin that consists of an amino acid sequence at least 91%, 92%, 93%, 94%, 95%, 96%, 97%, 98%, 99% or 100% identical to SEQ ID NO: 15 or 16.

18. The method of claim 17, wherein the follistatin polypeptide comprises the amino acid sequence of SEQ ID NO: 15.

19. The method of claim 17, wherein the follistatin polypeptide comprises the amino acid sequence of SEQ ID NO: 16.

20. The method of claim 17, wherein the method causes no substantial effect in the patient on a measure selected from the group consisting of: serum follicle-stimulating hormone (FSH) levels, liver size, hematocrit and reticulocyte levels.

* * * * *

SEQUENCE LISTING

```
<160> NUMBER OF SEQ ID NOS: 47

<210> SEQ ID NO 1
<211> LENGTH: 317
<212> TYPE: PRT
<213> ORGANISM: Homo sapiens

<400> SEQUENCE: 1

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
```

```
                180             185                 190
Asn Arg Ile Cys Pro Glu Pro Ala Ser Ser Glu Gln Tyr Leu Cys Gly
            195                 200                 205
Asn Asp Gly Val Thr Tyr Ser Ser Ala Cys His Leu Arg Lys Ala Thr
            210                 215                 220
Cys Leu Leu Gly Arg Ser Ile Gly Leu Ala Tyr Glu Gly Lys Cys Ile
225                 230                 235                 240
Lys Ala Lys Ser Cys Glu Asp Ile Gln Cys Thr Gly Gly Lys Lys Cys
                245                 250                 255
Leu Trp Asp Phe Lys Val Gly Arg Gly Arg Cys Ser Leu Cys Asp Glu
            260                 265                 270
Leu Cys Pro Asp Ser Lys Ser Asp Glu Pro Val Cys Ala Ser Asp Asn
            275                 280                 285
Ala Thr Tyr Ala Ser Glu Cys Ala Met Lys Ala Ala Cys Ser Ser
            290                 295                 300
Gly Val Leu Leu Glu Val Lys His Ser Gly Ser Cys Asn
305                 310                 315

<210> SEQ ID NO 2
<211> LENGTH: 288
<212> TYPE: PRT
<213> ORGANISM: Homo sapiens

<400> SEQUENCE: 2

Gly Asn Cys Trp Leu Arg Gln Ala Lys Asn Gly Arg Cys Gln Val Leu
1               5                   10                  15
Tyr Lys Thr Glu Leu Ser Lys Glu Glu Cys Cys Ser Thr Gly Arg Leu
                20                  25                  30
Ser Thr Ser Trp Thr Glu Glu Asp Val Asn Asp Asn Thr Leu Phe Lys
            35                  40                  45
Trp Met Ile Phe Asn Gly Gly Ala Pro Asn Cys Ile Pro Cys Lys Glu
        50                  55                  60
Thr Cys Glu Asn Val Asp Cys Gly Pro Gly Lys Lys Cys Arg Met Asn
65                  70                  75                  80
Lys Lys Asn Lys Pro Arg Cys Val Cys Ala Pro Asp Cys Ser Asn Ile
                85                  90                  95
Thr Trp Lys Gly Pro Val Cys Gly Leu Asp Gly Lys Thr Tyr Arg Asn
            100                 105                 110
Glu Cys Ala Leu Leu Lys Ala Arg Cys Lys Glu Gln Pro Glu Leu Glu
        115                 120                 125
Val Gln Tyr Gln Gly Arg Cys Lys Lys Thr Cys Arg Asp Val Phe Cys
    130                 135                 140
Pro Gly Ser Ser Thr Cys Val Val Asp Gln Thr Asn Asn Ala Tyr Cys
145                 150                 155                 160
Val Thr Cys Asn Arg Ile Cys Pro Glu Pro Ala Ser Ser Glu Gln Tyr
                165                 170                 175
Leu Cys Gly Asn Asp Gly Val Thr Tyr Ser Ser Ala Cys His Leu Arg
            180                 185                 190
Lys Ala Thr Cys Leu Leu Gly Arg Ser Ile Gly Leu Ala Tyr Glu Gly
        195                 200                 205
Lys Cys Ile Lys Ala Lys Ser Cys Glu Asp Ile Gln Cys Thr Gly Gly
    210                 215                 220
Lys Lys Cys Leu Trp Asp Phe Lys Val Gly Arg Gly Arg Cys Ser Leu
225                 230                 235                 240
```

```
Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

<210> SEQ ID NO 3
<211> LENGTH: 344
<212> TYPE: PRT
<213> ORGANISM: Homo sapiens

<400> SEQUENCE: 3

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335
```

```
Pro Ile Ser Ser Ile Leu Glu Trp
                340

<210> SEQ ID NO 4
<211> LENGTH: 315
<212> TYPE: PRT
<213> ORGANISM: Homo sapiens

<400> SEQUENCE: 4

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Asp Glu Asp Gln Asp
    290                 295                 300

Tyr Ser Phe Pro Ile Ser Ser Ile Leu Glu Trp
305                 310                 315

<210> SEQ ID NO 5
<211> LENGTH: 12
<212> TYPE: PRT
<213> ORGANISM: Homo sapiens

<400> SEQUENCE: 5
```

```
Lys Lys Cys Arg Met Asn Lys Asn Lys Pro Arg
1               5                   10
```

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any basic amino acid, particularly Lys or Arg
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any basic amino acid, particularly Lys or Arg
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (7)..(8)
<223> OTHER INFORMATION: Any basic amino acid, particularly Lys or Arg
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any basic amino acid, particularly Lys or Arg
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any basic amino acid, particularly Lys or Arg

<400> SEQUENCE: 6

```
Xaa Xaa Xaa Xaa Xaa Xaa Xaa Xaa Xaa Xaa Xaa Xaa
1               5                   10
```

<210> SEQ ID NO 7
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
                20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
    50                  55                  60

Thr
65
```

```
<210> SEQ ID NO 8
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr
    50                  55                  60

<210> SEQ ID NO 9
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Cys Glu Asn Val Asp Cys Gly Pro Gly Lys Lys Cys Arg Met Asn Lys
1               5                   10                  15

Lys Asn Lys Pro Arg Cys Val Cys Ala Pro Asp Cys Ser Asn Ile Thr
            20                  25                  30

Trp Lys Gly Pro Val Cys Gly Leu Asp Gly Lys Thr Tyr Arg Asn Glu
        35                  40                  45

Cys Ala Leu Leu Lys Ala Arg Cys Lys Glu Gln Pro Glu Leu Glu Val
    50                  55                  60

Gln Tyr Gln Gly Arg Cys
65                  70

<210> SEQ ID NO 10
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95
```

-continued

```
Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys
    130

<210> SEQ ID NO 11
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Lys Lys Thr Cys Glu Asn Val Asp Cys Gly Pro
    130                 135                 140

Gly Lys Lys Cys Arg Met Asn Lys Lys Asn Lys Pro Arg Cys Val Cys
145                 150                 155                 160

Ala Pro Asp Cys Ser Asn Ile Thr Trp Lys Gly Pro Val Cys Gly Leu
                165                 170                 175

Asp Gly Lys Thr Tyr Arg Asn Glu Cys Ala Leu Leu Lys Ala Arg Cys
            180                 185                 190

Lys Glu Gln Pro Glu Leu Glu Val Gln Tyr Gln Gly Arg Cys
        195                 200                 205

<210> SEQ ID NO 12
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Cys Glu Asn Val Asp Cys Gly Pro Gly Lys Lys Cys Arg Met Asn Lys
1               5                   10                  15

Lys Asn Lys Pro Arg Cys Val Cys Ala Pro Asp Cys Ser Asn Ile Thr
            20                  25                  30

Trp Lys Gly Pro Val Cys Gly Leu Asp Gly Lys Thr Tyr Arg Asn Glu
        35                  40                  45
```

```
Cys Ala Leu Leu Lys Ala Arg Cys Lys Glu Gln Pro Glu Leu Glu Val
    50                  55                  60
Gln Tyr Gln Gly Arg Cys Lys Lys Thr Cys Arg Asp Val Phe Cys Pro
 65                  70                  75                  80
Gly Ser Ser Thr Cys Val Val Asp Gln Thr Asn Asn Ala Tyr Cys Val
                 85                  90                  95
Thr Cys Asn Arg Ile Cys Pro Glu Pro Ala Ser Ser Glu Gln Tyr Leu
            100                 105                 110
Cys Gly Asn Asp Gly Val Thr Tyr Ser Ser Ala Cys His Leu Arg Lys
            115                 120                 125
Ala Thr Cys Leu Leu Gly Arg Ser Ile Gly Leu Ala Tyr Glu Gly Lys
130                 135                 140
Cys
145

<210> SEQ ID NO 13
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Cys Trp Leu Arg Gln Ala Lys Asn Gly Arg Cys Gln Val Leu Tyr Lys
 1               5                  10                  15
Thr Glu Leu Ser Lys Glu Glu Cys Cys Ser Thr Gly Arg Leu Ser Thr
                20                  25                  30
Ser Trp Thr Glu Glu Asp Val Asn Asp Asn Thr Leu Phe Lys Trp Met
            35                  40                  45
Ile Phe Asn Gly Gly Ala Pro Asn Cys Ile Pro Cys Lys Glu Thr Cys
         50                  55                  60
Glu Asn Val Asp Cys Gly Pro Gly Lys Lys Cys Arg Met Asn Lys Lys
 65                  70                  75                  80
Asn Lys Pro Arg Cys Val Cys Ala Pro Asp Cys Ser Asn Ile Thr Trp
                 85                  90                  95
Lys Gly Pro Val Cys Gly Leu Asp Gly Lys Thr Tyr Arg Asn Glu Cys
            100                 105                 110
Ala Leu Leu Lys Ala Arg Cys Lys Glu Gln Pro Glu Leu Glu Val Gln
            115                 120                 125
Tyr Gln Gly Arg Cys Lys Lys Thr Cys Arg Asp Val Phe Cys Pro Gly
            130                 135                 140
Ser Ser Thr Cys Val Val Asp Gln Thr Asn Asn Ala Tyr Cys Val Thr
145                 150                 155                 160
Cys Asn Arg Ile Cys Pro Glu Pro Ala Ser Ser Glu Gln Tyr Leu Cys
                165                 170                 175
Gly Asn Asp Gly Val Thr Tyr Ser Ser Ala Cys His Leu Arg Lys Ala
            180                 185                 190
Thr Cys Leu Leu Gly Arg Ser Ile Gly Leu Ala Tyr Glu Gly Lys Cys
            195                 200                 205

<210> SEQ ID NO 14
<211> LENGTH: 320
<212> TYPE: PRT
<213> ORGANISM: Homo sapiens

<400> SEQUENCE: 14
```

Met Val Arg Ala Arg His Gln Pro Gly Gly Leu Cys Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
            195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
290                 295                 300

Gly Val Leu Leu Glu Val Lys His Ser Gly Ser Cys Asn Ser Ile Ser
305                 310                 315                 320

<210> SEQ ID NO 15
<211> LENGTH: 291
<212> TYPE: PRT
<213> ORGANISM: Homo sapiens

<400> SEQUENCE: 15

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser
    290

<210> SEQ ID NO 16
<211> LENGTH: 289
<212> TYPE: PRT
<213> ORGANISM: Homo sapiens

<400> SEQUENCE: 16

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Lys Lys Thr Cys Arg Asp Val Phe Cys Pro Gly

```
                130                 135                 140
Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
                165                 170                 175

Gly Asn Asp Gly Val Thr Tyr Ser Ser Ala Cys His Leu Arg Lys Ala
                180                 185                 190

Thr Cys Leu Leu Gly Arg Ser Ile Gly Leu Ala Tyr Glu Gly Lys Cys
                195                 200                 205

Ile Lys Ala Lys Ser Cys Glu Asp Ile Gln Cys Thr Gly Gly Lys Lys
                210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
                245                 250                 255

Asn Ala Thr Tyr Ala Ser Glu Cys Ala Met Lys Glu Ala Ala Cys Ser
                260                 265                 270

Ser Gly Val Leu Leu Glu Val Lys His Ser Gly Ser Cys Asn Ser Ile
                275                 280                 285

Ser
```

<210> SEQ ID NO 17
<211> LENGTH: 225
<212> TYPE: PRT
<213> ORGANISM: Homo sapiens

<400> SEQUENCE: 17

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
                35                  40                  45

Pro Glu Val Lys Phe Asn Trp Tyr Val Asp Gly Val Glu Val His Asn
50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
                115                 120                 125

Leu Pro Pro Ser Arg Glu Glu Met Thr Lys Asn Gln Val Ser Leu Thr
                130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
                180                 185                 190

Ser Arg Trp Gln Gln Gly Asn Val Phe Ser Cys Ser Val Met His Glu
                195                 200                 205

Ala Leu His Asn His Tyr Thr Gln Lys Ser Leu Ser Leu Ser Pro Gly
```

Lys
225

<210> SEQ ID NO 18
<211> LENGTH: 223
<212> TYPE: PRT
<213> ORGANISM: Homo sapiens

<400> SEQUENCE: 18

Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 19
<211> LENGTH: 1032
<212> TYPE: DNA
<213> ORGANISM: Homo sapiens

<400> SEQUENCE: 19
atggtccgcg cgaggcacca gccgggtggg ctttgcctcc tgctgctgct gctctgccag      60
ttcatggagg accgcagtgc ccaggctggg aactgctggc tccgtcaagc gaagaacggc     120
cgctgccagg tcctgtacaa gaccgaactg agcaaggagg agtgctgcag caccggccgg     180
ctgagcacct cgtggaccga ggaggacgtg aatgacaaca cactcttcaa gtggatgatt     240
ttcaacgggg gcgcccccaa ctgcatcccc tgtaaagaaa cgtgtgagaa cgtggactgt     300
ggacctggga aaaatgccg aatgaacaag aagaacaaac ccgctgcgt ctgcgccccg      360 gattgttcca acatcacctg gaagggtcca gtctgcgggc tggatgggaa aacctaccgc     420
aatgaatgtg cactcctaaa ggcaagatgt aaagagcagc cagaactgga agtccagtac     480

| | |
|---|---|
| caaggcagat gtaaaaagac ttgtcgggat gttttctgtc caggcagctc cacatgtgtg | 540 |
| gtggaccaga ccaataatgc ctactgtgtg acctgtaatc ggatttgccc agagcctgct | 600 |
| tcctctgagc aatatctctg tgggaatgat ggagtcacct actccagtgc ctgccacctg | 660 |
| agaaaggcta cctgcctgct gggcagatct attggattag cctatgaggg aaagtgtatc | 720 |
| aaagcaaagt cctgtgaaga tatccagtgc actggtggga aaaaatgttt atgggatttc | 780 |
| aaggttggga gaggccggtg ttccctctgt gatgagctgt gccctgacag taagtcggat | 840 |
| gagcctgtct gtgccagtga caatgccact tatgccagcg agtgtgccat gaaggaagct | 900 |
| gcctgctcct caggtgtgct actgaagta aagcactccg atcttgcaa ctccatttcg | 960 |
| gaagacaccg aggaagagga ggaagatgaa gaccaggact acagctttcc tatatcttct | 1020 |
| attctagagt gg | 1032 |

<210> SEQ ID NO 20
<211> LENGTH: 945
<212> TYPE: DNA
<213> ORGANISM: Homo sapiens

<400> SEQUENCE: 20

| | |
|---|---|
| gggaactgct ggctccgtca agcgaagaac ggccgctgcc aggtcctgta caagaccgaa | 60 |
| ctgagcaagg aggagtgctg cagcaccggc cggctgagca cctcgtggac cgaggaggac | 120 |
| gtgaatgaca acacactctt caagtggatg attttcaacg ggggcgcccc caactgcatc | 180 |
| ccctgtaaag aaacgtgtga gaacgtggac tgtggacctg ggaaaaaatg ccgaatgaac | 240 |
| aagaagaaca accccgctg cgtctgcgcc ccggattgtt ccaacatcac ctggaagggt | 300 |
| ccagtctgcg ggctggatgg gaaaaaccta cgcaatgaat gtgcactcct aaaggcaaga | 360 |
| tgtaaagagc agccagaact ggaagtccag taccaaggca gatgtaaaaa gacttgtcgg | 420 |
| gatgtttct gtccaggcag ctccacatgt gtggtggacc agaccaataa tgcctactgt | 480 |
| gtgacctgta atcggatttg cccagagcct gcttcctctg agcaatatct ctgtgggaat | 540 |
| gatggagtca cctactccag tgcctgccac ctgagaaagg ctacctgcct gctgggcaga | 600 |
| tctattggat tagcctatga gggaaagtgt atcaaagcaa agtcctgtga agatatccag | 660 |
| tgcactggtg ggaaaaaatg tttatgggat ttcaaggttg ggagaggccg tgttccctc | 720 |
| tgtgatgagc tgtgccctga cagtaagtcg gatgagcctg tctgtgccag tgacaatgcc | 780 |
| acttatgcca gcgagtgtgc catgaaggaa gctgcctgct cctcaggtgt gctactggaa | 840 |
| gtaaagcact ccggatcttg caactccatt tcggaagaca ccgaggaaga ggaggaagat | 900 |
| gaagaccagg actacagctt tcctatatct tctattctag agtgg | 945 |

<210> SEQ ID NO 21
<211> LENGTH: 864
<212> TYPE: DNA
<213> ORGANISM: Homo sapiens

<400> SEQUENCE: 21

| | |
|---|---|
| gggaactgct ggctccgtca agcgaagaac ggccgctgcc aggtcctgta caagaccgaa | 60 |
| ctgagcaagg aggagtgctg cagcaccggc cggctgagca cctcgtggac cgaggaggac | 120 |
| gtgaatgaca acacactctt caagtggatg attttcaacg ggggcgcccc caactgcatc | 180 |
| ccctgtaaag aaacgtgtga gaacgtggac tgtggacctg ggaaaaaatg ccgaatgaac | 240 |
| aagaagaaca accccgctg cgtctgcgcc ccggattgtt ccaacatcac ctggaagggt | 300 |
| ccagtctgcg ggctggatgg gaaaaaccta cgcaatgaat gtgcactcct aaaggcaaga | 360 |

```
tgtaaagagc agccagaact ggaagtccag taccaaggca gatgtaaaaa gacttgtcgg    420
gatgttttct gtccaggcag ctccacatgt gtggtggacc agaccaataa tgcctactgt    480
gtgacctgta atcggatttg cccagagcct gcttcctctg agcaatatct ctgtgggaat    540
gatggagtca cctactccag tgcctgccac ctgagaaagg ctacctgcct gctgggcaga    600
tctattggat tagcctatga gggaaagtgt atcaaagcaa agtcctgtga agatatccag    660
tgcactggtg gaaaaaatg tttatgggat ttcaaggttg ggagaggccg tgttccctc     720 tgtgatgagc tgtgccctga cagtaagtcg gatgagcctg tctgtgccag tgacaatgcc    780
acttatgcca gcgagtgtgc catgaaggaa gctgcctgct cctcaggtgt gctactggaa    840
gtaaagcact ccggatcttg caac                                           864
```

<210> SEQ ID NO 22
<211> LENGTH: 876
<212> TYPE: DNA
<213> ORGANISM: Homo sapiens

<400> SEQUENCE: 22

```
gggaactgct ggctccgtca agcgaagaac ggccgctgcc aggtcctgta caagaccgaa     60
ctgagcaagg aggagtgctg cagcaccggc cggctgagca cctcgtggac cgaggaggac    120
gtgaatgaca cacactcttt caagtggatg attttcaacg ggggcgcccc caactgcatc    180
ccctgtaaag aaacgtgtga aacgtggac tgtggacctg ggaaaaaatg ccgaatgaac    240
aagaagaaca acccccgctg cgtctgcgcc ccggattgtt ccaacatcac ctggaagggt    300
ccagtctgcg ggctggatgg gaaaacctac cgcaatgaat gtgcactcct aaaggcaaga    360
tgtaaagagc agccagaact ggaagtccag taccaaggca gatgtaaaaa gacttgtcgg    420
gatgttttct gtccaggcag ctccacatgt gtggtggacc agaccaataa tgcctactgt    480
gtgacctgta atcggatttg cccagagcct gcttcctctg agcaatatct ctgtgggaat    540
gatggagtca cctactccag tgcctgccac ctgagaaagg ctacctgcct gctgggcaga    600
tctattggat tagcctatga gggaaagtgt atcaaagcaa agtcctgtga agatatccag    660
tgcactggtg gaaaaaatg tttatgggat ttcaaggttg ggagaggccg tgttccctc     720 tgtgatgagc tgtgccctga cagtaagtcg gatgagcctg tctgtgccag tgacaatgcc    780
acttatgcca gcgagtgtgc catgaaggaa gctgcctgct cctcaggtgt gctactggaa    840
gtaaagcact ccggatcttg caactccatt tcgtgg                              876
```

<210> SEQ ID NO 23
<211> LENGTH: 29
<212> TYPE: PRT
<213> ORGANISM: Unknown
<220> FEATURE:
<223> OTHER INFORMATION: Description of Unknown:
      Follistatin leader sequence

<400> SEQUENCE: 23

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala
            20                  25

<210> SEQ ID NO 24
<211> LENGTH: 22
<212> TYPE: PRT
<213> ORGANISM: Unknown

```
<220> FEATURE:
<223> OTHER INFORMATION: Description of Unknown:
      Tissue plasminogen activator (TPA) sequence

<400> SEQUENCE: 24

Met Asp Ala Met Lys Arg Gly Leu Cys Cys Val Leu Leu Leu Cys Gly
1               5                   10                  15

Ala Val Phe Val Ser Pro
            20

<210> SEQ ID NO 25
<211> LENGTH: 21
<212> TYPE: PRT
<213> ORGANISM: Apis mellifera

<400> SEQUENCE: 25

Met Lys Phe Leu Val Asn Val Ala Leu Val Phe Met Val Val Tyr Ile
1               5                   10                  15

Ser Tyr Ile Tyr Ala
            20

<210> SEQ ID NO 26
<211> LENGTH: 546
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220
```

```
Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
            245                 250                 255

Leu Trp Asp Phe Lys Val Gly Arg Gly Arg Cys Ser Leu Cys Asp Glu
        260                 265                 270

Leu Cys Pro Asp Ser Lys Ser Asp Glu Pro Val Cys Ala Ser Asp Asn
    275                 280                 285

Ala Thr Tyr Ala Ser Glu Cys Ala Met Lys Glu Ala Ala Cys Ser Ser
290                 295                 300

Gly Val Leu Leu Glu Val Lys His Ser Gly Ser Cys Asn Thr Gly Gly
305                 310                 315                 320

Gly Thr His Thr Cys Pro Pro Cys Pro Ala Pro Glu Leu Leu Gly Gly
                325                 330                 335

Pro Ser Val Phe Leu Phe Pro Pro Lys Pro Lys Asp Thr Leu Met Ile
            340                 345                 350

Ser Arg Thr Pro Glu Val Thr Cys Val Val Val Asp Val Ser His Glu
        355                 360                 365

Asp Pro Glu Val Lys Phe Asn Trp Tyr Val Asp Gly Val Glu Val His
    370                 375                 380

Asn Ala Lys Thr Lys Pro Arg Glu Glu Gln Tyr Asn Ser Thr Tyr Arg
385                 390                 395                 400

Val Val Ser Val Leu Thr Val Leu His Gln Asp Trp Leu Asn Gly Lys
                405                 410                 415

Glu Tyr Lys Cys Lys Val Ser Asn Lys Ala Leu Pro Ala Pro Ile Glu
            420                 425                 430

Lys Thr Ile Ser Lys Ala Lys Gly Gln Pro Arg Glu Pro Gln Val Tyr
        435                 440                 445

Thr Leu Pro Pro Ser Arg Glu Glu Met Thr Lys Asn Gln Val Ser Leu
    450                 455                 460

Thr Cys Leu Val Lys Gly Phe Tyr Pro Ser Asp Ile Ala Val Glu Trp
465                 470                 475                 480

Glu Ser Asn Gly Gln Pro Glu Asn Asn Tyr Lys Thr Thr Pro Pro Val
                485                 490                 495

Leu Asp Ser Asp Gly Ser Phe Phe Leu Tyr Ser Lys Leu Thr Val Asp
            500                 505                 510

Lys Ser Arg Trp Gln Gln Gly Asn Val Phe Ser Cys Ser Val Met His
        515                 520                 525

Glu Ala Leu His Asn His Tyr Thr Gln Lys Ser Leu Ser Leu Ser Pro
    530                 535                 540

Gly Lys
545

<210> SEQ ID NO 27
<211> LENGTH: 517
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30
```

-continued

```
Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
 50                  55                  60

Thr Cys Glu Asn Val Asp Cys Gly Pro Gly Lys Lys Cys Arg Met Asn
 65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
               100                 105                 110

Glu Cys Ala Leu Leu Lys Ala Arg Cys Lys Glu Gln Pro Glu Leu Glu
               115                 120                 125

Val Gln Tyr Gln Gly Arg Cys Lys Lys Thr Cys Arg Asp Val Phe Cys
           130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
               180                 185                 190

Lys Ala Thr Cys Leu Leu Gly Arg Ser Ile Gly Leu Ala Tyr Glu Gly
           195                 200                 205

Lys Cys Ile Lys Ala Lys Ser Cys Glu Asp Ile Gln Cys Thr Gly Gly
   210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
               260                 265                 270

Cys Ser Ser Gly Val Leu Leu Glu Val Lys His Ser Gly Ser Cys Asn
   275                 280                 285

Thr Gly Gly Gly Thr His Thr Cys Pro Pro Cys Pro Ala Pro Glu Leu
   290                 295                 300

Leu Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
                325                 330                 335

Ser His Glu Asp Pro Glu Val Lys Phe Asn Trp Tyr Val Asp Gly Val
               340                 345                 350

Glu Val His Asn Ala Lys Thr Lys Pro Arg Glu Glu Gln Tyr Asn Ser
           355                 360                 365

Thr Tyr Arg Val Val Ser Val Leu Thr Val Leu His Gln Asp Trp Leu
   370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Ala Lys Gly Gln Pro Arg Glu Pro
                405                 410                 415

Gln Val Tyr Thr Leu Pro Pro Ser Arg Glu Glu Met Thr Lys Asn Gln
               420                 425                 430

Val Ser Leu Thr Cys Leu Val Lys Gly Phe Tyr Pro Ser Asp Ile Ala
           435                 440                 445
```

```
Val Glu Trp Glu Ser Asn Gly Gln Pro Glu Asn Asn Tyr Lys Thr Thr
    450                 455                 460

Pro Pro Val Leu Asp Ser Asp Gly Ser Phe Phe Leu Tyr Ser Lys Leu
465                 470                 475                 480

Thr Val Asp Lys Ser Arg Trp Gln Gln Gly Asn Val Phe Ser Cys Ser
                485                 490                 495

Val Met His Glu Ala Leu His Asn His Tyr Thr Gln Lys Ser Leu Ser
            500                 505                 510

Leu Ser Pro Gly Lys
        515

<210> SEQ ID NO 28
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
                20                  25                  30

Ser Trp Thr Glu Glu Asp Val Asn Asp Asn Thr Leu Phe Lys Trp Met
            35                  40                  45

Ile Phe Asn Gly Gly Ala Pro Asn Cys Ile Pro Cys Lys Glu Thr Cys
        50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
                100                 105                 110

Ala Leu Leu Lys Ala Arg Cys Lys Glu Gln Pro Glu Leu Glu Val Gln
            115                 120                 125

Tyr Gln Gly Arg Cys Lys Lys Thr Cys Arg Asp Val Phe Cys Pro Gly
        130                 135                 140

Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
                165                 170                 175

Gly Asn Asp Gly Val Thr Tyr Ser Ser Ala Cys His Leu Arg Lys Ala
                180                 185                 190

Thr Cys Leu Leu Gly Arg Ser Ile Gly Leu Ala Tyr Glu Gly Lys Cys
            195                 200                 205

Ile Lys Ala Lys Ser Cys Glu Asp Ile Gln Cys Thr Gly Gly Lys Lys
        210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
                245                 250                 255

Asn Ala Thr Tyr Ala Ser Glu Cys Ala Met Lys Glu Ala Ala Cys Ser
                260                 265                 270

Ser Gly Val Leu Leu Glu Val Lys His Ser Gly Ser Cys Asn Thr Gly
            275                 280                 285
```

```
Gly Gly Thr His Thr Cys Pro Pro Cys Pro Ala Pro Glu Leu Leu Gly
            290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
                325                 330                 335

Glu Asp Pro Glu Val Lys Phe Asn Trp Tyr Val Asp Gly Val Glu Val
                340                 345                 350

His Asn Ala Lys Thr Lys Pro Arg Glu Glu Gln Tyr Asn Ser Thr Tyr
            355                 360                 365

Arg Val Val Ser Val Leu Thr Val Leu His Gln Asp Trp Leu Asn Gly
370                 375                 380

Lys Glu Tyr Lys Cys Lys Val Ser Asn Lys Ala Leu Pro Ala Pro Ile
385                 390                 395                 400

Glu Lys Thr Ile Ser Lys Ala Lys Gly Gln Pro Arg Glu Pro Gln Val
                405                 410                 415

Tyr Thr Leu Pro Pro Ser Arg Glu Glu Met Thr Lys Asn Gln Val Ser
                420                 425                 430

Leu Thr Cys Leu Val Lys Gly Phe Tyr Pro Ser Asp Ile Ala Val Glu
            435                 440                 445

Trp Glu Ser Asn Gly Gln Pro Glu Asn Asn Tyr Lys Thr Thr Pro Pro
450                 455                 460

Val Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                485                 490                 495

His Glu Ala Leu His Asn His Tyr Thr Gln Lys Ser Leu Ser Leu Ser
            500                 505                 510

Pro Gly Lys
        515

<210> SEQ ID NO 29
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Val Arg Ala Arg His Gln Pro Gly Gly Leu Cys Leu Leu Leu
1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
        50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
                100                 105                 110

Lys Pro Arg Cys Val Cys Ala Pro Asp Cys Ser Asn Ile Thr Trp Lys
```

```
                115                 120                 125
Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp Thr Gly Gly Gly Thr His Thr Cys
            340                 345                 350

Pro Pro Cys Pro Ala Pro Glu Leu Leu Gly Gly Pro Ser Val Phe Leu
        355                 360                 365

Phe Pro Pro Lys Pro Lys Asp Thr Leu Met Ile Ser Arg Thr Pro Glu
    370                 375                 380

Val Thr Cys Val Val Val Asp Val Ser His Glu Asp Pro Glu Val Lys
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
            420                 425                 430

Thr Val Leu His Gln Asp Trp Leu Asn Gly Lys Glu Tyr Lys Cys Lys
        435                 440                 445

Val Ser Asn Lys Ala Leu Pro Ala Pro Ile Glu Lys Thr Ile Ser Lys
    450                 455                 460

Ala Lys Gly Gln Pro Arg Glu Pro Gln Val Tyr Thr Leu Pro Pro Ser
465                 470                 475                 480

Arg Glu Glu Met Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
            500                 505                 510

Pro Glu Asn Asn Tyr Lys Thr Thr Pro Pro Val Leu Asp Ser Asp Gly
        515                 520                 525

Ser Phe Phe Leu Tyr Ser Lys Leu Thr Val Asp Lys Ser Arg Trp Gln
    530                 535                 540
```

```
Gln Gly Asn Val Phe Ser Cys Ser Val Met His Glu Ala Leu His Asn
545                 550                 555                 560

His Tyr Thr Gln Lys Ser Leu Ser Leu Ser Pro Gly Lys
                565                 570

<210> SEQ ID NO 30
<211> LENGTH: 544
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Glu Asp Glu Asp Gln Asp
290                 295                 300

Tyr Ser Phe Pro Ile Ser Ser Ile Leu Glu Trp Thr Gly Gly Gly Thr
305                 310                 315                 320

His Thr Cys Pro Pro Cys Pro Ala Pro Glu Leu Leu Gly Gly Pro Ser
```

325                 330                 335

Val Phe Leu Phe Pro Pro Lys Pro Lys Asp Thr Leu Met Ile Ser Arg
            340                 345                 350

Thr Pro Glu Val Thr Cys Val Val Val Asp Val Ser His Glu Asp Pro
            355                 360                 365

Glu Val Lys Phe Asn Trp Tyr Val Asp Gly Val Glu Val His Asn Ala
            370                 375                 380

Lys Thr Lys Pro Arg Glu Glu Gln Tyr Asn Ser Thr Tyr Arg Val Val
385                 390                 395                 400

Ser Val Leu Thr Val Leu His Gln Asp Trp Leu Asn Gly Lys Glu Tyr
                405                 410                 415

Lys Cys Lys Val Ser Asn Lys Ala Leu Pro Ala Pro Ile Glu Lys Thr
            420                 425                 430

Ile Ser Lys Ala Lys Gly Gln Pro Arg Glu Pro Gln Val Tyr Thr Leu
            435                 440                 445

Pro Pro Ser Arg Glu Glu Met Thr Lys Asn Gln Val Ser Leu Thr Cys
450                 455                 460

Leu Val Lys Gly Phe Tyr Pro Ser Asp Ile Ala Val Glu Trp Glu Ser
465                 470                 475                 480

Asn Gly Gln Pro Glu Asn Asn Tyr Lys Thr Thr Pro Pro Val Leu Asp
                485                 490                 495

Ser Asp Gly Ser Phe Phe Leu Tyr Ser Lys Leu Thr Val Asp Lys Ser
            500                 505                 510

Arg Trp Gln Gln Gly Asn Val Phe Ser Cys Ser Val Met His Glu Ala
            515                 520                 525

Leu His Asn His Tyr Thr Gln Lys Ser Leu Ser Leu Ser Pro Gly Lys
            530                 535                 540

<210> SEQ ID NO 31
<211> LENGTH: 542
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Lys Lys Thr Cys Arg Asp Val Phe Cys Pro Gly
    130                 135                 140

Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
            165                 170                 175

Gly Asn Asp Gly Val Thr Tyr Ser Ser Ala Cys His Leu Arg Lys Ala
        180                 185                 190

Thr Cys Leu Leu Gly Arg Ser Ile Gly Leu Ala Tyr Glu Gly Lys Cys
    195                 200                 205

Ile Lys Ala Lys Ser Cys Glu Asp Ile Gln Cys Thr Gly Gly Lys Lys
210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
            245                 250                 255

Asn Ala Thr Tyr Ala Ser Glu Cys Ala Met Lys Glu Ala Ala Cys Ser
        260                 265                 270

Ser Gly Val Leu Leu Glu Val Lys His Ser Gly Ser Cys Asn Ser Ile
    275                 280                 285

Ser Glu Asp Thr Glu Glu Glu Asp Glu Asp Gln Asp Tyr Ser
290                 295                 300

Phe Pro Ile Ser Ser Ile Leu Glu Trp Thr Gly Gly Thr His Thr
305                 310                 315                 320

Cys Pro Pro Cys Pro Ala Pro Glu Leu Leu Gly Gly Pro Ser Val Phe
            325                 330                 335

Leu Phe Pro Pro Lys Pro Lys Asp Thr Leu Met Ile Ser Arg Thr Pro
        340                 345                 350

Glu Val Thr Cys Val Val Val Asp Val Ser His Glu Asp Pro Glu Val
    355                 360                 365

Lys Phe Asn Trp Tyr Val Asp Gly Val Glu Val His Asn Ala Lys Thr
370                 375                 380

Lys Pro Arg Glu Glu Gln Tyr Asn Ser Thr Tyr Arg Val Val Ser Val
385                 390                 395                 400

Leu Thr Val Leu His Gln Asp Trp Leu Asn Gly Lys Glu Tyr Lys Cys
            405                 410                 415

Lys Val Ser Asn Lys Ala Leu Pro Ala Pro Ile Glu Lys Thr Ile Ser
        420                 425                 430

Lys Ala Lys Gly Gln Pro Arg Glu Pro Gln Val Tyr Thr Leu Pro Pro
    435                 440                 445

Ser Arg Glu Glu Met Thr Lys Asn Gln Val Ser Leu Thr Cys Leu Val
450                 455                 460

Lys Gly Phe Tyr Pro Ser Asp Ile Ala Val Glu Trp Glu Ser Asn Gly
465                 470                 475                 480

Gln Pro Glu Asn Asn Tyr Lys Thr Thr Pro Pro Val Leu Asp Ser Asp
            485                 490                 495

Gly Ser Phe Phe Leu Tyr Ser Lys Leu Thr Val Asp Lys Ser Arg Trp
        500                 505                 510

Gln Gln Gly Asn Val Phe Ser Cys Ser Val Met His Glu Ala Leu His
    515                 520                 525

Asn His Tyr Thr Gln Lys Ser Leu Ser Leu Ser Pro Gly Lys
530                 535                 540

<210> SEQ ID NO 32
<211> LENGTH: 544
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 32

```
Met Val Arg Ala Arg His Gln Pro Gly Gly Leu Cys Leu Leu Leu Leu
 1               5                  10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Cys Ser Ser
290                 295                 300

Gly Val Leu Leu Glu Val Lys His Ser Gly Ser Cys Asn Thr Gly Gly
305                 310                 315                 320

Gly Val Glu Cys Pro Cys Pro Ala Pro Val Ala Gly Pro Ser
                325                 330                 335

Val Phe Leu Phe Pro Lys Pro Lys Asp Thr Leu Met Ile Ser Arg
            340                 345                 350

Thr Pro Glu Val Thr Cys Val Val Asp Val Ser His Glu Asp Pro
        355                 360                 365

Glu Val Gln Phe Asn Trp Tyr Val Asp Gly Val Glu Val His Asn Ala
370                 375                 380
```

```
Lys Thr Lys Pro Arg Glu Glu Gln Phe Asn Ser Thr Phe Arg Val Val
385                 390                 395                 400

Ser Val Leu Thr Val Val His Gln Asp Trp Leu Asn Gly Lys Glu Tyr
            405                 410                 415

Lys Cys Lys Val Ser Asn Lys Gly Leu Pro Ala Pro Ile Glu Lys Thr
        420                 425                 430

Ile Ser Lys Thr Lys Gly Gln Pro Arg Glu Pro Gln Val Tyr Thr Leu
    435                 440                 445

Pro Pro Ser Arg Glu Glu Met Thr Lys Asn Gln Val Ser Leu Thr Cys
    450                 455                 460

Leu Val Lys Gly Phe Tyr Pro Ser Asp Ile Ala Val Glu Trp Glu Ser
465                 470                 475                 480

Asn Gly Gln Pro Glu Asn Asn Tyr Lys Thr Thr Pro Pro Met Leu Asp
            485                 490                 495

Ser Asp Gly Ser Phe Phe Leu Tyr Ser Lys Leu Thr Val Asp Lys Ser
            500                 505                 510

Arg Trp Gln Gln Gly Asn Val Phe Ser Cys Ser Val Met His Glu Ala
        515                 520                 525

Leu His Asn His Tyr Thr Gln Lys Ser Leu Ser Leu Ser Pro Gly Lys
    530                 535                 540

<210> SEQ ID NO 33
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
            85                  90                  95

Thr Trp Lys Gly Pro Val Cys Gly Leu Asp Gly Lys Thr Tyr Arg Asn
        100                 105                 110

Glu Cys Ala Leu Leu Lys Ala Arg Cys Lys Glu Gln Pro Glu Leu Glu
    115                 120                 125

Val Gln Tyr Gln Gly Arg Cys Lys Lys Thr Cys Arg Asp Val Phe Cys
130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
            165                 170                 175

Leu Cys Gly Asn Asp Gly Val Thr Tyr Ser Ser Ala Cys His Leu Arg
        180                 185                 190

Lys Ala Thr Cys Leu Leu Gly Arg Ser Ile Gly Leu Ala Tyr Glu Gly
    195                 200                 205
```

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                    245                 250                 255

Ser Asp Asn Ala Thr Tyr Ala Ser Glu Cys Ala Met Lys Glu Ala Ala
                260                 265                 270

Cys Ser Ser Gly Val Leu Leu Glu Val Lys His Ser Gly Ser Cys Asn
            275                 280                 285

Thr Gly Gly Gly Val Glu Cys Pro Pro Cys Pro Ala Pro Pro Val Ala
290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
                325                 330                 335

Glu Asp Pro Glu Val Gln Phe Asn Trp Tyr Val Asp Gly Val Glu Val
            340                 345                 350

His Asn Ala Lys Thr Lys Pro Arg Glu Glu Gln Phe Asn Ser Thr Phe
        355                 360                 365

Arg Val Val Ser Val Leu Thr Val Val His Gln Asp Trp Leu Asn Gly
370                 375                 380

Lys Glu Tyr Lys Cys Lys Val Ser Asn Lys Gly Leu Pro Ala Pro Ile
385                 390                 395                 400

Glu Lys Thr Ile Ser Lys Thr Lys Gly Gln Pro Arg Glu Pro Gln Val
                405                 410                 415

Tyr Thr Leu Pro Pro Ser Arg Glu Glu Met Thr Lys Asn Gln Val Ser
            420                 425                 430

Leu Thr Cys Leu Val Lys Gly Phe Tyr Pro Ser Asp Ile Ala Val Glu
        435                 440                 445

Trp Glu Ser Asn Gly Gln Pro Glu Asn Asn Tyr Lys Thr Thr Pro Pro
450                 455                 460

Met Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                485                 490                 495

His Glu Ala Leu His Asn His Tyr Thr Gln Lys Ser Leu Ser Leu Ser
            500                 505                 510

Pro Gly Lys
    515

<210> SEQ ID NO 34
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met

```
             35                  40                  45
Ile Phe Asn Gly Gly Ala Pro Asn Cys Ile Pro Cys Lys Glu Thr Cys
 50                  55                  60
Glu Asn Val Asp Cys Gly Pro Gly Lys Lys Cys Arg Met Asn Lys Lys
 65                  70                  75                  80
Asn Lys Pro Arg Cys Val Cys Ala Pro Asp Cys Ser Asn Ile Thr Trp
                 85                  90                  95
Lys Gly Pro Val Cys Gly Leu Asp Gly Lys Thr Tyr Arg Asn Glu Cys
                100                 105                 110
Ala Leu Leu Lys Ala Arg Cys Lys Glu Gln Pro Glu Leu Glu Val Gln
            115                 120                 125
Tyr Gln Gly Arg Cys Lys Lys Thr Cys Arg Asp Val Phe Cys Pro Gly
        130                 135                 140
Ser Ser Thr Cys Val Val Asp Gln Thr Asn Asn Ala Tyr Cys Val Thr
145                 150                 155                 160
Cys Asn Arg Ile Cys Pro Glu Pro Ala Ser Ser Glu Gln Tyr Leu Cys
                165                 170                 175
Gly Asn Asp Gly Val Thr Tyr Ser Ser Ala Cys His Leu Arg Lys Ala
            180                 185                 190
Thr Cys Leu Leu Gly Arg Ser Ile Gly Leu Ala Tyr Glu Gly Lys Cys
        195                 200                 205
Ile Lys Ala Lys Ser Cys Glu Asp Ile Gln Cys Thr Gly Gly Lys Lys
210                 215                 220
Cys Leu Trp Asp Phe Lys Val Gly Arg Gly Arg Cys Ser Leu Cys Asp
225                 230                 235                 240
Glu Leu Cys Pro Asp Ser Lys Ser Asp Glu Pro Val Cys Ala Ser Asp
                245                 250                 255
Asn Ala Thr Tyr Ala Ser Glu Cys Ala Met Lys Glu Ala Ala Cys Ser
            260                 265                 270
Ser Gly Val Leu Leu Glu Val Lys His Ser Gly Ser Cys Asn Thr Gly
        275                 280                 285
Gly Gly Val Glu Cys Pro Pro Cys Pro Ala Pro Pro Val Ala Gly Pro
    290                 295                 300
Ser Val Phe Leu Phe Pro Pro Lys Pro Lys Asp Thr Leu Met Ile Ser
305                 310                 315                 320
Arg Thr Pro Glu Val Thr Cys Val Val Val Asp Val Ser His Glu Asp
                325                 330                 335
Pro Glu Val Gln Phe Asn Trp Tyr Val Asp Gly Val Glu Val His Asn
            340                 345                 350
Ala Lys Thr Lys Pro Arg Glu Glu Gln Phe Asn Ser Thr Phe Arg Val
        355                 360                 365
Val Ser Val Leu Thr Val Val His Gln Asp Trp Leu Asn Gly Lys Glu
    370                 375                 380
Tyr Lys Cys Lys Val Ser Asn Lys Gly Leu Pro Ala Pro Ile Glu Lys
385                 390                 395                 400
Thr Ile Ser Lys Thr Lys Gly Gln Pro Arg Glu Pro Gln Val Tyr Thr
                405                 410                 415
Leu Pro Pro Ser Arg Glu Glu Met Thr Lys Asn Gln Val Ser Leu Thr
            420                 425                 430
Cys Leu Val Lys Gly Phe Tyr Pro Ser Asp Ile Ala Val Glu Trp Glu
        435                 440                 445
Ser Asn Gly Gln Pro Glu Asn Asn Tyr Lys Thr Thr Pro Pro Met Leu
    450                 455                 460
```

```
Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys

<210> SEQ ID NO 35
<211> LENGTH: 571
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
290                 295                 300
```

Gly Val Leu Glu Val Lys His Ser Gly Cys Asn Ser Ile Ser
305                 310                 315                 320

Glu Asp Thr Glu Glu Glu Glu Asp Glu Asp Gln Asp Tyr Ser Phe
            325                 330                 335

Pro Ile Ser Ser Ile Leu Glu Trp Thr Gly Gly Val Glu Cys Pro
            340                 345                 350

Pro Cys Pro Ala Pro Pro Val Ala Gly Pro Ser Val Phe Leu Phe Pro
            355                 360                 365

Pro Lys Pro Lys Asp Thr Leu Met Ile Ser Arg Thr Pro Glu Val Thr
370                 375                 380

Cys Val Val Val Asp Val Ser His Glu Asp Pro Glu Val Gln Phe Asn
385                 390                 395                 400

Trp Tyr Val Asp Gly Val Glu Val His Asn Ala Lys Thr Lys Pro Arg
            405                 410                 415

Glu Glu Gln Phe Asn Ser Thr Phe Arg Val Val Ser Val Leu Thr Val
            420                 425                 430

Val His Gln Asp Trp Leu Asn Gly Lys Glu Tyr Lys Cys Lys Val Ser
            435                 440                 445

Asn Lys Gly Leu Pro Ala Pro Ile Glu Lys Thr Ile Ser Lys Thr Lys
450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Met Leu Asp Ser Asp Gly Ser Phe
            515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
            565                 570

<210> SEQ ID NO 36
<211> LENGTH: 542
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
            50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile

-continued

```
                85                  90                  95
Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
            130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
                180                 185                 190

Lys Ala Thr Cys Leu Leu Gly Arg Ser Ile Gly Leu Ala Tyr Glu Gly
                195                 200                 205

Lys Cys Ile Lys Ala Lys Ser Cys Glu Asp Ile Gln Cys Thr Gly Gly
                210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
                260                 265                 270

Cys Ser Ser Gly Val Leu Leu Glu Val Lys His Ser Gly Ser Cys Asn
                275                 280                 285

Ser Ile Ser Glu Asp Thr Glu Glu Glu Glu Asp Glu Asp Gln Asp
                290                 295                 300

Tyr Ser Phe Pro Ile Ser Ser Ile Leu Glu Trp Thr Gly Gly Gly Val
305                 310                 315                 320

Glu Cys Pro Pro Cys Pro Ala Pro Val Ala Gly Pro Ser Val Phe
                325                 330                 335

Leu Phe Pro Pro Lys Pro Lys Asp Thr Leu Met Ile Ser Arg Thr Pro
                340                 345                 350

Glu Val Thr Cys Val Val Val Asp Val Ser His Glu Asp Pro Glu Val
                355                 360                 365

Gln Phe Asn Trp Tyr Val Asp Gly Val Glu Val His Asn Ala Lys Thr
                370                 375                 380

Lys Pro Arg Glu Glu Gln Phe Asn Ser Thr Phe Arg Val Val Ser Val
385                 390                 395                 400

Leu Thr Val Val His Gln Asp Trp Leu Asn Gly Lys Glu Tyr Lys Cys
                405                 410                 415

Lys Val Ser Asn Lys Gly Leu Pro Ala Pro Ile Glu Lys Thr Ile Ser
                420                 425                 430

Lys Thr Lys Gly Gln Pro Arg Glu Pro Gln Val Tyr Thr Leu Pro Pro
                435                 440                 445

Ser Arg Glu Glu Met Thr Lys Asn Gln Val Ser Leu Thr Cys Leu Val
450                 455                 460

Lys Gly Phe Tyr Pro Ser Asp Ile Ala Val Glu Trp Glu Ser Asn Gly
465                 470                 475                 480

Gln Pro Glu Asn Asn Tyr Lys Thr Thr Pro Pro Met Leu Asp Ser Asp
                485                 490                 495

Gly Ser Phe Phe Leu Tyr Ser Lys Leu Thr Val Asp Lys Ser Arg Trp
                500                 505                 510
```

-continued

Gln Gln Gly Asn Val Phe Ser Cys Ser Val Met His Glu Ala Leu His
        515                 520                 525

Asn His Tyr Thr Gln Lys Ser Leu Ser Leu Ser Pro Gly Lys
    530                 535                 540

<210> SEQ ID NO 37
<211> LENGTH: 540
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Lys Lys Thr Cys Arg Asp Val Phe Cys Pro Gly
    130                 135                 140

Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
                165                 170                 175

Gly Asn Asp Gly Val Thr Tyr Ser Ser Ala Cys His Leu Arg Lys Ala
            180                 185                 190

Thr Cys Leu Leu Gly Arg Ser Ile Gly Leu Ala Tyr Glu Gly Lys Cys
        195                 200                 205

Ile Lys Ala Lys Ser Cys Glu Asp Ile Gln Cys Thr Gly Gly Lys Lys
    210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
                245                 250                 255

Asn Ala Thr Tyr Ala Ser Glu Cys Ala Met Lys Glu Ala Ala Cys Ser
            260                 265                 270

Ser Gly Val Leu Leu Glu Val Lys His Ser Gly Ser Cys Asn Ser Ile
        275                 280                 285

Ser Glu Asp Thr Glu Glu Glu Glu Asp Glu Asp Gln Asp Tyr Ser
    290                 295                 300

Phe Pro Ile Ser Ser Ile Leu Glu Trp Thr Gly Gly Gly Val Glu Cys
305                 310                 315                 320

Pro Pro Cys Pro Ala Pro Pro Val Ala Gly Pro Ser Val Phe Leu Phe

```
               325                 330                 335
Pro Pro Lys Pro Lys Asp Thr Leu Met Ile Ser Arg Thr Pro Glu Val
            340                 345                 350

Thr Cys Val Val Val Asp Val Ser His Glu Asp Pro Glu Val Gln Phe
            355                 360                 365

Asn Trp Tyr Val Asp Gly Val Glu Val His Asn Ala Lys Thr Lys Pro
        370                 375                 380

Arg Glu Glu Gln Phe Asn Ser Thr Phe Arg Val Val Ser Val Leu Thr
385                 390                 395                 400

Val Val His Gln Asp Trp Leu Asn Gly Lys Glu Tyr Lys Cys Lys Val
                405                 410                 415

Ser Asn Lys Gly Leu Pro Ala Pro Ile Glu Lys Thr Ile Ser Lys Thr
                420                 425                 430

Lys Gly Gln Pro Arg Glu Pro Gln Val Tyr Thr Leu Pro Pro Ser Arg
            435                 440                 445

Glu Glu Met Thr Lys Asn Gln Val Ser Leu Thr Cys Leu Val Lys Gly
            450                 455                 460

Phe Tyr Pro Ser Asp Ile Ala Val Glu Trp Glu Ser Asn Gly Gln Pro
465                 470                 475                 480

Glu Asn Asn Tyr Lys Thr Thr Pro Pro Met Leu Asp Ser Asp Gly Ser
                485                 490                 495

Phe Phe Leu Tyr Ser Lys Leu Thr Val Asp Lys Ser Arg Trp Gln Gln
                500                 505                 510

Gly Asn Val Phe Ser Cys Ser Val Met His Glu Ala Leu His Asn His
            515                 520                 525

Tyr Thr Gln Lys Ser Leu Ser Leu Ser Pro Gly Lys
            530                 535                 540

<210> SEQ ID NO 38
<211> LENGTH: 549
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140
```

```
Leu Leu Lys Ala Arg Cys Lys Glu Gln Pro Leu Glu Val Gln Tyr
145                 150                 155                 160

Gln Gly Arg Cys Lys Thr Cys Arg Asp Val Phe Cys Pro Gly Ser
            165                 170                 175

Ser Thr Cys Val Val Asp Gln Thr Asn Asn Ala Tyr Cys Val Thr Cys
        180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
        210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
            245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
        290                 295                 300

Gly Val Leu Leu Glu Val Lys His Ser Gly Ser Cys Asn Ser Ile Ser
305                 310                 315                 320

Thr Gly Gly Gly Thr His Thr Cys Pro Pro Cys Pro Ala Pro Glu Leu
            325                 330                 335

Leu Gly Gly Pro Ser Val Phe Leu Phe Pro Pro Lys Pro Lys Asp Thr
            340                 345                 350

Leu Met Ile Ser Arg Thr Pro Glu Val Thr Cys Val Val Val Asp Val
            355                 360                 365

Ser His Glu Asp Pro Glu Val Lys Phe Asn Trp Tyr Val Asp Gly Val
            370                 375                 380

Glu Val His Asn Ala Lys Thr Lys Pro Arg Glu Glu Gln Tyr Asn Ser
385                 390                 395                 400

Thr Tyr Arg Val Val Ser Val Leu Thr Val Leu His Gln Asp Trp Leu
            405                 410                 415

Asn Gly Lys Glu Tyr Lys Cys Lys Val Ser Asn Lys Ala Leu Pro Ala
            420                 425                 430

Pro Ile Glu Lys Thr Ile Ser Lys Ala Lys Gly Gln Pro Arg Glu Pro
            435                 440                 445

Gln Val Tyr Thr Leu Pro Pro Ser Arg Glu Glu Met Thr Lys Asn Gln
450                 455                 460

Val Ser Leu Thr Cys Leu Val Lys Gly Phe Tyr Pro Ser Asp Ile Ala
465                 470                 475                 480

Val Glu Trp Glu Ser Asn Gly Gln Pro Glu Asn Asn Tyr Lys Thr Thr
            485                 490                 495

Pro Pro Val Leu Asp Ser Asp Gly Ser Phe Phe Leu Tyr Ser Lys Leu
            500                 505                 510

Thr Val Asp Lys Ser Arg Trp Gln Gln Gly Asn Val Phe Ser Cys Ser
            515                 520                 525

Val Met His Glu Ala Leu His Asn His Tyr Thr Gln Lys Ser Leu Ser
            530                 535                 540

Leu Ser Pro Gly Lys
545
```

<210> SEQ ID NO 39
<211> LENGTH: 520
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Thr Gly Gly Gly Thr His Thr Cys Pro Pro Cys Pro Ala
    290                 295                 300

Pro Glu Leu Leu Gly Gly Pro Ser Val Phe Leu Phe Pro Pro Lys Pro
305                 310                 315                 320

Lys Asp Thr Leu Met Ile Ser Arg Thr Pro Glu Val Thr Cys Val Val
                325                 330                 335

Val Asp Val Ser His Glu Asp Pro Glu Val Lys Phe Asn Trp Tyr Val
            340                 345                 350

Asp Gly Val Glu Val His Asn Ala Lys Thr Lys Pro Arg Glu Glu Gln
        355                 360                 365
```

```
Tyr Asn Ser Thr Tyr Arg Val Val Ser Val Leu Thr Val Leu His Gln
        370                 375                 380

Asp Trp Leu Asn Gly Lys Glu Tyr Lys Cys Lys Val Ser Asn Lys Ala
385                 390                 395                 400

Leu Pro Ala Pro Ile Glu Lys Thr Ile Ser Lys Ala Lys Gly Gln Pro
                405                 410                 415

Arg Glu Pro Gln Val Tyr Thr Leu Pro Pro Ser Arg Glu Glu Met Thr
                420                 425                 430

Lys Asn Gln Val Ser Leu Thr Cys Leu Val Lys Gly Phe Tyr Pro Ser
                435                 440                 445

Asp Ile Ala Val Glu Trp Glu Ser Asn Gly Gln Pro Glu Asn Asn Tyr
        450                 455                 460

Lys Thr Thr Pro Pro Val Leu Asp Ser Asp Gly Ser Phe Phe Leu Tyr
465                 470                 475                 480

Ser Lys Leu Thr Val Asp Lys Ser Arg Trp Gln Gln Gly Asn Val Phe
                485                 490                 495

Ser Cys Ser Val Met His Glu Ala Leu His Asn His Tyr Thr Gln Lys
                500                 505                 510

Ser Leu Ser Leu Ser Pro Gly Lys
        515                 520

<210> SEQ ID NO 40
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
                20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
                100                 105                 110

Ala Leu Leu Lys Ala Arg Cys Lys Glu Gln Pro Glu Leu Glu Val Gln
        115                 120                 125

Tyr Gln Gly Arg Cys Lys Lys Thr Cys Arg Asp Val Phe Cys Pro Gly
        130                 135                 140

Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
                165                 170                 175

Gly Asn Asp Gly Val Thr Tyr Ser Ser Ala Cys His Leu Arg Lys Ala
                180                 185                 190

Thr Cys Leu Leu Gly Arg Ser Ile Gly Leu Ala Tyr Glu Gly Lys Cys
        195                 200                 205
```

Ile Lys Ala Lys Ser Cys Glu Asp Ile Gln Cys Thr Gly Gly Lys Lys
    210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
                245                 250                 255

Asn Ala Thr Tyr Ala Ser Glu Cys Ala Met Lys Glu Ala Ala Cys Ser
            260                 265                 270

Ser Gly Val Leu Leu Glu Val Lys His Ser Gly Ser Cys Asn Ser Ile
        275                 280                 285

Ser Thr Gly Gly Gly Thr His Thr Cys Pro Pro Cys Pro Ala Pro Glu
    290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Lys Phe Asn Trp Tyr Val Asp Gly
            340                 345                 350

Val Glu Val His Asn Ala Lys Thr Lys Pro Arg Glu Glu Gln Tyr Asn
        355                 360                 365

Ser Thr Tyr Arg Val Val Ser Val Leu Thr Val Leu His Gln Asp Trp
    370                 375                 380

Leu Asn Gly Lys Glu Tyr Lys Cys Lys Val Ser Asn Lys Ala Leu Pro
385                 390                 395                 400

Ala Pro Ile Glu Lys Thr Ile Ser Lys Ala Lys Gly Gln Pro Arg Glu
                405                 410                 415

Pro Gln Val Tyr Thr Leu Pro Pro Ser Arg Glu Glu Met Thr Lys Asn
            420                 425                 430

Gln Val Ser Leu Thr Cys Leu Val Lys Gly Phe Tyr Pro Ser Asp Ile
        435                 440                 445

Ala Val Glu Trp Glu Ser Asn Gly Gln Pro Glu Asn Asn Tyr Lys Thr
    450                 455                 460

Thr Pro Pro Val Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
            500                 505                 510

Ser Leu Ser Pro Gly Lys
        515

<210> SEQ ID NO 41
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr

```
              35                  40                  45
Glu Leu Ser Lys Glu Glu Cys Cys Ser Thr Gly Arg Leu Ser Thr Ser
 50                  55                  60

Trp Thr Glu Glu Asp Val Asn Asp Asn Thr Leu Phe Lys Trp Met Ile
 65                  70                  75                  80

Phe Asn Gly Gly Ala Pro Asn Cys Ile Pro Cys Lys Glu Thr Cys Glu
                 85                  90                  95

Asn Val Asp Cys Gly Pro Gly Lys Lys Cys Arg Met Asn Lys Lys Asn
                100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
        130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

Thr Gly Gly Val Glu Cys Pro Pro Cys Pro Ala Pro Pro Val Ala
                325                 330                 335

Gly Pro Ser Val Phe Leu Phe Pro Pro Lys Pro Lys Asp Thr Leu Met
            340                 345                 350

Ile Ser Arg Thr Pro Glu Val Thr Cys Val Val Val Asp Val Ser His
        355                 360                 365

Glu Asp Pro Glu Val Gln Phe Asn Trp Tyr Val Asp Gly Val Glu Val
    370                 375                 380

His Asn Ala Lys Thr Lys Pro Arg Glu Glu Gln Phe Asn Ser Thr Phe
385                 390                 395                 400

Arg Val Val Ser Val Leu Thr Val Val His Gln Asp Trp Leu Asn Gly
                405                 410                 415

Lys Glu Tyr Lys Cys Lys Val Ser Asn Lys Gly Leu Pro Ala Pro Ile
            420                 425                 430

Glu Lys Thr Ile Ser Lys Thr Lys Gly Gln Pro Arg Glu Pro Gln Val
        435                 440                 445

Tyr Thr Leu Pro Pro Ser Arg Glu Glu Met Thr Lys Asn Gln Val Ser
    450                 455                 460
```

```
Leu Thr Cys Leu Val Lys Gly Phe Tyr Pro Ser Asp Ile Ala Val Glu
465                 470                 475                 480

Trp Glu Ser Asn Gly Gln Pro Glu Asn Asn Tyr Lys Thr Thr Pro Pro
                485                 490                 495

Met Leu Asp Ser Asp Gly Ser Phe Phe Leu Tyr Ser Lys Leu Thr Val
            500                 505                 510

Asp Lys Ser Arg Trp Gln Gln Gly Asn Val Phe Ser Cys Ser Val Met
        515                 520                 525

His Glu Ala Leu His Asn His Tyr Thr Gln Lys Ser Leu Ser Leu Ser
    530                 535                 540

Pro Gly Lys
545

<210> SEQ ID NO 42
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
```

260                 265                 270
Cys Ser Ser Gly Val Leu Leu Glu Val Lys His Ser Gly Ser Cys Asn
            275                 280                 285
Ser Ile Ser Thr Gly Gly Val Glu Cys Pro Pro Cys Pro Ala Pro
        290                 295                 300
Pro Val Ala Gly Pro Ser Val Phe Leu Phe Pro Pro Lys Pro Lys Asp
305                 310                 315                 320
Thr Leu Met Ile Ser Arg Thr Pro Glu Val Thr Cys Val Val Asp
                    325                 330                 335
Val Ser His Glu Asp Pro Glu Val Gln Phe Asn Trp Tyr Val Asp Gly
            340                 345                 350
Val Glu Val His Asn Ala Lys Thr Lys Pro Arg Glu Glu Gln Phe Asn
        355                 360                 365
Ser Thr Phe Arg Val Val Ser Val Leu Thr Val Val His Gln Asp Trp
    370                 375                 380
Leu Asn Gly Lys Glu Tyr Lys Cys Lys Val Ser Asn Lys Gly Leu Pro
385                 390                 395                 400
Ala Pro Ile Glu Lys Thr Ile Ser Lys Thr Lys Gly Gln Pro Arg Glu
                405                 410                 415
Pro Gln Val Tyr Thr Leu Pro Pro Ser Arg Glu Glu Met Thr Lys Asn
            420                 425                 430
Gln Val Ser Leu Thr Cys Leu Val Lys Gly Phe Tyr Pro Ser Asp Ile
        435                 440                 445
Ala Val Glu Trp Glu Ser Asn Gly Gln Pro Glu Asn Asn Tyr Lys Thr
    450                 455                 460
Thr Pro Pro Met Leu Asp Ser Asp Gly Ser Phe Phe Leu Tyr Ser Lys
465                 470                 475                 480
Leu Thr Val Asp Lys Ser Arg Trp Gln Gln Gly Asn Val Phe Ser Cys
                485                 490                 495
Ser Val Met His Glu Ala Leu His Asn His Tyr Thr Gln Lys Ser Leu
            500                 505                 510
Ser Leu Ser Pro Gly Lys
        515

<210> SEQ ID NO 43
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Cys Trp Leu Arg Gln Ala Lys Asn Gly Arg Cys Gln Val Leu Tyr Lys
1               5                   10                  15
Thr Glu Leu Ser Lys Glu Glu Cys Cys Ser Thr Gly Arg Leu Ser Thr
            20                  25                  30
Ser Trp Thr Glu Glu Asp Val Asn Asp Asn Thr Leu Phe Lys Trp Met
        35                  40                  45
Ile Phe Asn Gly Gly Ala Pro Asn Cys Ile Pro Cys Lys Glu Thr Cys
    50                  55                  60
Glu Asn Val Asp Cys Gly Pro Gly Lys Lys Cys Arg Met Asn Lys Lys
65                  70                  75                  80
Asn Lys Pro Arg Cys Val Cys Ala Pro Asp Cys Ser Asn Ile Thr Trp
                85                  90                  95

```
Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Lys Lys Thr Cys Arg Asp Val Phe Cys Pro Gly
    130                 135                 140

Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
                165                 170                 175

Gly Asn Asp Gly Val Thr Tyr Ser Ser Ala Cys His Leu Arg Lys Ala
            180                 185                 190

Thr Cys Leu Leu Gly Arg Ser Ile Gly Leu Ala Tyr Glu Gly Lys Cys
        195                 200                 205

Ile Lys Ala Lys Ser Cys Glu Asp Ile Gln Cys Thr Gly Gly Lys Lys
    210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
                245                 250                 255

Asn Ala Thr Tyr Ala Ser Glu Cys Ala Met Lys Glu Ala Ala Cys Ser
            260                 265                 270

Ser Gly Val Leu Leu Glu Val Lys His Ser Gly Ser Cys Asn Ser Ile
        275                 280                 285

Ser Thr Gly Gly Gly Val Glu Cys Pro Pro Cys Pro Ala Pro Pro Val
    290                 295                 300

Ala Gly Pro Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
                325                 330                 335

His Glu Asp Pro Glu Val Gln Phe Asn Trp Tyr Val Asp Gly Val Glu
            340                 345                 350

Val His Asn Ala Lys Thr Lys Pro Arg Glu Glu Gln Phe Asn Ser Thr
        355                 360                 365

Phe Arg Val Val Ser Val Leu Thr Val Val His Gln Asp Trp Leu Asn
    370                 375                 380

Gly Lys Glu Tyr Lys Cys Lys Val Ser Asn Lys Gly Leu Pro Ala Pro
385                 390                 395                 400

Ile Glu Lys Thr Ile Ser Lys Thr Lys Gly Gln Pro Arg Glu Pro Gln
                405                 410                 415

Val Tyr Thr Leu Pro Pro Ser Arg Glu Glu Met Thr Lys Asn Gln Val
            420                 425                 430

Ser Leu Thr Cys Leu Val Lys Gly Phe Tyr Pro Ser Asp Ile Ala Val
        435                 440                 445

Glu Trp Glu Ser Asn Gly Gln Pro Glu Asn Asn Tyr Lys Thr Thr Pro
    450                 455                 460

Pro Met Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Met His Glu Ala Leu His Asn His Tyr Thr Gln Lys Ser Leu Ser Leu
            500                 505                 510

Ser Pro Gly Lys
```

<210> SEQ ID NO 44
<211> LENGTH: 1641
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
atggtccgcg cgaggcacca gccgggtggg ctttgcctcc tgctgctgct gctctgccag      60
ttcatggagg accgcagtgc ccaggctggg aactgctggc tccgtcaagc gaagaacggc     120
cgctgccagg tcctgtacaa gaccgaactg agcaaggagg agtgctgcag caccggccgg     180
ctgagcacct cgtggaccga ggaggacgtg aatgacaaca cactcttcaa gtggatgatt     240
ttcaacgggg gcgcccccaa ctgcatcccc tgtaaagaaa cgtgtgagaa cgtggactgt     300
ggacctggga aaaatgccg aatgaacaag aagaacaaac cccgctgcgt ctgcgccccg     360
gattgttcca acatcacctg gaagggtcca gtctgcgggc tggatgggaa acctaccgc     420
aatgaatgtg cactcctaaa ggcaagatgt aaagagcagc cagaactgga agtccagtac     480
caaggcagat gtaaaaagac ttgtcgggat gttttctgtc caggcagctc cacatgtgtg     540
gtggaccaga ccaataatgc ctactgtgtg acctgtaatc ggatttgccc agagcctgct     600
tcctctgagc aatatctctg tgggaatgat ggagtcacct actccagtgc ctgccacctg     660
agaaaggcta cctgcctgct gggcagatct attggattag cctatgaggg aaagtgtatc     720
aaagcaaagt cctgtgaaga tatccagtgc actggtggga aaaatgtttt atgggatttc     780
aaggttggga gaggccggtg ttccctctgt gatgagctgt gccctgacag taagtcggat     840
gagcctgtct gtgccagtga caatgccact tatgccagcg agtgtgccat gaaggaagct     900
gcctgctcct caggtgtgct actggaagta aagcactccg gatcttgcaa caccggtggt     960
ggagtcgagt gcccaccgtg cccagcacca cctgtggcag gaccgtcagt cttcctcttc    1020
cccccaaaac ccaaggacac cctcatgatc tcccggaccc ctgaggtcac gtgcgtggtg    1080
gtggacgtga gccacgaaga ccccgaggtc cagttcaact ggtacgtgga cggcgtggag    1140
gtgcataatg ccaagacaaa gccacgggag gagcagttca acagcacgtt ccgtgtggtc    1200
agcgtcctca ccgtcgtgca ccaggactgg ctgaacggca aggagtacaa gtgcaaggtc    1260
tccaacaaag cctcccagc ccccatcgag aaaaccatct ccaaaaccaa agggcagccc    1320
cgagaaccac aggtgtacac cctgccccca tcccgggagg agatgaccaa gaaccaggtc    1380
agcctgacct gcctggtcaa aggcttctac cccagcgaca tcgccgtgga gtgggagagc    1440
aatgggcagc cggagaacaa ctacaagacc acacctccca tgctggactc cgacggctcc    1500
ttcttcctct acagcaagct caccgtggac aagagcaggt ggcagcaggg gaacgtcttc    1560
tcatgctccg tgatgcatga ggctctgcac aaccactaca cgcagaagag cctctccctg    1620
tctccgggta aatgagaatt c                                              1641
```

<210> SEQ ID NO 45
<211> LENGTH: 1722
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
atggtccgcg cgaggcacca gccgggtggg cttcgcctcc tgctgctgct gctctgccag    60
ttcatggagg accgcagtgc ccaggctggg aactgctggc tccgtcaagc gaagaacggc   120
cgctgccagg tcctgtacaa gaccgaactg agcaaggagg agtgctgcag caccggccgg   180
ctgagcacct cgtggaccga ggaggacgtg aatgacaaca cactcttcaa gtggatgatt   240
ttcaacgggg gtgcccccaa ctgcatcccc tgtaaagaaa cgtgtgagaa cgtggactgt   300
ggacctggga aaaatgccg aatgaacaag aagaacaaac ccgctgcgt ctgcgccccg    360
gattgttcca acatcacctg aagggtcca gtctgcgggc tggatgggaa aacctaccgc   420
aatgaatgtg cactcctaaa ggcaagatgt aaagagcagc agaactgga agtccagtac   480
caaggcagat gtaaaaagac ttgtcgggat gttttctgtc caggcagctc cacatgtgtg   540
gtggaccaga ccaataatgc ctactgtgtg acctgtaatc ggatttgccc agagcctgct   600
tcctctgagc aatatctctg tgggaatgat ggagtcacct actccagtgc ctgccacctg   660
agaaaggcta cctgcctgct gggcagatct attggattag cctatgaggg aaagtgtatc   720
aaagcaaagt cctgtgaaga tatccagtgc actggtggga aaaaatgttt atgggatttc   780
aaggttggga gaggccggtg ttccctctgt gatgagctgt gccctgacag taagtcggat   840
gagcctgtct gtgccagtga caatgccact tatgccagcg agtgtgccat gaaggaagct   900
gcctgctcct caggtgtgct actggaagta aagcactccg gatcttgcaa ctccatttcg   960
gaagacaccg aggaagagga ggaagatgaa gaccaggact acagctttcc tatatcttct  1020
attctagagt ggaccggtgg tggagtcgag tgcccaccgt gcccagcacc acctgtggca  1080
ggaccgtcag tcttcctctt ccccccaaaa cccaaggaca ccctcatgat ctcccggacc  1140
cctgaggtca cgtgcgtggt ggtggacgtg agccacgaag accccgaggt ccagttcaac  1200
tggtacgtgg acggcgtgga ggtgcataat gccaagacaa agccacggga ggagcagttc  1260
aacagcacgt tccgtgtggt cagcgtcctc accgtcgtgc accaggactg gctgaacggc  1320
aaggagtaca agtgcaaggt ctccaacaaa ggcctcccag cccccatcga gaaaaccatc  1380
tccaaaacca agggcagcc ccgagaacca caggtgtaca ccctgccccc atcccgggag  1440
gagatgacca agaaccaggt cagcctgacc tgcctggtca aaggcttcta ccccagcgac  1500
atcgccgtgg agtgggagag caatgggcag ccggagaaca actacaagac cacacctccc  1560
atgctggact ccgacggctc cttcttcctc tacagcaagc tcaccgtgga caagagcagg  1620
tggcagcagg ggaacgtctt ctcatgctcc gtgatgcatg aggctctgca caaccactac  1680
acgcagaaga gcctctccct gtctccgggt aaatgagaat tc                     1722
```

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Gly Gly Gly
1

<210> SEQ ID NO 47
<211> LENGTH: 6
<212> TYPE: PRT
<213> ORGANISM: Artificial Sequence
<220> FEATURE:

```
<223> OTHER INFORMATION: Description of Artificial Sequence: Synthetic
      6xHis tag

<400> SEQUENCE: 47

His His His His His His
1               5
```